US012753220B2

(12) United States Patent
Schiffer-Mannioui et al.

(10) Patent No.: US 12,753,220 B2

(45) Date of Patent: Oct. 6, 2026

(54) MESOTHELIN SPECIFIC CHIMERIC ANTIGEN RECEPTORS (CAR) FOR SOLID TUMORS CANCER IMMUNOTHERAPY

(71) Applicant: CELLECTIS, Paris (FR)

(72) Inventors: Cecile Schiffer-Mannioui, Villiers-sur-marne (FR); Philippe Duchateau, Saint Louis et Parahou (FR)

(73) Assignee: Cellectis, Paris (FR)

( * ) Notice: Subject to any disclaimer, the term of this patent is extended or adjusted under 35 U.S.C. 154(b) by 1067 days.

(21) Appl. No.: 17/788,133

(22) PCT Filed: Dec. 22, 2020

(86) PCT No.: PCT/EP2020/087673

§ 371 (c)(1),
(2) Date: Jun. 22, 2022

(87) PCT Pub. No.: WO2021/130250

PCT Pub. Date: Jul. 1, 2021

(65) Prior Publication Data

US 2023/0068949 A1 Mar. 2, 2023

(30) Foreign Application Priority Data

Dec. 23, 2019 (DK) .......................... PA 2019 70835

(51) Int. Cl.

| | |
|---|---|
| ***C07K 14/705*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 16/28*** | (2006.01) |
| ***C07K 16/30*** | (2006.01) |
| ***C12N 5/0783*** | (2010.01) |
| ***C12N 15/90*** | (2006.01) |

(52) U.S. Cl.

CPC ........ *C07K 14/70521* (2013.01); *A61K 40/11* (2025.01); *A61K 40/31* (2025.01); *A61K 40/4255* (2025.01); *A61P 35/00* (2018.01); *C07K 14/7051* (2013.01); *C07K 14/70517* (2013.01); *C07K 14/70578* (2013.01); *C07K 16/28* (2013.01); *C07K 16/30* (2013.01); *C12N 5/0636* (2013.01); *C12N 15/907* (2013.01); *A61K 2239/38* (2023.05); *A61K 2239/54* (2023.05); *C07K 2317/622* (2013.01); *C07K 2319/02* (2013.01); *C07K 2319/03* (2013.01); *C12N 2510/00* (2013.01)

(58) Field of Classification Search

CPC ...................................................... A61K 40/31

See application file for complete search history.

(56) References Cited

U.S. PATENT DOCUMENTS

| | | | | |
|---|---|---|---|---|
| 9,272,002 B2 * | 3/2016 | Powell, Jr. | ............. | A61K 40/31 |
| 2014/0004121 A1 | 1/2014 | Fanslow, III et al. | | |
| 2025/0034641 A1 * | 1/2025 | Sourdive | ............ | A61K 40/4211 |

FOREIGN PATENT DOCUMENTS

| | | | |
|---|---|---|---|
| EP | 3276000 | A2 | 1/2018 |
| WO | 2013/063419 | A2 | 5/2013 |
| WO | 2014/004549 | A2 | 1/2014 |
| WO | 2015090230 | A1 | 6/2015 |
| WO | 2015136001 | A1 | 9/2015 |
| WO | 2016/120216 | A1 | 8/2016 |
| WO | 2017125830 | A1 | 7/2017 |
| WO | 2017158337 | A1 | 9/2017 |
| WO | 2019/063018 | A1 | 4/2019 |

OTHER PUBLICATIONS

EMBO Journal vol. 14 No. 12 pp. 2784-2794 (Year: 1995).*
J. Mol Biol. , 334, pp. 103-118 (Year: 2003).*
PNAS, pp. E486-E495 (Year: 2017).*
Journal of Immunology, 152(1): pp. 146-152 (Year: 1994).*
Park et al. (Scientific Reports vol. 7, Article No. 14366, 2017).*
Zhao et al. (Journal of Hematology & Oncology (2018) 11:132).*
Lv Jiang et al, "Mesothelin as a biomarker for targeted therapy", Aug. 23, 2019, vol. 7, No. 1, 1-18.
Laurent Poirot et al, "Multiplex Genome-Edited T-cell Manufacturing Platform for "Off-the-Shelf" Adoptive T-cell Immunotherapies", Cancer Research—Proceedings: AACR Annual Meeting 2018; Apr. 14-18, 2018; Chicago, IL, vol. 75, No. 18, Jul. 16, 2015 (Jul. 16, 2015), p. 3853-3864.
Zhang et al. Modified CAR T cells targeting membrane-proximal epitope of mesothelin enhances the antitumor function against large solid tumor. Cell Death and Disease, 2019, 10(476), 1-12.

* cited by examiner

*Primary Examiner* — Gary B Nickol

(74) *Attorney, Agent, or Firm* — Arrigo, Lee, Guttman & Mouta-Bellum LLP

(57) ABSTRACT

The present invention relates to engineered immune cells expressing new mesothelin (MLSN) specific chimeric antigen receptors (anti-mesothelin CAR) and their use in the treatment of solid tumors, particularly suited for allogeneic cell immunotherapy.

17 Claims, 25 Drawing Sheets

Figure 1:
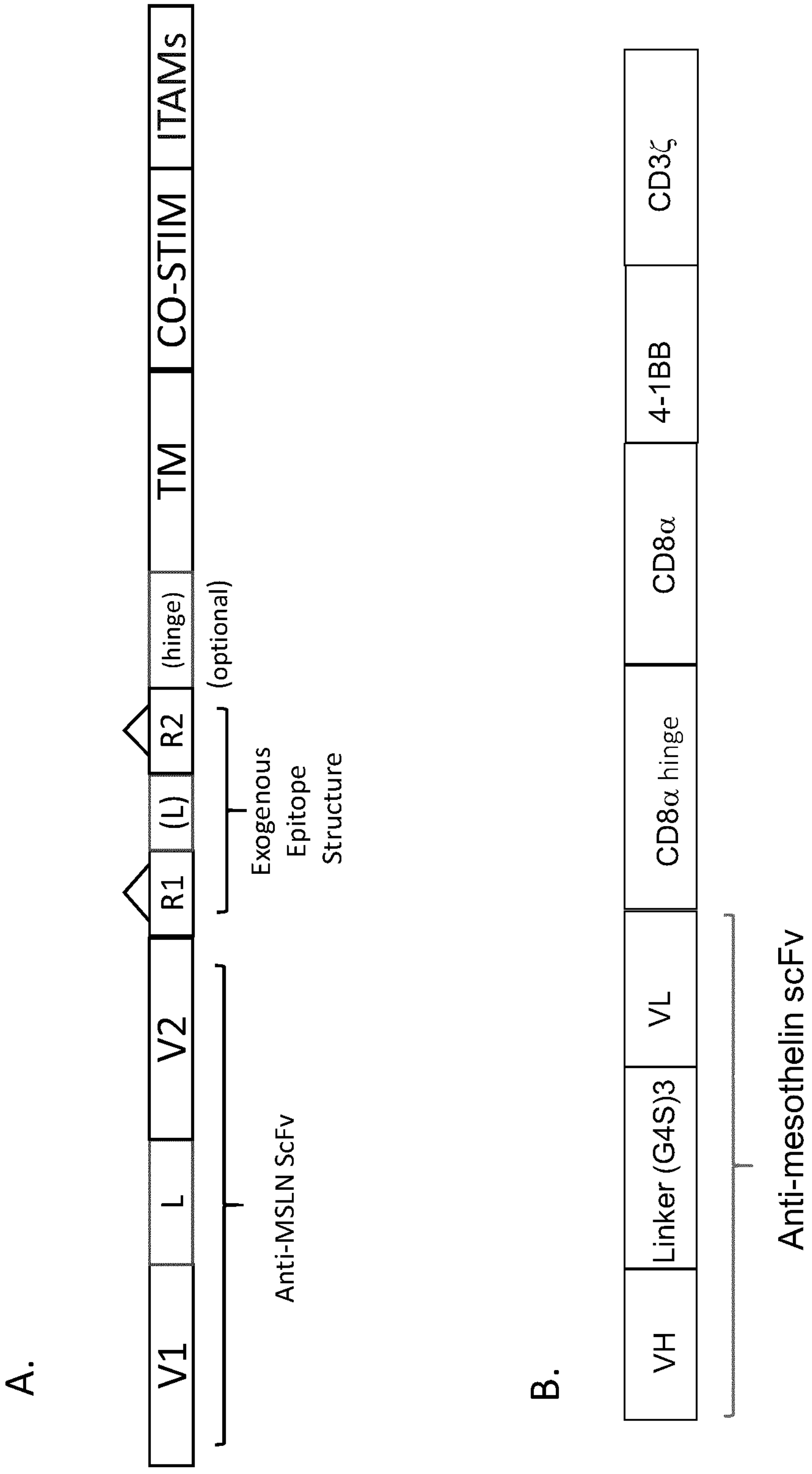

Specification includes a Sequence Listing.

Non-engineered T cells

T cells knocked out for the *TRAC* gene

T cells knocked out for the *TRAC* gene and depleted in TCRαβ+ cells

A.

B.

A. With MSLN

B. Without MSLN

A.

B.

MESOTHELIN SPECIFIC CHIMERIC ANTIGEN RECEPTORS (CAR) FOR SOLID TUMORS CANCER IMMUNOTHERAPY

FIELD OF THE INVENTION

The present invention relates to the field of cell immunotherapy and more particularly to engineered immune cells expressing new mesothelin (MLSN) specific chimeric antigen receptors (anti-mesothelin CAR) useful in the treatment of solid tumors.

BACKGROUND OF THE INVENTION

Chimeric antigen receptors (CAR) are synthetic receptors that target T cells to cell-surface antigens and augment T-cell function and persistence. Mesothelin is a cell-surface antigen implicated in tumor invasion, which is highly expressed in mesothelioma and lung, pancreas, breast, ovarian, and other cancers. Encouragingly, recent clinical trials evaluating active immunization or immunoconjugates in patients with pancreatic adenocarcinoma or mesothelioma have shown responses without toxicity. Altogether, these findings and preclinical CAR therapy models using either systemic or regional T-cell delivery argue favorably for mesothelin CAR therapy in multiple solid tumors.

Given the potential high efficiency of CAR therapy, it is critical to identify appropriate antigens to tackle solid tumors, in order to achieve tumor eradication with minimal or tolerable on-target/off-tumor toxicity to healthy tissues.

Solid tumor CAR targets under investigation are altered gene products mostly arising from genetic mutations or altered splicing (EGFRvIII), altered glycosylation patterns (MUC1), cancer-testis antigen-derived peptides (MAGE), overexpressed differentiation antigens CEA, PSMA, GD2, MUC16, HER2/ERBB2, and mesothelin (MSLN), or tumor-associated stroma (FAP and VEGFR).

Although overexpressed antigens are numerous and relatively frequent, they raise concerns about "on-target/off-tumor" side effects due to the high sensitivity of T cells for low-level antigen expression, which can be greater than that of monoclonal antibodies. For instance, the use of ERBB2 CAR T cells, administered at a high cell dose, has resulted in a fatal adverse event, attributed in part to low-level ERBB2 expression in healthy lung epithelial and cardiovascular cells [Morgan, R. A. et al. (2010) Case report of a serious adverse event following the administration of T cells transduced with a chimeric antigen receptor recognizing ERBB2. *Mol Ther.* 18:843-51]. Thus, an optimal solid-tumor antigen target is one whose expression either is restricted to tumor cells or occurs only at very low levels in expendable normal tissues.

MSLN has emerged as an attractive target for cancer immunotherapy, considering its low expression on normal mesothelial cells and high expression in a broad spectrum of solid tumors. The MSLN-targeted immunotherapies reported to date support a favorable safety profile. MSLN is a potential CAR target in a number of common solid tumors, such as at least oesophageal cancer, breast cancer, gastric cancer, cholangiocarcinoma, pancreatic cancer, colon cancer, Lung cancer, Thymic carcinoma, mesothelioma, ovarian cancer, and endometrial cancer [Morello, A. et al. (2016) Mesothelin-Targeted CARs: Driving T Cells to Solid Tumors. *Cancer Discov.* 6(2); 133-46].

MSLN is a glycoprotein anchored to the plasma membrane by a glycophosphatidyl inositol (GPI) domain. It is initially synthesized as a 69 kDa cell-surface protein. After cleavage of the amino terminus by the furin protease, a 40-kDa C-terminal fragment remains attached to the membrane and a soluble 32-kDa N-terminal fragment, named megakaryotic-potentiating factor (MPF), is released [Pastan, I., Hassan, R. (2014) Discovery of mesothelin and exploiting it as a target for immunotherapy. *Cancer. Res.* 74:2907-12]. A soluble form of MSLN has also been detected in the sera of patients with solid tumors, which is referred to as soluble MSLN-related protein (SMRP). SMRP is generated either by alternative splicing or by proteolytic cleavage of the MSLN mature form, induced by the TNFα-converting enzyme ADAM17.

The biologic function of MSLN seems to be nonessential in normal tissues, given that MSLN knockout mice exhibit normal development, reproduction, and blood cell count. In contrast, preclinical and clinical studies increasingly show that aberrant MSLN expression plays an active role in both malignant transformation of tumors and tumor aggressiveness by promoting cancer cell proliferation, contributing to local invasion and metastasis, and conferring resistance to apoptosis induced by cytotoxic agents. MSLN can act bidirectionally, either by directly activating intracellular pathways via its GPI domain or by interacting with its receptor, CA125/MUC16. Overexpression of MSLN alone is sufficient to constitutively activate the NFκB, MAPK, and PI3K intracellular pathways promoting cell proliferation and resistance to apoptosis.

Physiologically, MSLN is expressed on mesothelial cells of the peritoneal and pleural cavities and pericardium; it is expressed minimally on the epithelial cell surface of the trachea, ovaries, rete testis, tonsils, and fallopian tubes. Overexpression of MSLN was initially observed in mesothelioma and ovarian cancer, and subsequently in lung, esophageal, pancreatic, gastric, biliary, endometrial, thymic, colon, and breast cancers. MSLN overexpression thus has an estimated incidence of 340,000 patients and prevalence of 2 million patients a year in the United States alone.

CARs consist of an ectodomain commonly derived from a single-chain variable fragment (scFv), a hinge, a transmembrane domain, and an endodomain (typically comprising signaling domains derived from CD3ζ and costimulatory receptors). Second-generation CARs further enhance T-cell function and persistence through the incorporation of signalling domains that rescue and amplify the activation signal provided by the CD3ζ cytoplasmic domain. Dual signalling prevents T-cell anergy and increases persistence and function by augmenting T-cell proliferation and cytokine production (IFNγ and IL2) and reducing activation-induced cell death through the recruitment of the PI3K, TRAF, and/or other pathways. Third-generation CARs comprise three signalling domains, typically encompassing those of CD3ζ and two co-stimulatory domains, for example CD28 and 4-1BB or CD28 and OX40. Compared with second-generation CARs, third-generation CARs have shown inconsistent antitumor activity in vivo. Choosing an appropriate co-stimulation domain is essential to sustain CAR T-cell activity and calibrate T-cell persistence. However, the ideal co-stimulation domain may depend on context, as CAR function depends on multiple extraneous factors, such as antigen density, CAR stoichiometry, CAR affinity and the immunologic features of the tumor microenvironment.

The spatial distance between CARs and their target antigens may be equally important for effective initiation of T cell signalling, but depends on an entirely different set of structural elements related to the location of the epitope on the target molecule and the spacer domain between the scFv and the T cell membrane. Several studies have demonstrated that the same epitope can activate CAR-T cells with greater efficiency when expressed in a more membrane-proximal position than a membrane-distal position. For example, Hombach et al. demonstrated that CAR T cells recognizing the membrane-distal "N" epitope of the carcinoembryonic antigen (CEA) were only modestly activated; however, when they engineered recombinant CEA protein to express the N epitope in a membrane-proximal position, the same CAR T cells were activated more efficiently [Hombach A A, et al. (2007) T cell activation by antibody-like immunoreceptors: the position of the binding epitope within the target molecule determines the efficiency of activation of redirected T cells. *J Immunol.* 178:4650-4657]. This suggests that targeting some membrane distal epitopes on tumor cells may permit large phosphatases like CD45 and CD148 to enter the synapse and inhibit phosphorylation events initiated by CAR engagement. Tailoring the extracellular spacer sequence between the T cell membrane and the ligand-binding scFv to promote synapse formation can assist in overcoming steric constraints imposed by the location of the target epitope.

A particular concern regarding MSLN CARs is interference from soluble MSLN, which in principle could occupy and block the scFv portion. However, MSLN CAR T-cell activation (cytokine secretion and cytotoxic activity) seems to remain dependent on MSLN expression on the cell surface [Carpenito C., et al. (2009) Control of large, established tumor xenografts with genetically retargeted human T cells containing CD28 and CD137 domains. *PNAS.* 106: 3360-5].

The principle that T cells that are genetically modified to express novel synthetic CARs can effectively treat advanced refractory cancers has been established but many questions remain to realize the full potential of this new therapeutic modality. Engineering safer, more effective CARs for solid tumor cancer therapy requires moving beyond the traditional empiric approach to receptor design and cell engineering, ideally guided by our knowledge of TCR signaling, T cell biology, and manipulation of the tumor microenvironment. It is now apparent that binding affinity, Kon/Koff rates, and spatial constraints between CARs and target cells can influence the ability of CARs to optimally activate T cells for tumor recognition, particularly against solid tumors [D'Aloia, M. M., Zizzari, I. G., Sacchetti, B. et al. (2018) CAR-T cells: the long and winding road to solid tumors. *Cell Death Dis* 9:282].

In view of the above, screening scFv only for their affinity to MSLN antigens or their ability in-vitro to induce T cell activation and proliferation does not appear sufficient to engineer most appropriate CAR T-cells. Current data suggests that optimal CAR affinity cannot be determined a priori for individual target molecules as at this date there is no unbiased approach to identify the ideal affinity range permitting to obtain the best results in vivo [Srivastava, S. and Ridell, R. S. (2015) Engineering CAR-T Cells: Design Concepts. *Trends Immunol.* 36(8): 494-502].

In addition, solid-tumor microenvironment poses several obstacles for MSLN CAR-T cells that may limit their antitumor efficacy. To optimize the efficiency of CAR T cells, numerous approaches are under evaluation to tame the host tumor microenvironment or generate "armored" CAR T cells that can overcome immune barriers. Such strategies include (i) promoting CAR T-cell infiltration, (ii) augmenting the functional persistence of CAR T cells, (iii) enhancing CAR T cells to overcome inhibitory signals encountered in the tumor microenvironment, and (iv) improving safety by preventing on-target/off-tumor toxicity. Among these approaches, combining specific CAR structures with gene edited cells appear to be most promising. Riese et al. [Riese M. J., et al. Enhanced effector responses in activated CD8+ T cells deficient in diacylglycerol kinases. Cancer Res. 73:3566-77] demonstrated for instance that genetic deletion of DGKζ significantly increased the antitumor activity of MSLN CAR T cells, as shown by the enhancement of effector cytokine secretion, FASL, and TRAIL expression, and the cytotoxic functions in vitro.

On another hand, different strategies to address the risk of on-target/off-tumor toxicity and improve the safety of CAR T-cells have been developed.

One such approach has been to transfect mRNA that encodes MSLN CAR, resulting in transient CAR expression for only a few days. In preclinical models, this approach has shown promise; multiple infusions of mRNA CAR T cells have produced a robust antitumor effect in vivo [Zhao Y, et al. (2010) Multiple injections of electroporated autologous T cells expressing a chimeric antigen receptor mediate regression of human disseminated tumor. *Cancer Res.* 2070:9053-61]. However, transient expression of the CAR may limit the long-term efficacy of the therapy. A clinical trial conducted at the University of Pennsylvania using autologous T cells electroporated with the mRNA encoding for a second-generation MSLN CAR (SS1-4-1BB CAR) has resulted into moderate clinical responses and transient elevation of inflammatory cytokines in the sera, including IL12, IL6, G-CSF, MIP1β, MCP1, IL1RA, and RANTES.

Another approach to increase T-cell safety has been to utilize a suicide gene to eliminate T cells in the event of an emerging adverse event. In such a situation, CAR T cells can be eliminated by drug-induced activation of a suicide gene, such as the herpes simplex thymidine kinase (HSV-TK), gene inducible caspase-9, or EGFRΔ gene.

In a previous patent application WO2016120216, the applicant has developed an alternative system to suicide genes, which consists of inserting an exogenous epitope into the CAR structure to be recognized by a clinically approved antibody, such as Rituximab, which allows to partially or completely deplete CAR positive immune cells infused to patients on demand. One benefit of this approach is that no suicide gene has to be co-expressed into the cell in addition to the CAR. However, the insertion of such epitope can have an influence on the CAR overall structure and can modify the way the scFv interacts with its cognate antigen.

The present invention aims to address all or part of the above limitations by providing safer engineered immune CAR positive cells to target MSLN expressing cells in-vivo, such as solid tumors, with the perspective of being used in allogeneic treatment strategies.

SUMMARY OF THE INVENTION

The present invention primarily concerns mesothelin specific chimeric antigen receptors (CAR) for their expression into immune cells, preferably T-cells, for their therapeutic use against malignant mesothelin expressing cells or tissues.

Such CARs present a structure comprising typically:

- an extracellular ligand binding-domain comprising VH and VL from a monoclonal anti-mesothelin antibody;
- a transmembrane domain; and
- a cytoplasmic domain comprising a CD3 zeta signalling domain and a co-stimulatory domain.

The extracellular ligand binding domain of the CARs according to the present invention preferably comprises one or several scFv segment from the antibody referred to as meso1, and more particularly the CDRs therefrom including SEQ ID NO:3, 4, 5, 6, 7 and/or 8.

According to a preferred aspect, said extracellular ligand binding domain of said CARs comprise:

a variable heavy VH chain comprising CDRs from the antibody meso1 having respectively at least 90% identity with SEQ ID NO:3 (CDRH1-Meso1), SEQ ID NO:4 (CDRH2-meso1) and/or SEQ ID NO:5 (CDRH3-meso1), and a variable heavy VL chain comprising CDRs from the antibody Meso1 having respectively at least 90% identity with SEQ ID NO:6 (CDRL1-meso1), SEQ ID NO:7 (CDRL2-meso1) and/or SEQ ID NO:8 (CDRL3-meso1).

The anti-mesothelin CARs of the invention form exogenous polypeptide sequences, which are expressed by the immune cells for their exposition at the surface of the cells. These are encoded by polynucleotide sequences exogenous (with respect to the immune cell's original genome), preferably inserted at specific genomic loci, such as at the TCR, B2m or PD1 gene loci by using rare-cutting endonucleases.

According to some embodiments, said CARs further comprise additional exogenous polypeptide sequence including epitopes, which can be targeted by clinically approved antibodies for in-vivo depletion or by other ligands for their in-vivo or in-vitro detection or purification. Such additional exogenous polypeptide segment may be specifically recognized by Rituximab, such as that referred to as "R2" in the present specification.

The invention is more particularly drawn to immune cells or populations of immune cells transformed with the anti-mesothelin CARs polynucleotide sequences comprising said polynucleotide sequences and/or expressing polypeptide anti-mesothelin CARs sequences.

Such engineered immune cells, or populations of cells, according to the invention may be further genetically engineered, mutated or gene-edited to improve their therapeutic suitability or potency, such as to improve their persistence or lifespan. According to preferred aspects, the engineered immune cells according to the invention combine the expression of anti-mesothelin CARs sequences with other genetic modifications reducing the expression of their endogenous genes, such as TCR, HLA, and/or B2m genes. TGFbeta receptor According to further preferred aspects, the engineered immune cells can be mutated to improve their CAR-dependent immune activation, in particular by reducing or suppressing the expression of immune checkpoint proteins and/or receptors thereof, such as PD1/PDL1.

According to further preferred aspects, the engineered immune cells can be mutated to improve their CAR-dependent immune activation, in particular by reducing or suppressing TGFbeta signalling pathway.

According to other preferred aspects, further exogenous genetic sequences can also be inserted, co-transfected or co-expressed with the anti-mesothelin CARs of the present invention, in particular inhibitors or decoy of TGFbeta receptor, such as a dominant negative TGFbeta receptor (dnTGFβRII).

Further examples of exogenous genetic sequences are provided, which expression can be combined with that of the anti-mesothelin CARs to improve therapeutic potency of immune cells, in particular the following ones:

NK cell inhibitors, such as HLAG, HLAE or ULBP1;

CRS inhibitors, such as a mutated IL6Ra, sGP130 or IL18-BP; or

Cytochrome(s) P450, CYP2D6-1, CYP2D6-2, CYP2C9, CYP3A4, CYP2C19 or CYP1A2, conferring hypersensitivity of said immune cells to a drug, such as cyclophosphamide and/or isophosphamide, Dihydrofolate reductase (DHFR), inosine monophosphate dehydrogenase 2 (IMPDH2), calcineurin or methylguanine transferase (MGMT), mTORmut or Lckmut, conferring drug resistance Chemokine or a cytokine, such as IL-2, IL-12 and IL-15.

secreted inhibitor of Tumor Associated Macrophages (TAM), such as a CCR2/CCL2 neutralization agent, to enhance the therapeutic activity of the immune cells;

The engineered immune cells according to the present invention are particularly suited for treating a condition characterized by mesothelin expressing cells, in particular solid tumors, such as typically: oesophageal cancer, breast cancer, gastric cancer, cholangiocarcinoma, pancreatic cancer, colon cancer, lung cancer, thymic carcinoma, mesothelioma, ovarian cancer and/or endometrial cancer.

The invention thus encompasses methods for producing engineered cells, the resulting therapeutic cells, populations of cells comprising such cells and therapeutic compositions comprising same, as well as the methods of treatment allowing to address pathologies induced by mesothelin expressing cells.

BRIEF DESCRIPTION OF THE FIGURES AND TABLES

FIG. 1: Structural representation of preferred versions of anti-mesothelin CAR according to the invention. A: CAR comprising: V1 and V2 representing sequences comprising ScFv specifically binding mesothelin, such as VH and VL or VL and VH from meso1 antibody; L: linker; R1 and R2 representing exogenous epitopes such as CD20 epitopes recognized by human approved monoclonal anti CD20 antibodies (e.g.: rituximab, . . . ); TM: transmembrane domain; CO-STIM: co-stimulatory domain; ITAMs: stimulatory domain comprising ITAM (Immunoreceptor tyrosine-based activation motif (ITAM). Such CAR has typically at least 80% polypeptide sequence identity with SEQ ID NO:21. B: CAR without exogenous epitopes comprising: VH and VL or VL and VH from meso1 antibody; a (G4S)3 linker; a CD8α hinge domain a CD8α transmembrane domain; a 4-1BB co-stimulatory domain; and a CD3z signaling domain.

Figure 2:
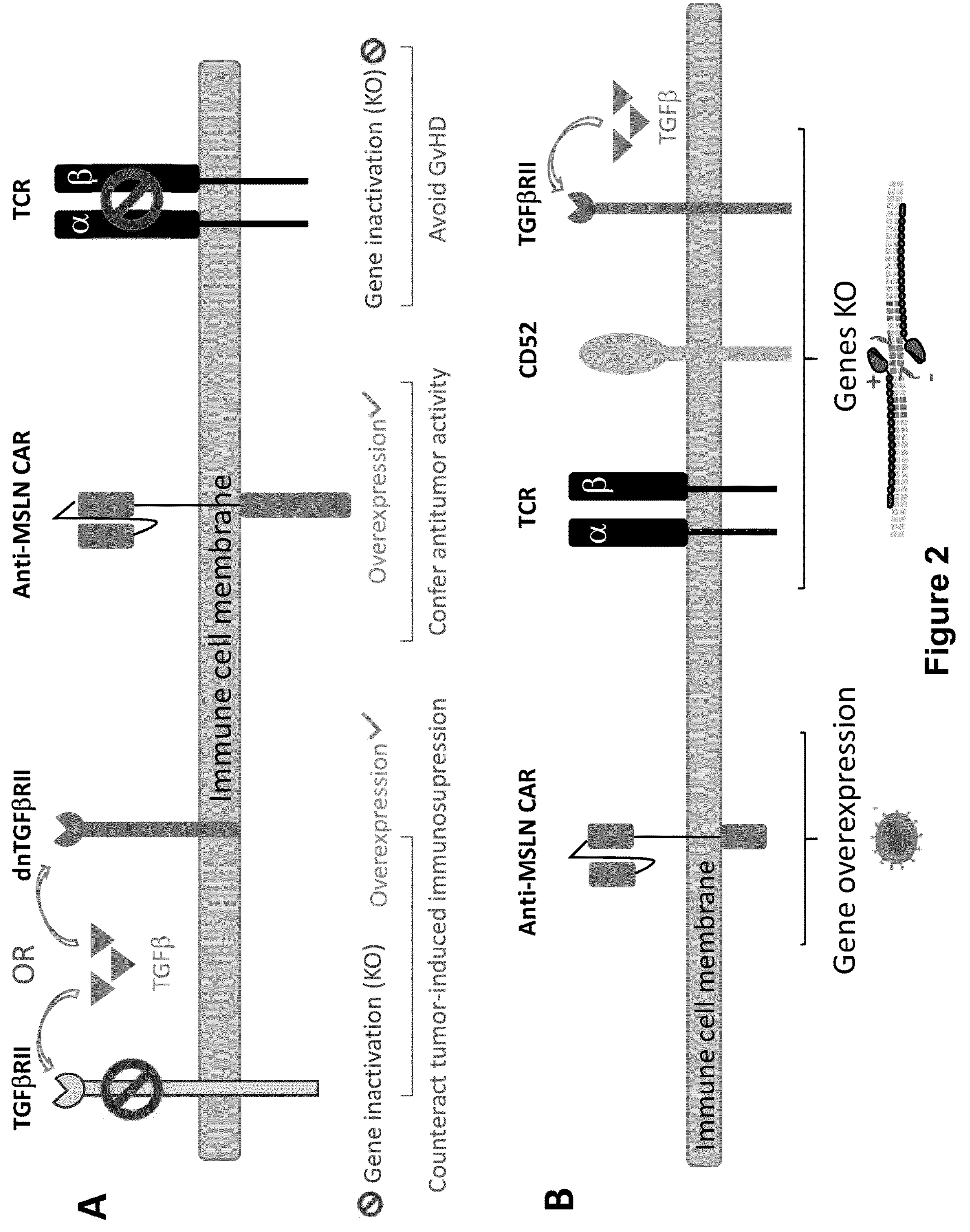

FIG. 2: Schematic representation figuring anti-MSLN CAR expressing immune cells according to the invention, in which optional genetic attributes have been further introduced: A. Co-expression with an inactive variant of TGFβ receptor (e.g.: dnTGFβRII) and/or genetic reduction or inactivation of TGFβ receptor expression to counteract tumor-induced immune suppression. Reduction or inactivation of TCR expression (e.g. TCRalpha) to lower immune T-cells alloreactivity causing GvHD. B. Genetic reduction or inactivation via gene editing tools (such as TALEN) of TGFβ receptor, TCR and/or CD52 expression.

Figure 3:
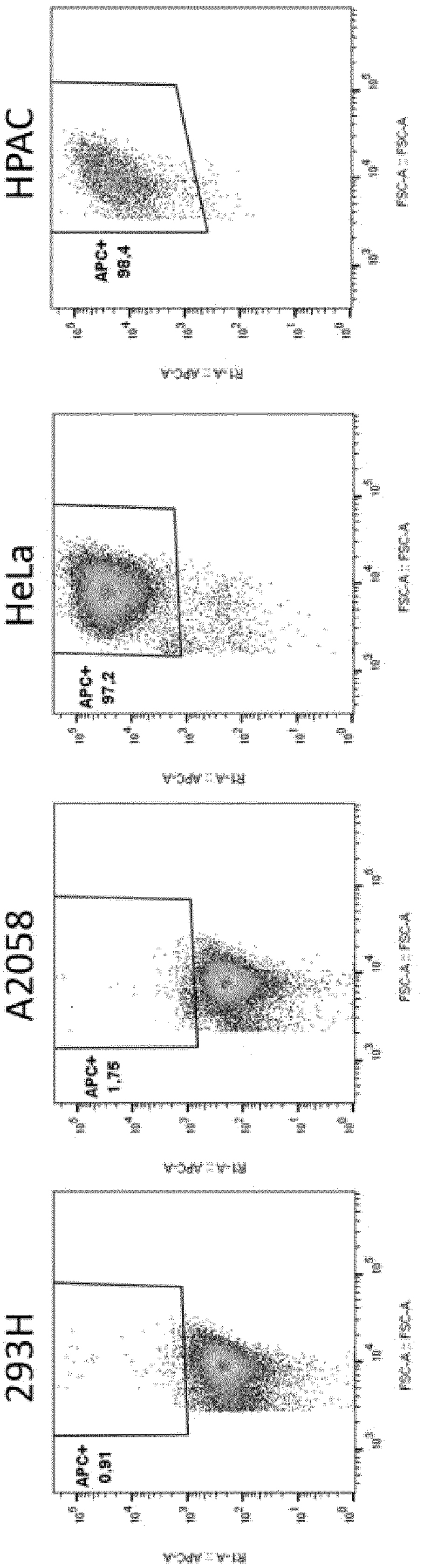

FIG. 3: Mesothelin protein expression at the surface of 293H, A2058, HeLa, and HPAC cells. Analysis of MSLN expression was performed by flow cytometry using a mouse monoclonal anti-human MSLN antibody as primary antibody and the APC-conjugated goat anti-mouse polyclonal antibody as secondary antibody.

Figure 4:
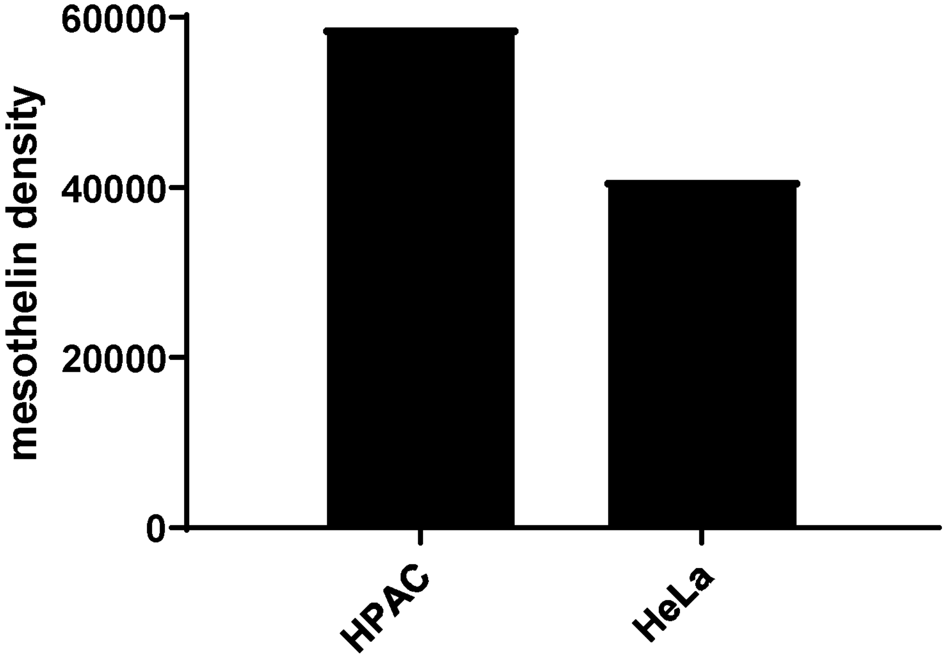

FIG. 4: Quantitative Mesothelin protein expression at the surface of HeLa, and HPAC cells. Analysis of MSLN expression level was performed by flow cytometry using fluorescence-based QIFIKIT.

Figure 5:
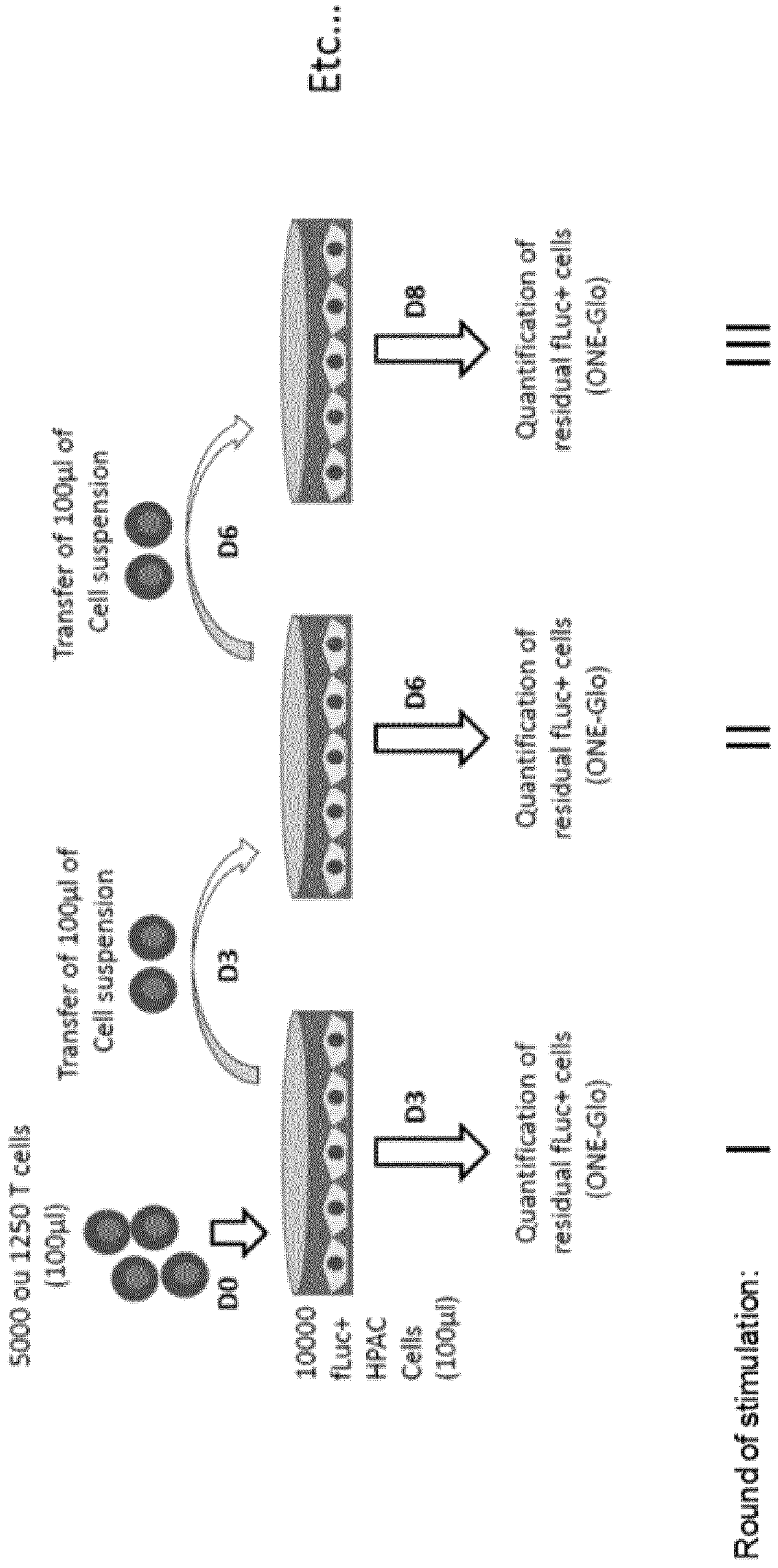

FIG. 5: Figure representing serial killing assay performed to assess in-vitro activation of anti-mesothelin CAR positive cells.

Figure 6:
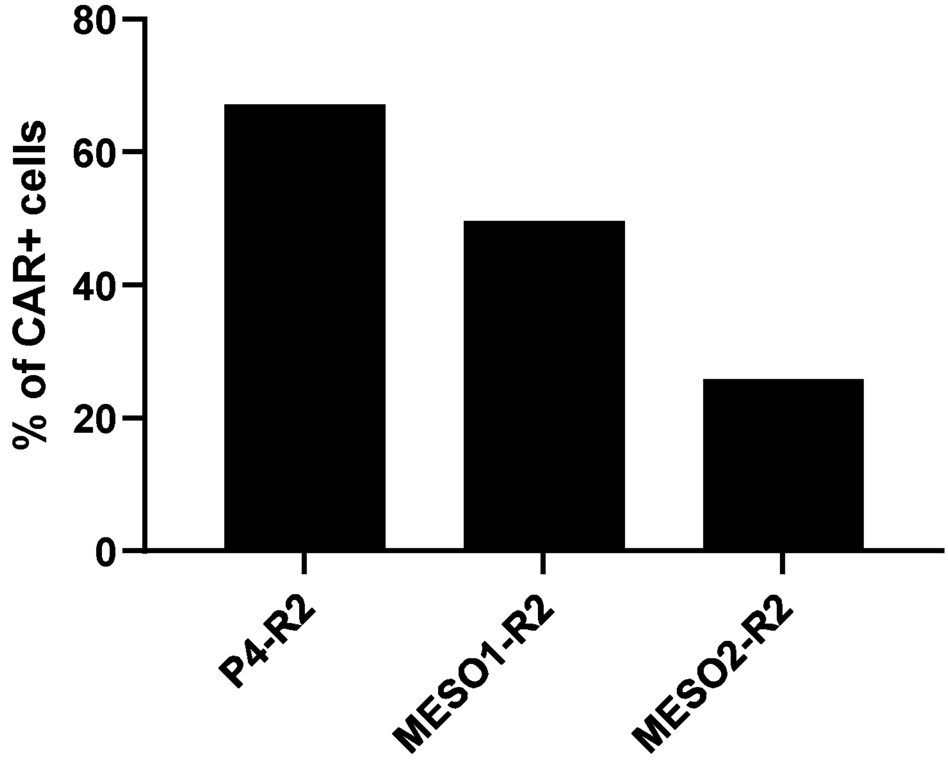

FIG. 6: CAR expression at the surface of primary [TCRalpha]$^{neg}$ T-cells (UCART cells). Cryopreserved UCART cells generated from a single donor were stained with histidine-tagged recombinant human mesothelin protein and PE-conjugated anti-histidine antibody or biotinylated protein L and Vioblue-conjugated streptavidin, and analyzed by flow cytometry.

Figure 7:
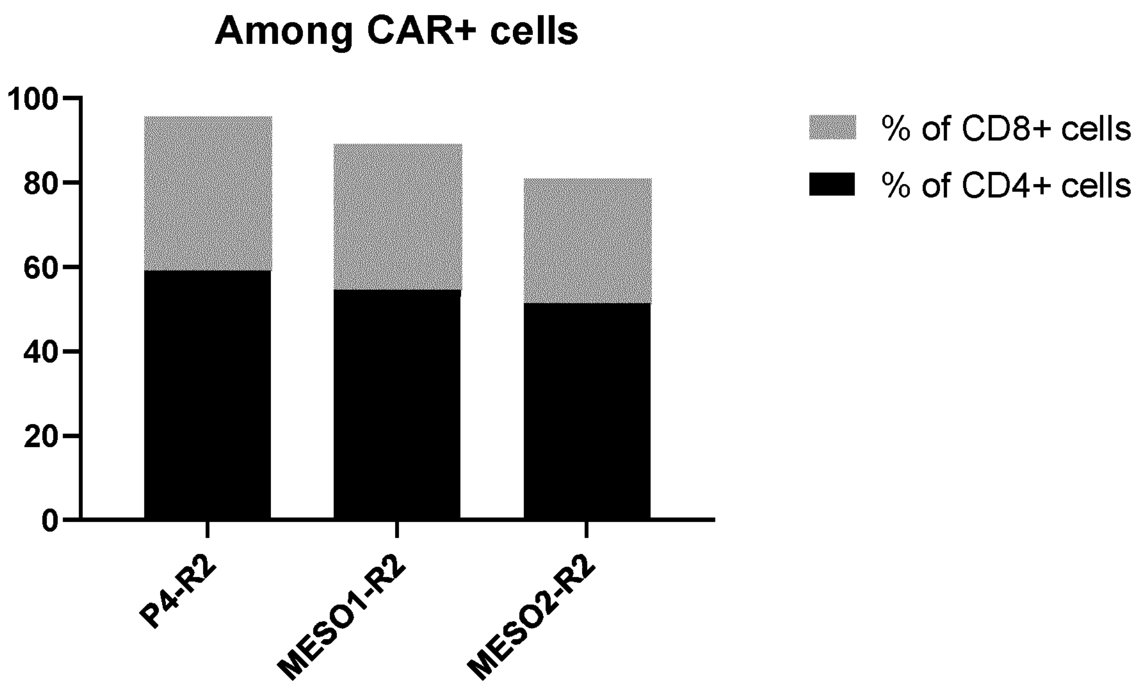

FIG. 7: CD4 and CD8 expression by the CAR+ fraction of UCART cells. Cryopreserved UCART cells generated from a single donor were stained with FITC-conjugated anti-CD4 and BV510-conjugated anti CD8 antibodies and analyzed by flow cytometry.

Figure 8:
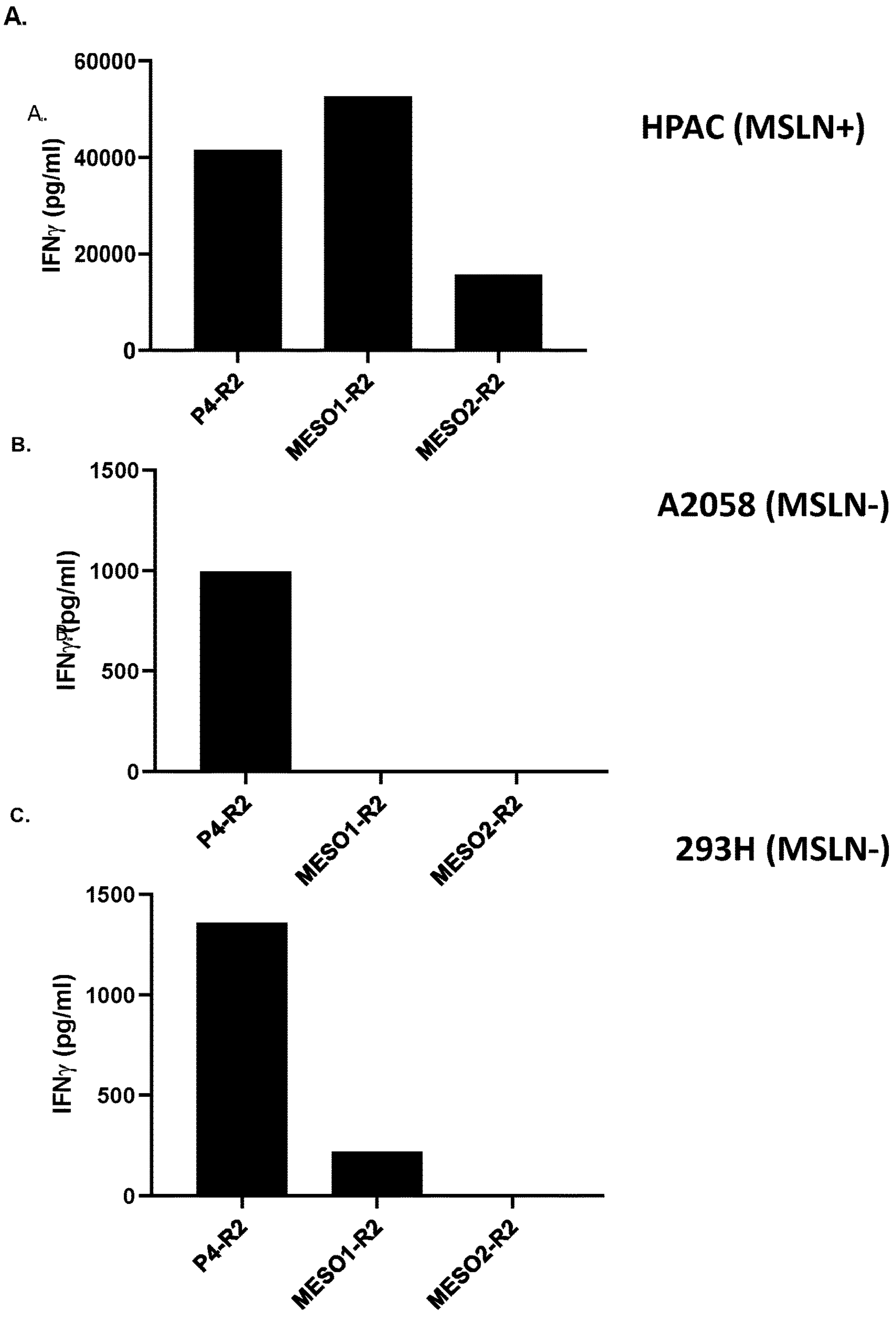

FIG. 8: Production of IFNg by UCART cells. Fresh UCART cells generated from a single donor were cocultured for 24 hours with (A) HPAC (MSLN+) cells, (B) A2058 (MSLN−) cells, and (C) 293H (MSLN−) cells. IFNg produced in the culture supernatants was quantified by ELISA.

Figure 9:
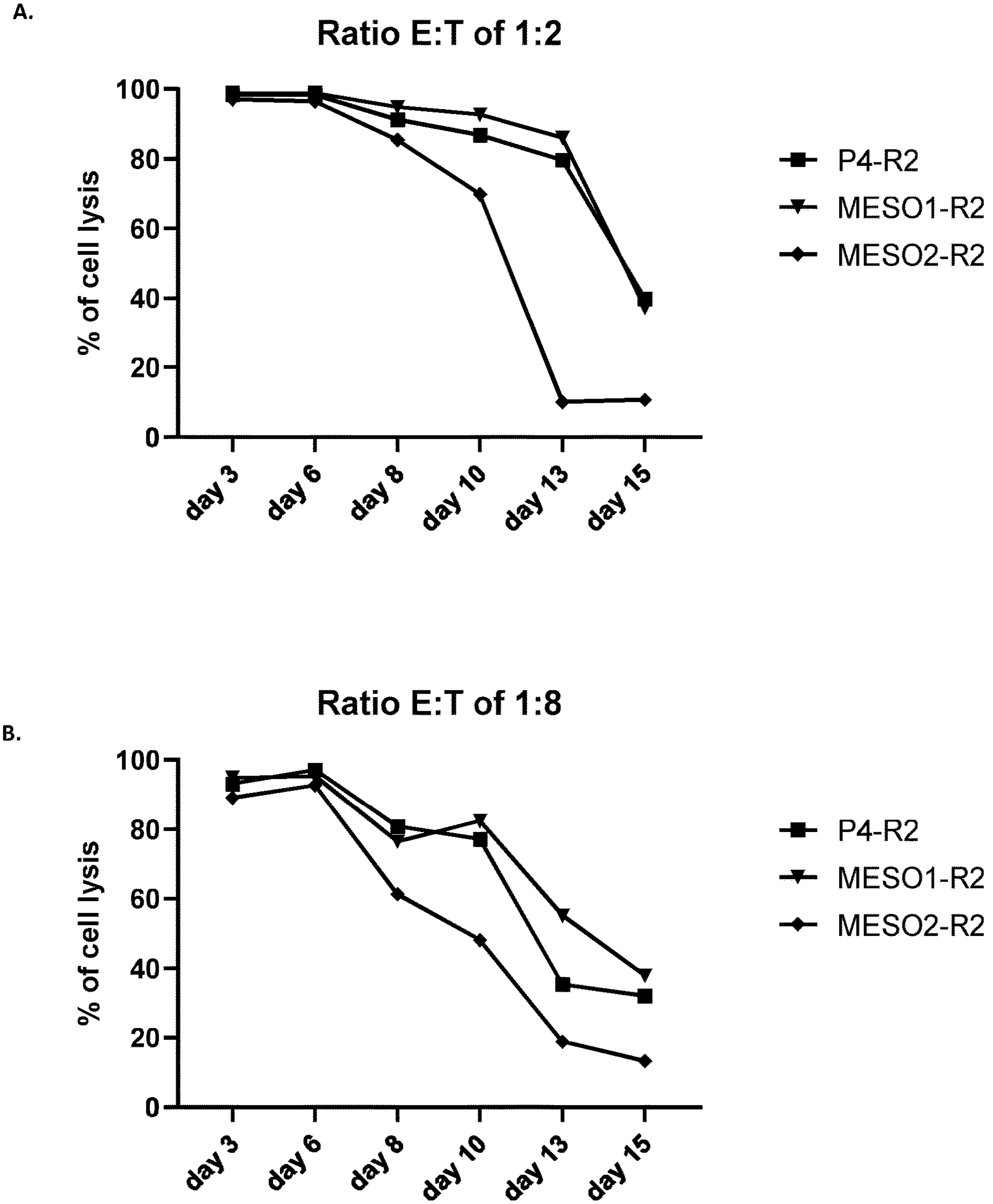

FIG. 9: Graphs showing % cell lysis resulting from the serial killing assay of HPAC cells by primary [TCRalpha]$^{neg}$ T-cells (UCART cells), which protocol is illustrated in FIG. 5. Cryopreserved UCART cells generated from one donor were cocultured for 15 days with HPAC cells at E:T ratios of 1:2 (A) or 1:8 (B).

Figure 10:
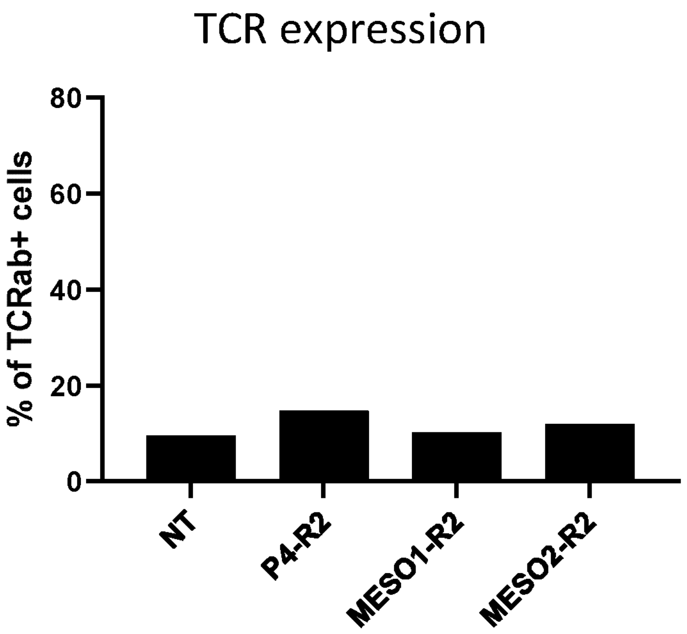

FIG. 10: TCRαβ expression at the UCART cells surface. Cryopreserved UCART cells generated from a single donor were stained with PEvio770-conjugated anti-TCRαβ antibody and analyzed by flow cytometry.

Figure 11:
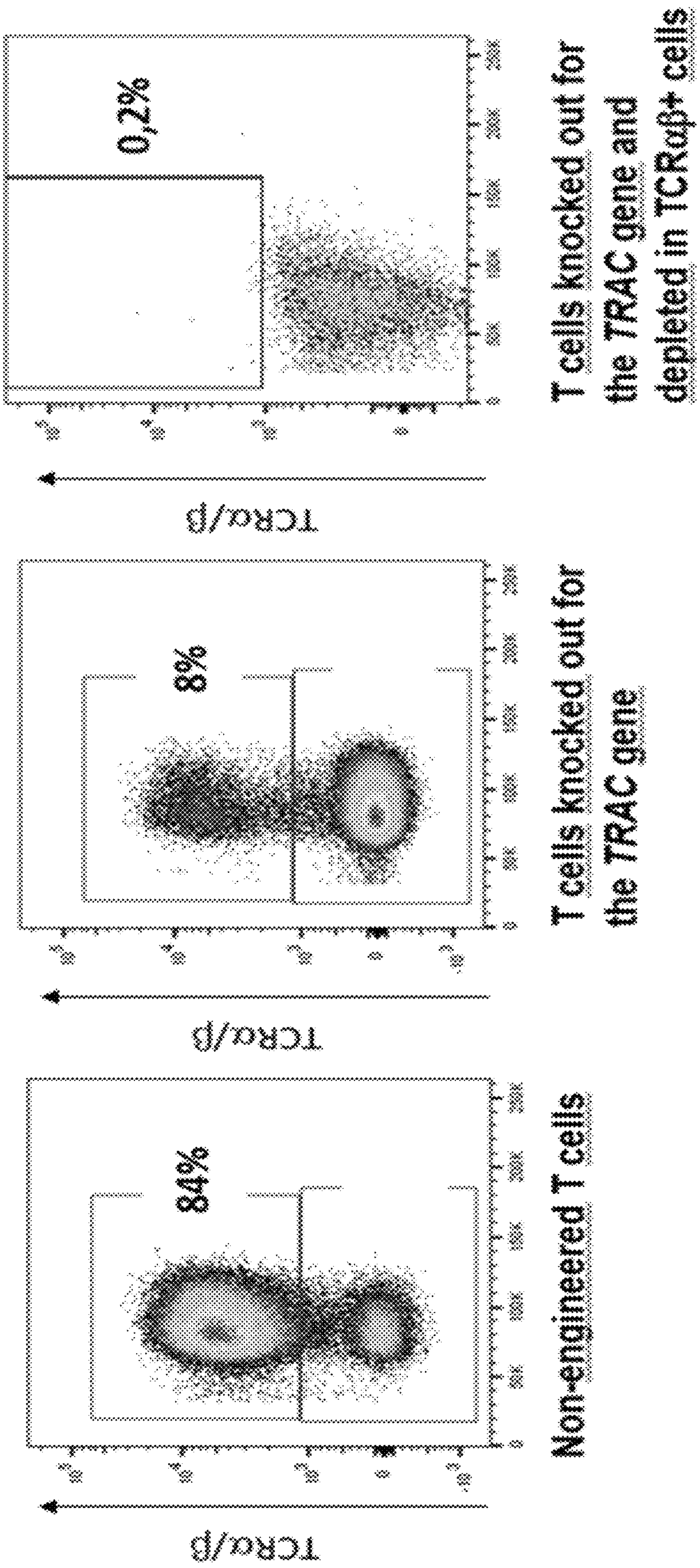

FIG. 11: Flow cytometry analysis of the expression of the TCRαβ receptor at the surface of non-engineered T cells, T cells knocked-out for the TRAC gene, and T cells knocked-out for the TRAC gene and depleted in TCRαβ$^{+}$ cells.

Figure 12:
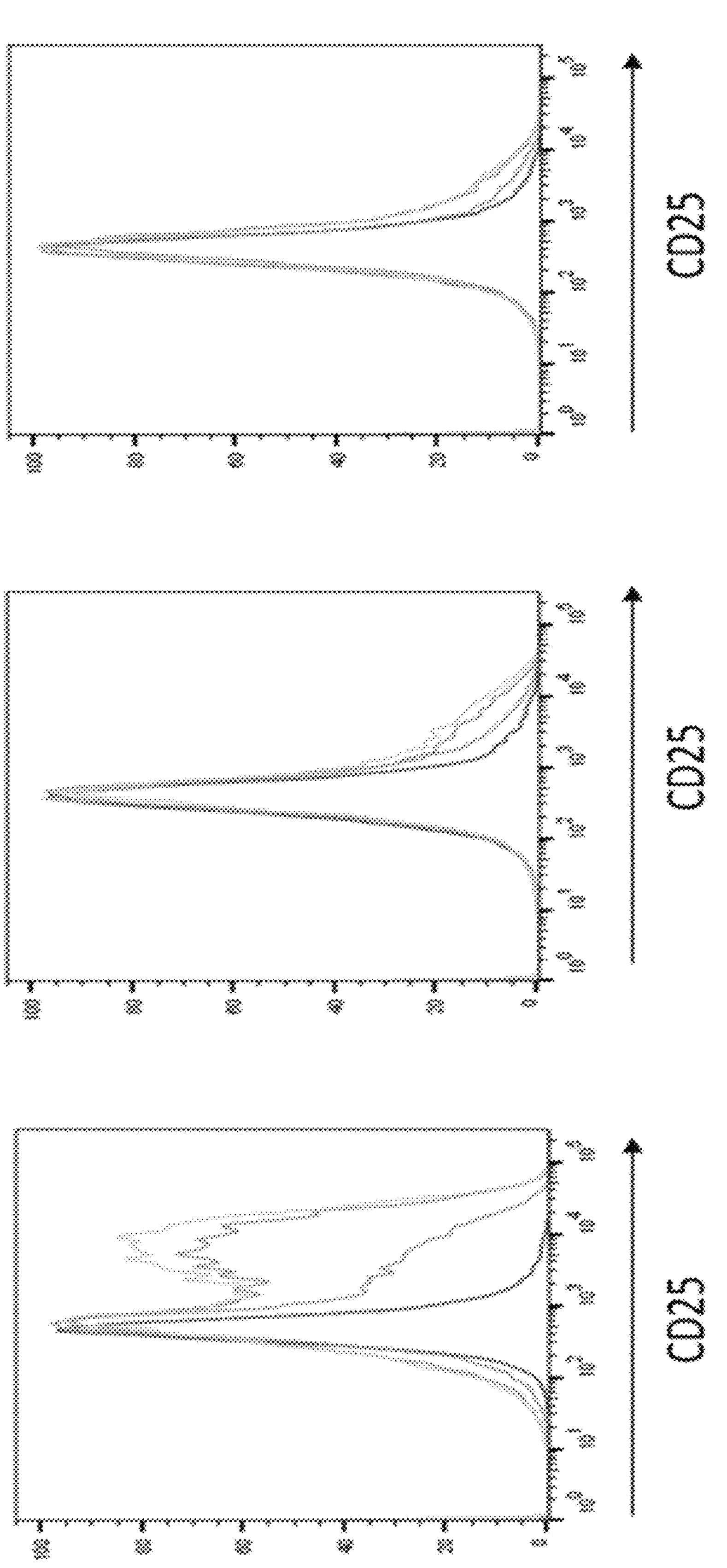

FIG. 12: Flow cytometry analysis of the expression of CD25 at the surface of non-engineered T-cells, T-cells knocked-out for the TRAC gene and T-cells knocked-out for the TRAC gene and depleted in TCRαβ+ cells, upon exposure to medium (red line), +0.1 μg/ml of PHA-L (orange line), +0.25 μg/ml of PHA-L (green line) and +2.5 μg/ml of PHA-E and L (blue line) respectively.

Figure 13:
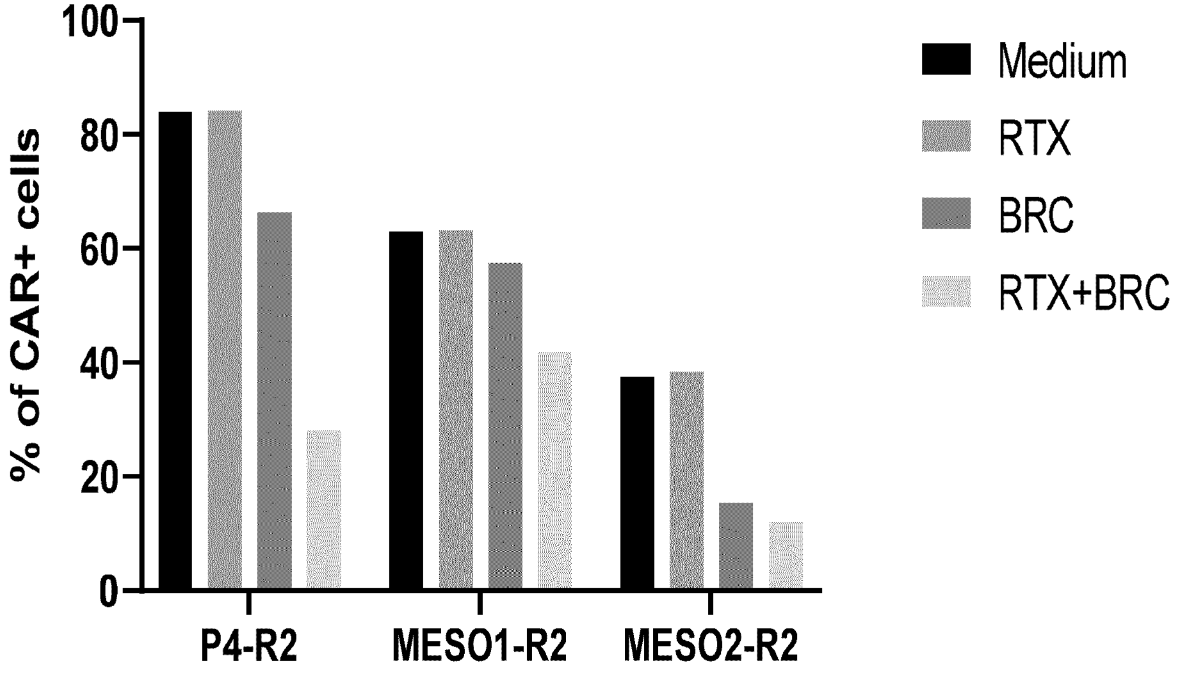

FIG. 13: Measurement of UCART cells depletion by rituximab-mediated CDC through the exogenous epitope polypeptide R2 included into the CARs P4-R2, Meso1-R2 and MESO2-R2.

Figure 14:
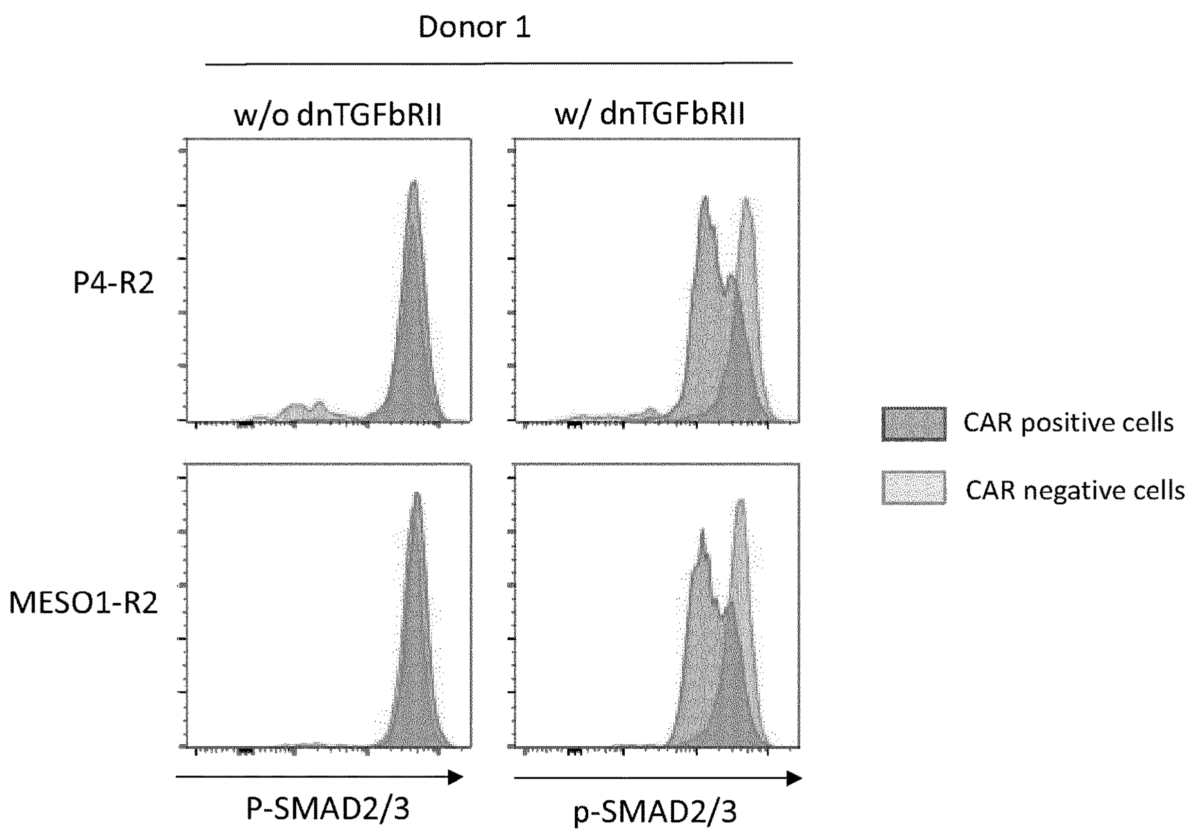
Figure 14:
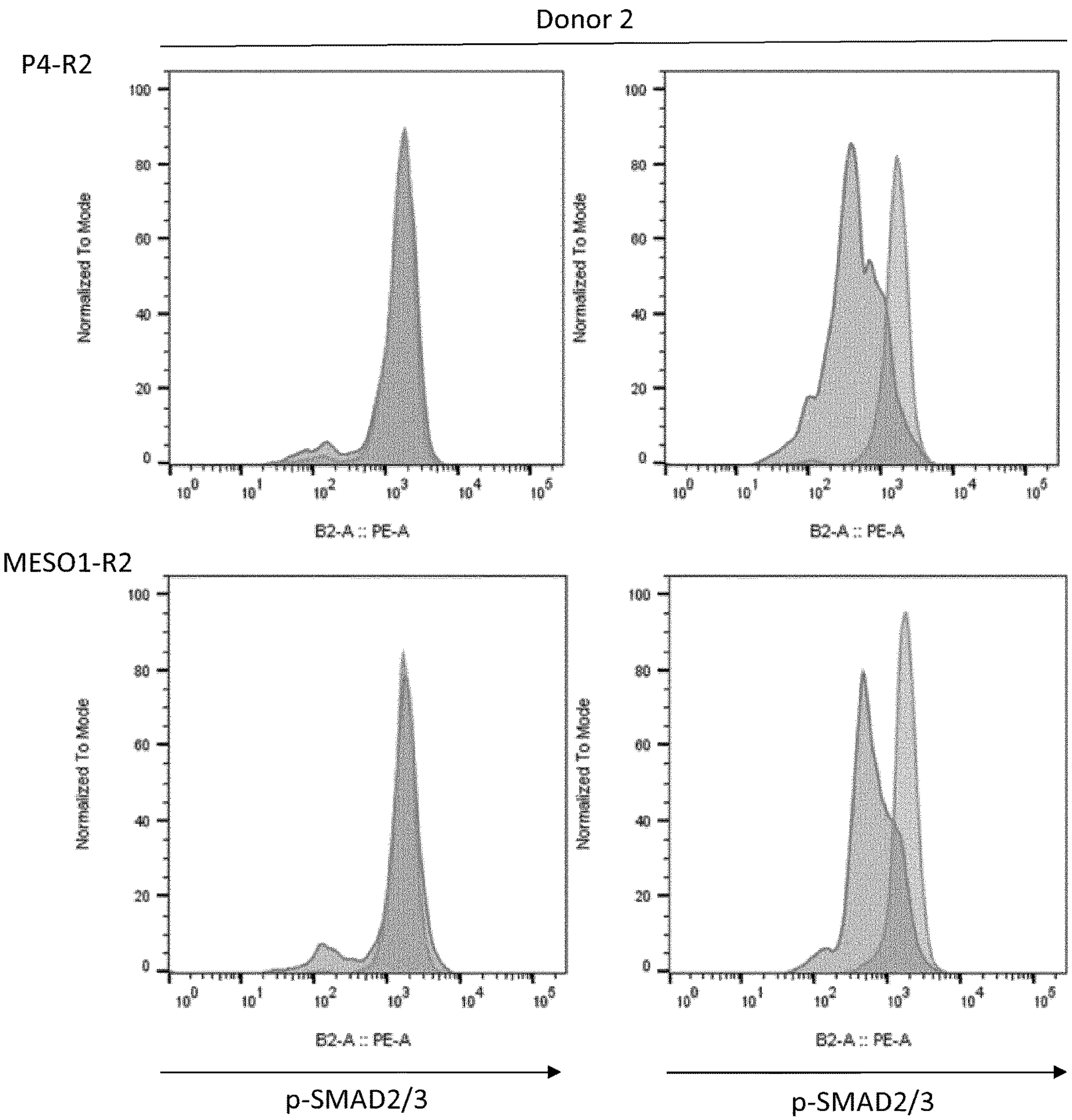

FIG. 14: Graphs displaying measurement of SMAD2-3 phosphorylation upon exposure to TGFβ of CART cells generated from 2 different donors.

Figure 15:
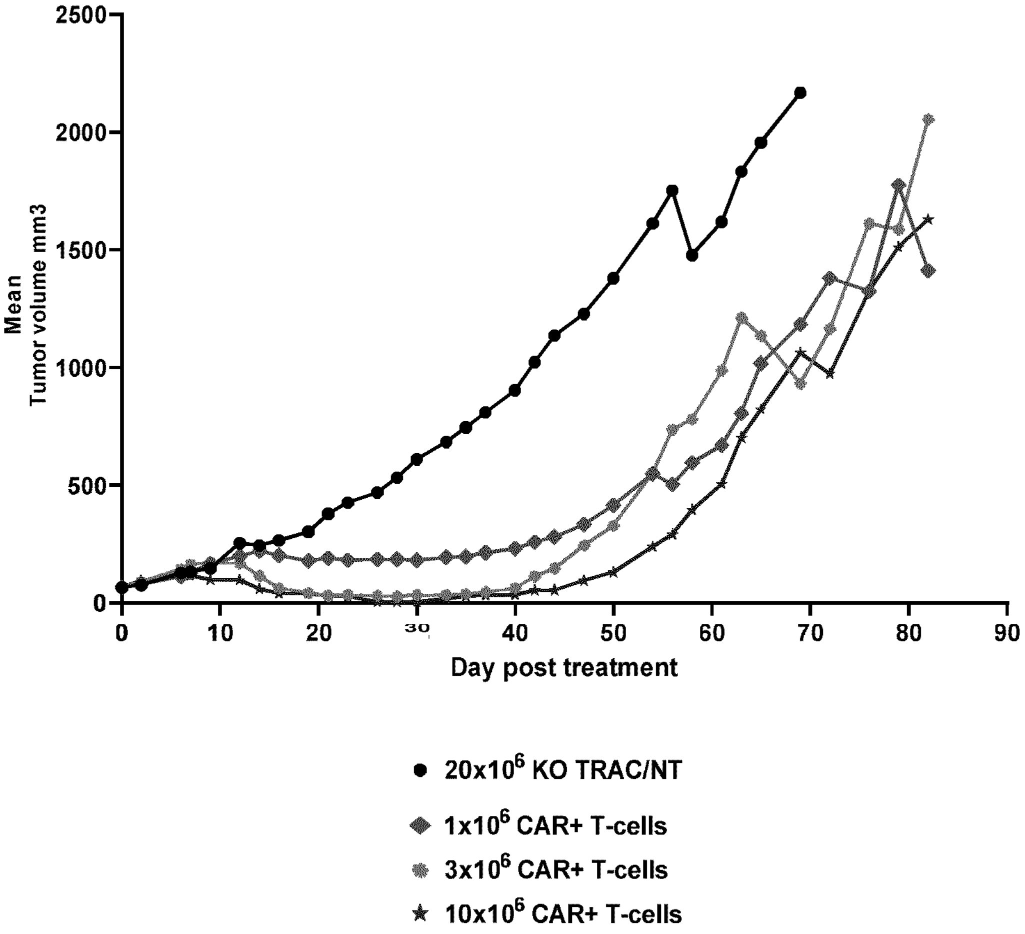

FIG. 15: Mean tumor volume (HPAC MSLN+ cells) in mice injected with UCARTmeso (TCR negative anti-mesolthelin P4-R2 CAR positive cells) at three doses ($1\times10^6$, $3\times10^6$ and $10\times10^6$ CAR+ cells/mouse).

Figure 16:
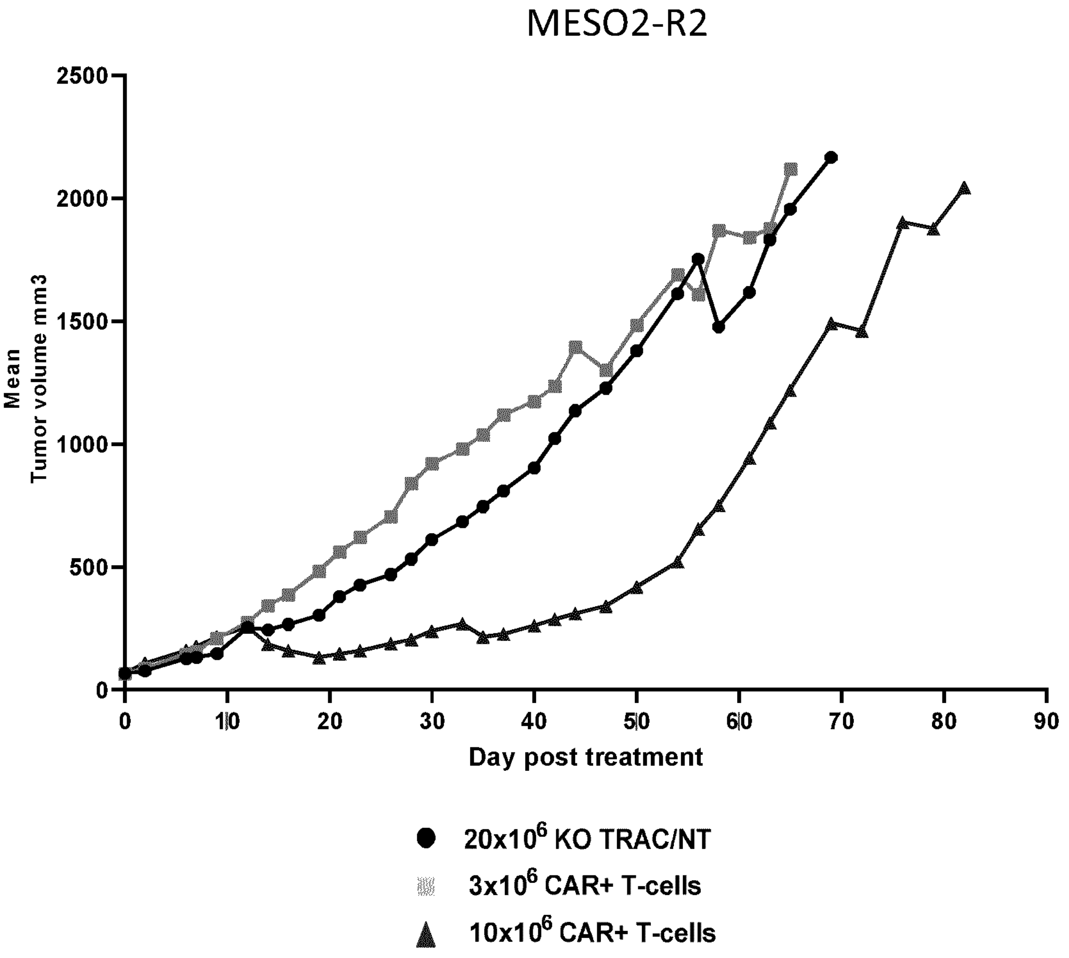

FIG. 16: Mean tumor volume in mice injected with UCARTmeso cells (TCR negative anti-mesolthelin Meso2-R2 CAR positive cells) at three doses ($1\times10^6$, $3\times10^6$ and $10\times10^6$ CAR+ cells/mouse).

Figure 17:
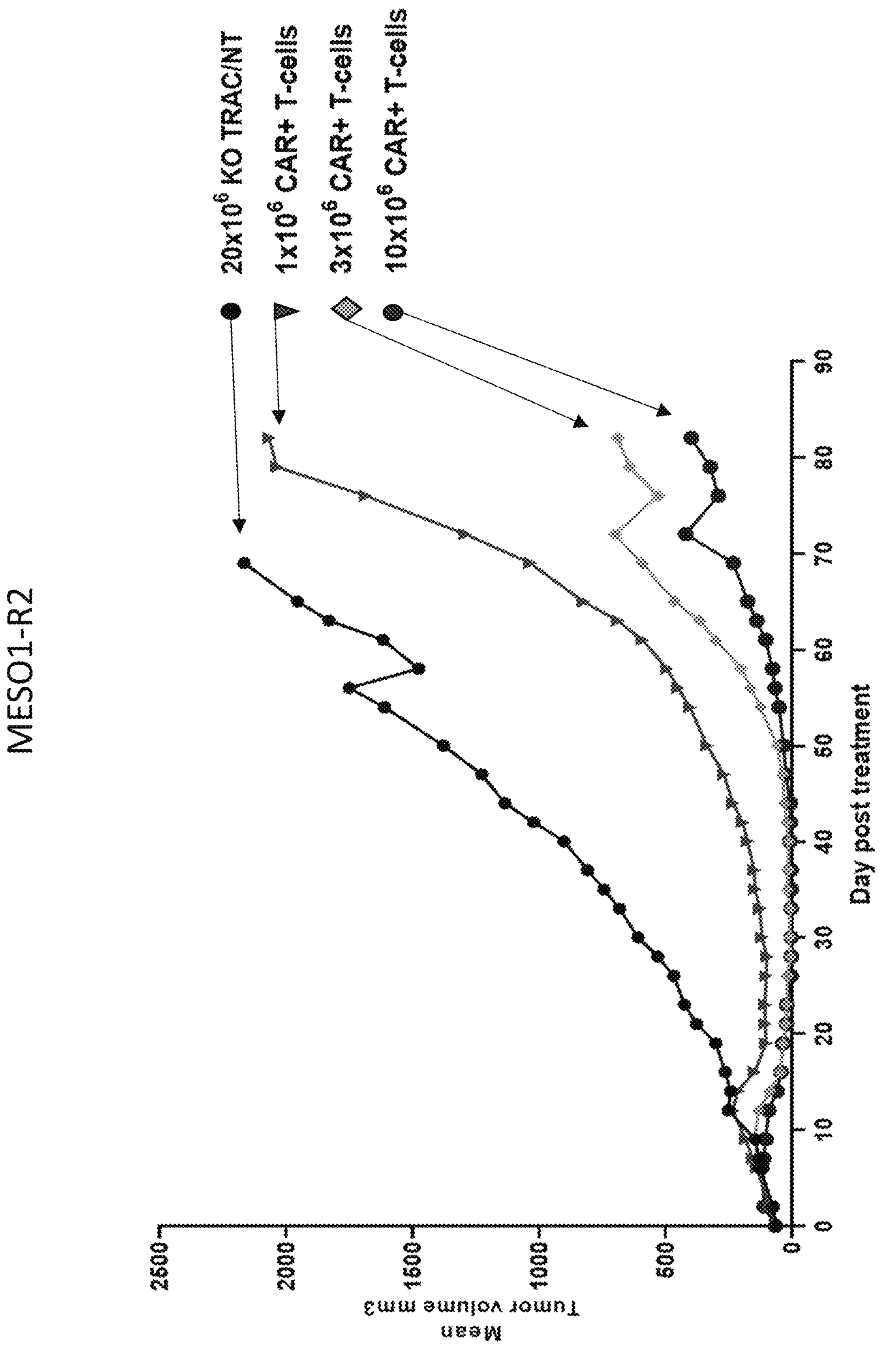

FIG. 17: Mean tumor volume in mice injected with UCARTmeso cells (TCR negative anti-mesolthelin Meso1-R2 CAR positive cells) at three doses ($1\times10^6$, $3\times10^6$ and $10\times10^6$ CAR+ cells/mouse).

Figure 18:
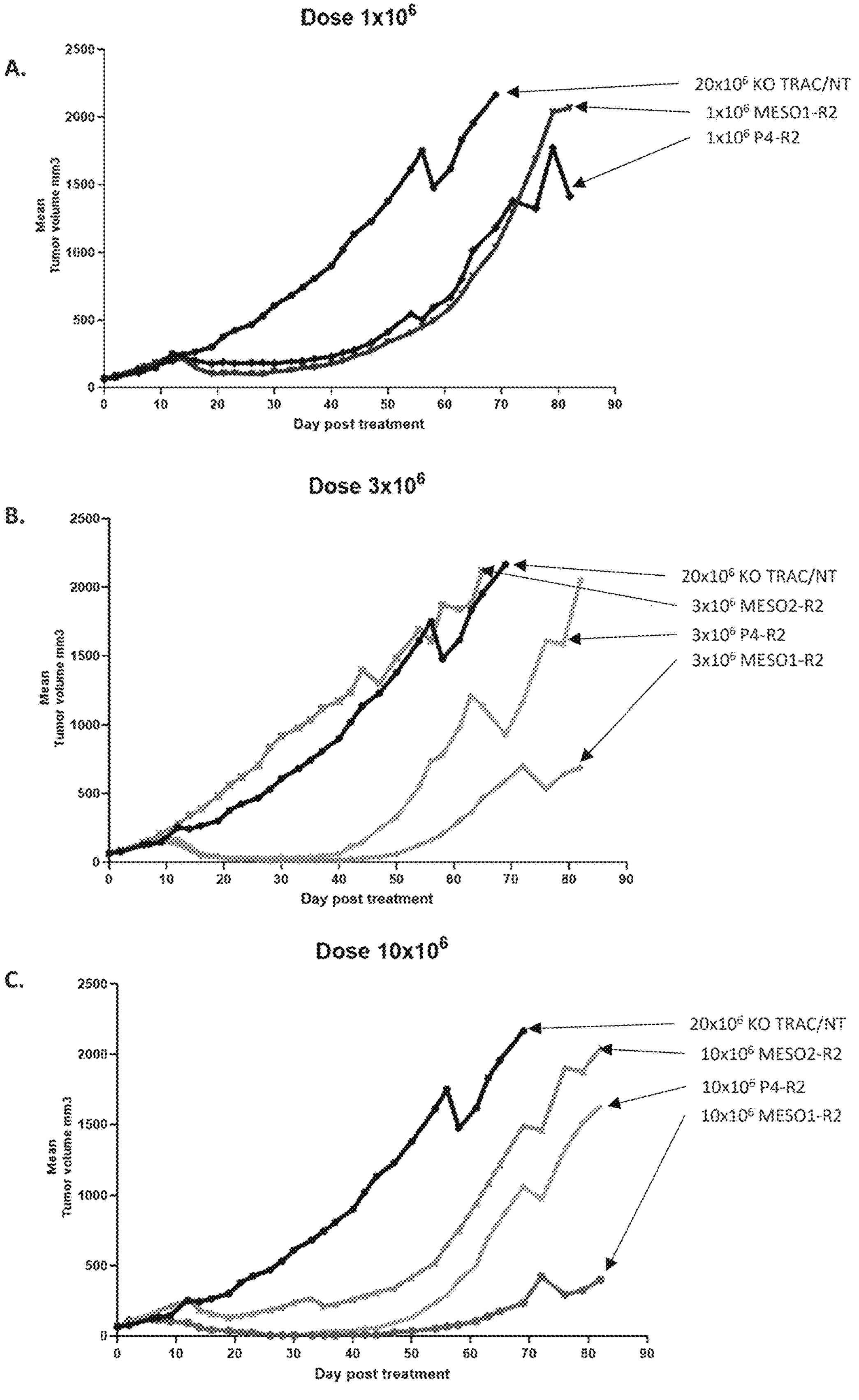

FIG. 18: Mean tumor volume+/−standard deviation in mice injected with UCARTmeso cells at three doses (A: $1\times10^6$, B: $3\times10^6$ and C: $10\times10^6$ CAR+ cells/mouse). Comparison of the different doses for respectively Meso1-R2, P4-R2 and MESO2-R2.

Figure 19:
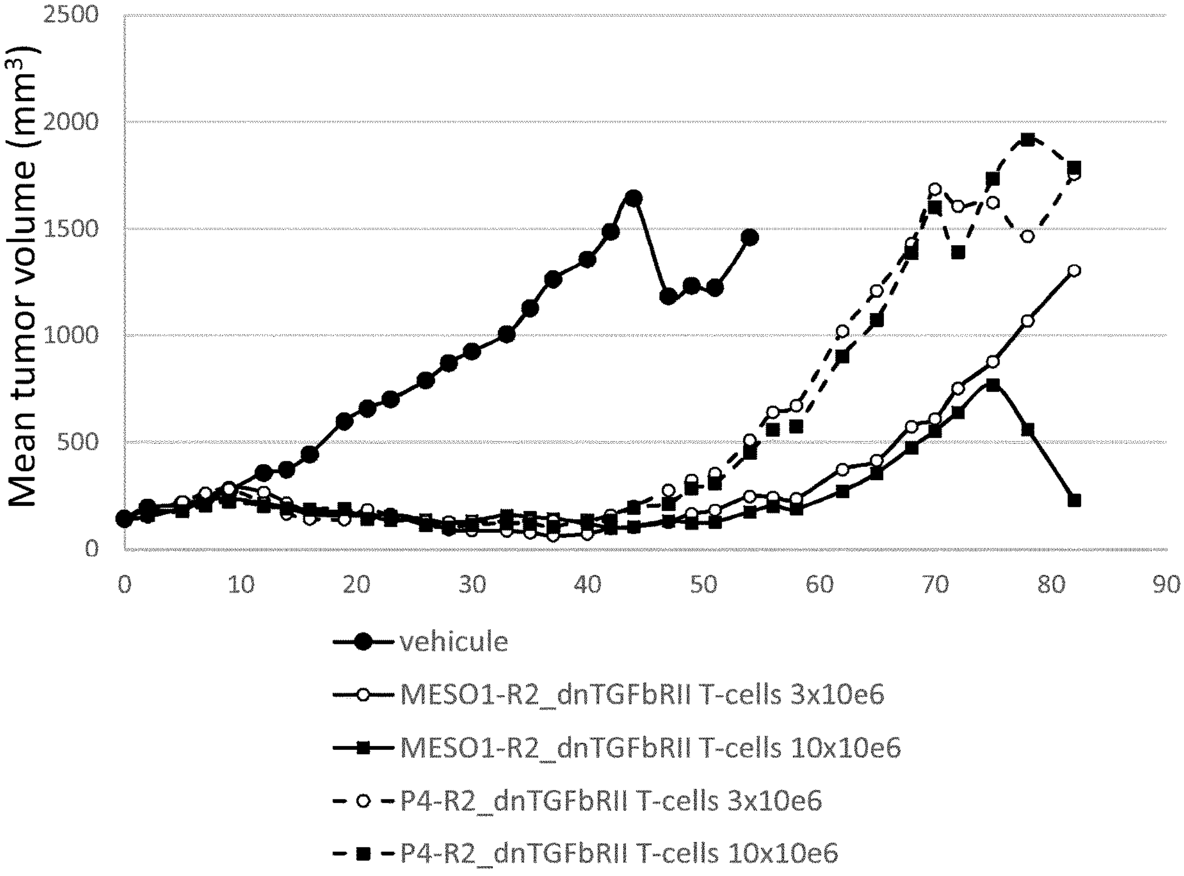

FIG. 19: Mean tumor volume in mice injected with UCARTmeso cells that are also expressing dnTGFBRII at two doses ($3\times10^6$ and $10\times10^6$ CAR+ cells/mouse).

Figure 20:
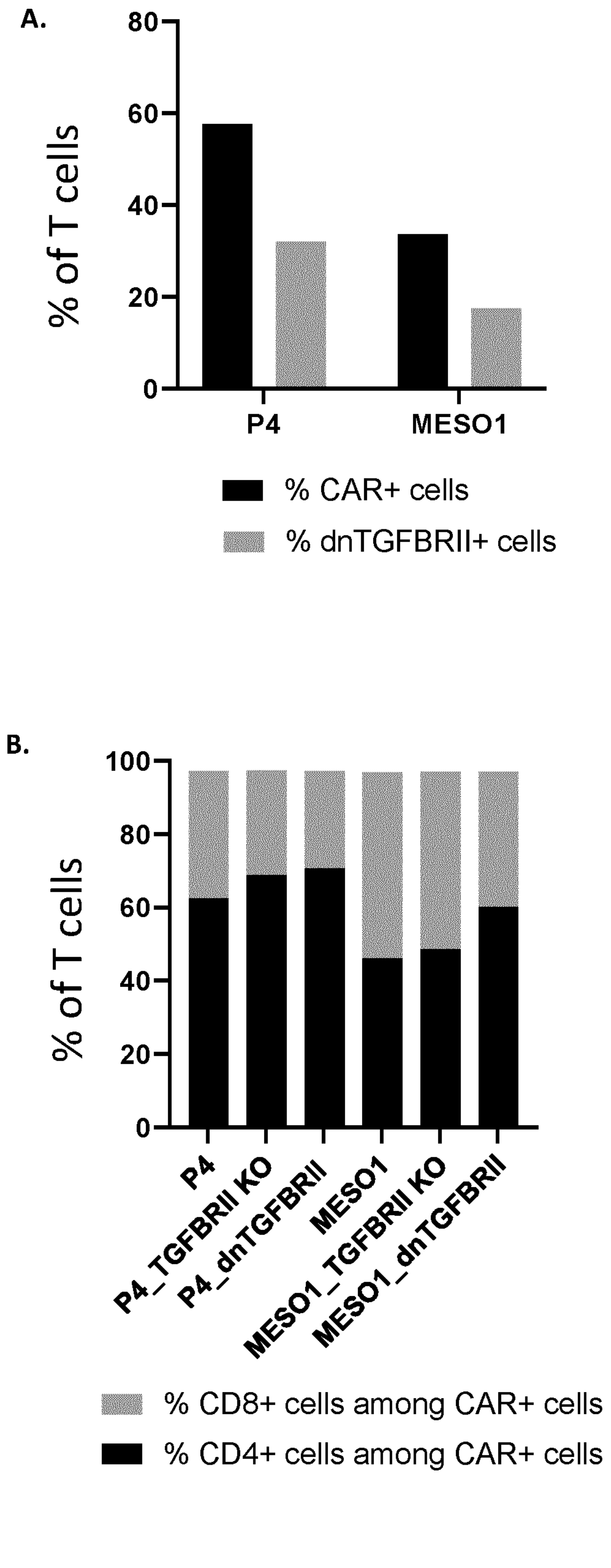

FIG. 20: A. Comparison of CAR and dnTGFBRII detection in UCARTMeso cells expressing P4 or MESO1 constructs with dnTGFBRII. B. Percentage of CD4+ and CD8+ in the CAR positive fraction of UCARTMeso cells produced in example 5.

Figure 21:
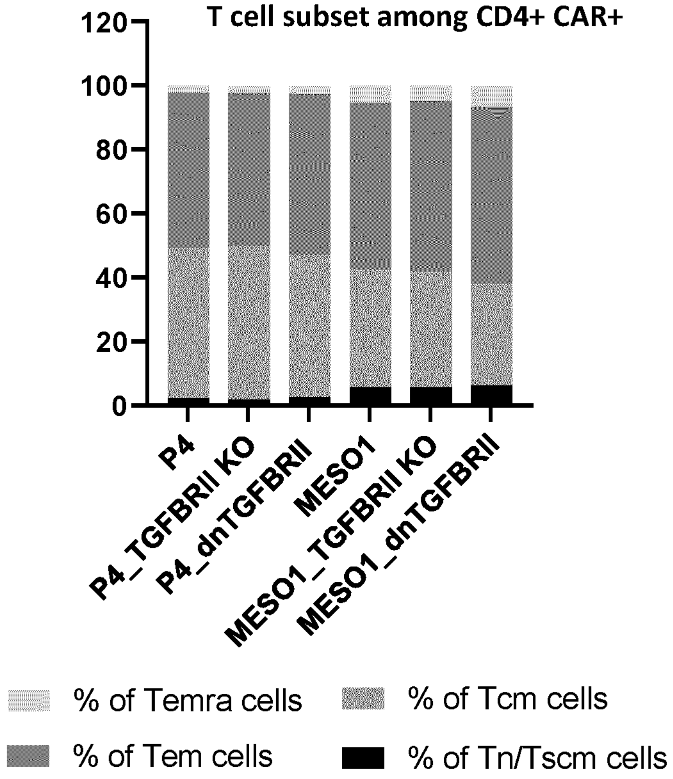
Figure 21:
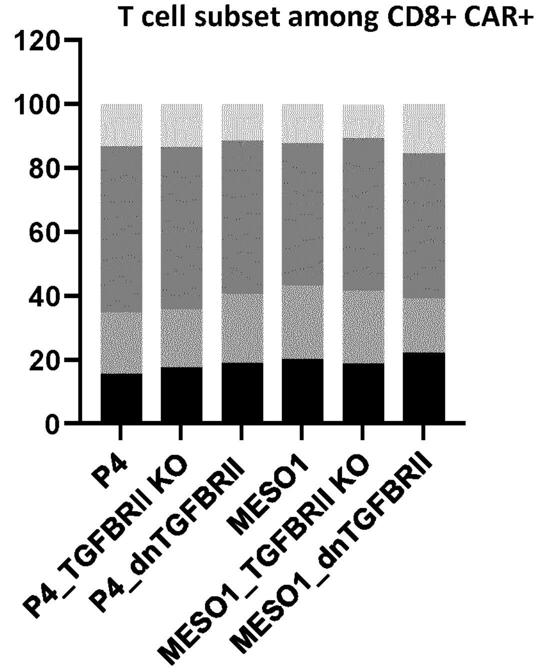

FIG. 21: Percentage of Temra, Tem, Tcm; Tn/scm cells observed in the CAR+CD4+ fraction (A.) or CAR+CD8+ fraction (B.) of UCARTMeso cells produced in example 5.

Figure 22:
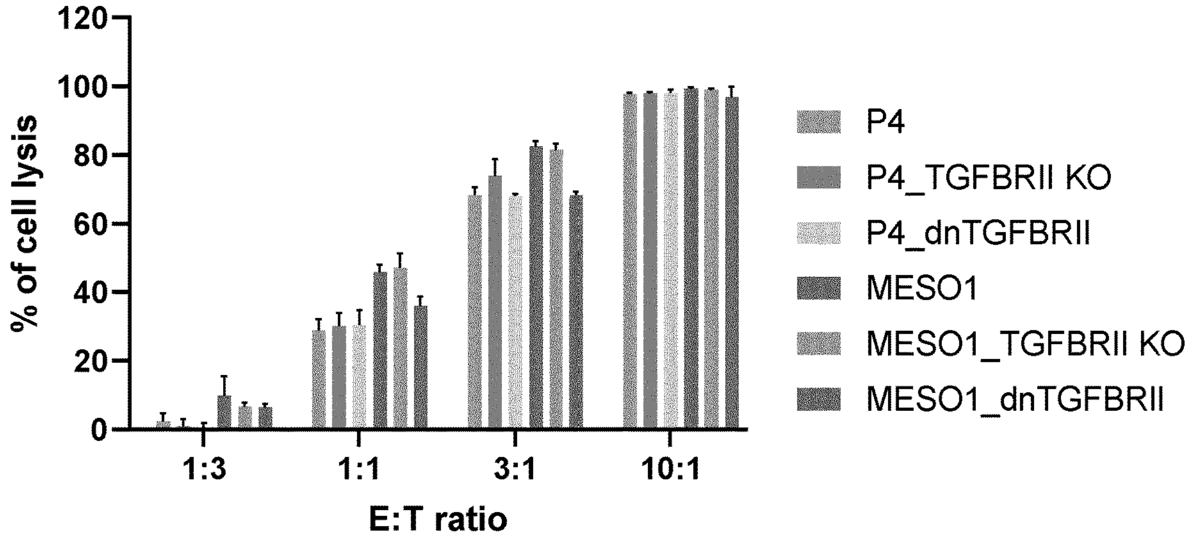

FIG. 22: Percentage of H226 cells killing by different UCARTmeso cells inactivated or not for TGFBRII pathway by Knock-Out (KO) or by expression of dominant negative TGFBRII (dnTGFBRII).

Figure 23:
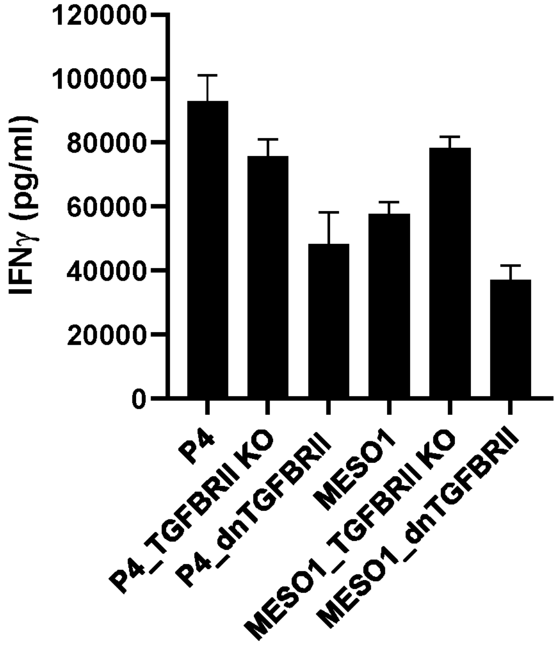
Figure 23:
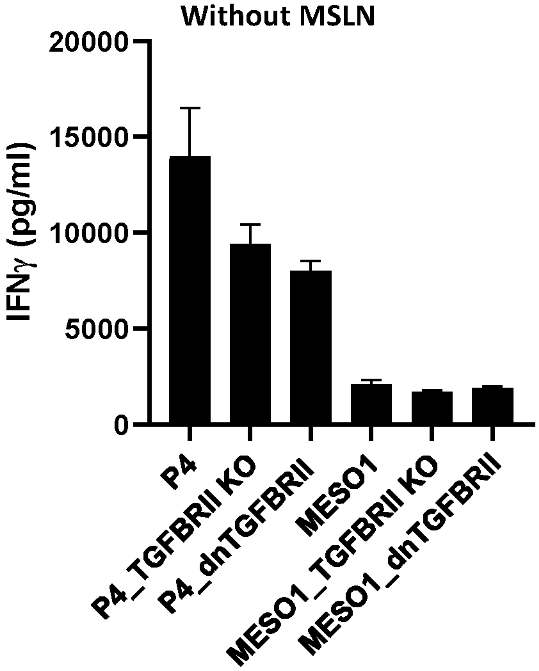

FIG. 23: Production of IFNg by UCARTMeso cells produced in example 5 and exposed (A.) or not (B.) to recombinant Mesothelin protein.

Figure 24:
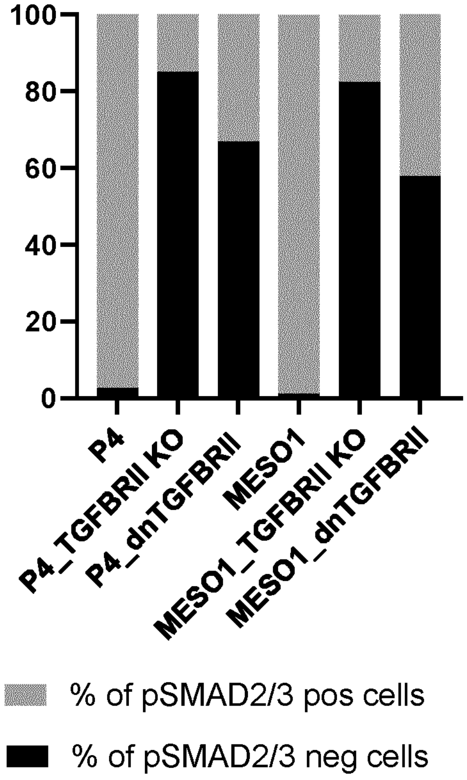
Figure 24:
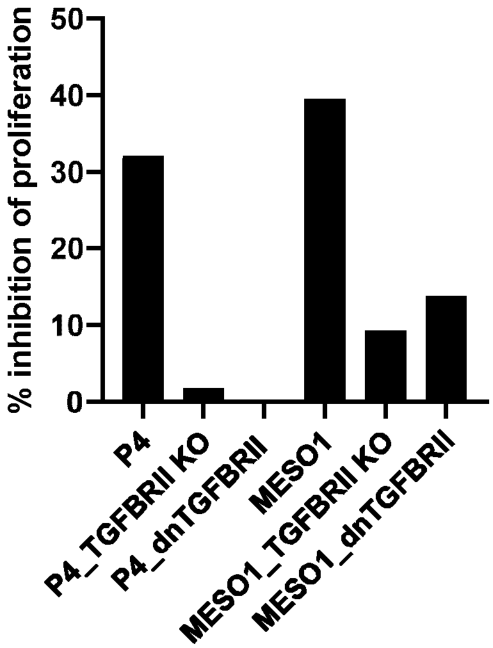

FIG. 24: Evaluation of UCARTmeso cells sensitivity to TGFb. A. Percentage of pSMAD2/3 positive (grey) or negative (black) cells among the CAR positive fraction of UCARTmeso produced in example 5 upon treatment with TGFb. B. Percentage of proliferation inhibition of the different UCARTmeso in presence of TGFb and recombinant mesothelin protein.

Table 1: Amino acid sequence of the different domains constituting the P4, Meso1 and MESO2 scFvs of the CAR illustrated in the examples.

Table 2: Amino acid sequence of the different domains, others than the scFv, constituting the MSLN CARs according to the invention.

Table 3: Examples of mAb-specific epitopes (and their corresponding mAbs) which can be used in the extracellular binding domain of the CAR of the invention for engineered cells sorting and depletion.

Table 4: Amino acid sequences of P4-R2, Meso1-R2, Meso1 and MESO2-R2 CARs.

Table 5: Examples of mAb-specific epitopes (and their corresponding mAbs), which can be inserted in the extracellular binding domain of the CAR of the invention.

Table 6: TALE-nuclease target sequences for TGFβRII gene.

Table 7: CRISPR target sequences for TGFβRII gene

Table 8: Genomic sequences targeted by the TALE-nucleases (TALEN) to inactivate TCR and CD52.

Table 9: Characteristics of the population of engineered T-cells used in the examples.

Table 10: Description of the six types of genetically modified T cells generated for the study provided in example 5.

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention is drawn to a general method of treating solid tumors by adoptive immune cells directed against the transmembrane protein MSLN, in particular the mesothelin's specific epitope region spanning the polypeptide sequence SEQ ID NO:25 in this protein, and more particularly by using allogeneic CAR-T cells directed against this epitope, which have proven particular efficiency.

Herein is described a method for producing engineered immune cells directed against human mesothelin (MSLN_human referred to as Q13421 in the Uniprot database), and more particularly specific mesothelin's polypeptide region represented by SEQ ID NO:25, which is presented at the surface of malignant cells. As shown in the experimental section of the present specification, efficient CAR T-cells have been produced by directing CARs against this antigen region comprising or consisting of SEQ ID NO:25, in particular by using the scFvs of antibody Meso1 comprising SEQ ID NO:9 and SEQ ID NO:10.

The resulting engineered immune cells according to the invention, in general NK or T-cells armed with a CAR comprising SEQ ID NO:9 and/or SEQ ID NO:10 have shown higher activation, potency, killing activity, cytokine release, and in-vivo persistence than their counterparts endowed with other prior anti-mesothelin CARs.

The present invention thus is drawn to CAR immune cells targeting specific epitope(s) comprised in the sequence SEQ ID NO.25 of MSLN protein, which is present at the surface of malignant cells, especially engineered for treating solid tumors.

Design of MSLN-CAR for Expression in Immune Cells:

By "Chimeric Antigen Receptor (CAR)" is meant recombinant receptors comprising a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains of CARs are generally derived from the cytoplasmic region of the CD3zeta or the Fc receptor gamma chains, which are generally combined with signaling domains from co-stimulatory molecules including CD28, OX-40 (CD134), ICOS and 4-1BB (CD137) to enhance survival and increase proliferation of the cells. CARs are generally expressed in effector immune cells to redirect their immune activity against antigens expressed at the surface of tumor cells from various malignancies including lymphomas and solid tumors. A component of a CAR is any functional subunit of a CAR that is encoded by an exogenous polynucleotide sequence introduced into the cell. For instance, this component can help to interact with the target antigen, the stability or the localization of the CAR into the cell.

In general, such CAR comprises:

- an extracellular ligand binding-domain comprising VH and VL from a monoclonal anti-mesothelin antibody;
- a transmembrane domain; and
- a signal transducing domain, preferably a cytoplasmic domain comprising a CD3 zeta signalling domain and a co-stimulatory domain.

The present invention is drawn more particularly to CARs, which are expressed in immune cells, such as NK or T-cells, said CAR comprising an antigen binding domain specifically binding SEQ ID NO:25.

According to a preferred aspect, the mesothelin specific chimeric antigen receptor (CAR) of the present invention has an extra cellular ligand binding-domain comprising at least one CDR region from the variable heavy VH chain of the antibody Meso1, selected from CDRH1-Meso1 (having identity with SEQ ID NO:3), CDRH2-Meso1 (having identity with SEQ ID NO:4) and CDRH3-Meso1 (having identity with SEQ ID NO:5, and/or from the variable heavy VL chain of said antibody selected from CDRL1-Meso1 (having identity with SEQ ID NO:6), CDRL2-Meso1 (having identity with SEQ ID NO:7), and CDRL3-Meso1 (having identity with SEQ ID NO:8).

In general, said extra cellular ligand binding-domain comprises:

- a variable heavy VH chain comprising CDRs from the antibody Meso1 having respectively at least 90% identity with SEQ ID NO:3 (CDRH1-Meso1), SEQ ID NO: 4 (CDRH2-Meso1) and SEQ ID NO:5 (CDRH3-Meso1), and/or
- a variable heavy VL chain comprising CDRs from the antibody Meso1 having respectively at least 90% identity with SEQ ID NO:6 (CDRL1-Meso1), SEQ ID NO:7 (CDRL2-Meso1) and SEQ ID NO:8 (CDRL3-Meso1).

According to preferred embodiments of the invention, the mesothelin specific chimeric antigen receptor has an extra cellular ligand binding-domain, which comprises VH and VL chains having at least 80%, preferably at least 90%, more preferably at least 95%, and even more preferably at least 99% sequence identity respectively with SEQ ID NO:9 (Meso1-VH) and SEQ ID NO:10 (Meso1-VL). In general, framework residues in the framework regions can be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions [See, e.g., Queen et al., U.S. Pat. No. 5,585,089; and Riechmann et al., (1988) *Nature,* 332:323, which are incorporated herein by reference in their entireties].

Various embodiments of the invention are provided through the features provided in the claims in view of the common practice and knowledge of one skilled in the art. Detailed sequences comprised into the CAR according to the present invention are detailed in Tables 1, 2, 3 and 4, where each lines or columns should be regarded as independent embodiments of the present invention.

TABLE 1

Amino acid sequence of the different domains constituting the P4, Meso1 and MESO2 scFvs.

| cFv sequences | SEQ ID # | Raw amino acid sequence |
|---|---|---|
| P4 heavy chain variable region | SEQ ID NO: 1 | QVQLQQSGPGLVTPSQTLSLTCAISGDSVSSNSATWNWIR QSPSRGLEWLGRTYYRSKWYNDYAVSVKSRMSINPDTSK NQFSLQLNSVTPEDTAVYYCARGMMTYYYGMDVWGQGT TVTVSSGILG |
| P4 light chain variable region | SEQ ID NO: 2 | QPVLTQSSSLSASPGASASLTCTLRSGINVGPYRIYWYQQK PGSPPQYLLNYKSDSDKQQGSGVPSRFSGSKDASANAGV LLISGLRSEDEADYYCMIWHSSAAVFGGGTQLTVLS |
| CDRH1- Meso1 | SEQ ID NO: 3 | SYYWS |
| CDRH2- Meso1 | SEQ ID NO: 4 | YIYYSGSTNYNPSLKS |
| CDRH3- Meso1 | SEQ ID NO: 5 | VDYKAFDI |
| CDRL1- Meso1 | SEQ ID NO: 6 | RASQGIRNDLH |
| CDRL2- Meso1 | SEQ ID NO: 7 | AASSLQS |
| CDRL3- Meso1 | SEQ ID NO: 8 | LQHYSYPWT |
| Meso1 heavy chain variable region | SEQ ID NO. 9 | QVQLQESGPGLVKPSETLSLTCTVSGGSISSYYWSWIRQP PGKGLEWIGYIYYSGSTNYNPSLKSRVTISVDTSKNQFSLK LSSVTAADTAVYYCARVDYKAFDIWGQGTMVTVSS |
| Meso1 light chain variable region | SEQ ID NO. 10 | DIQMTQSPSSLSASVGDRVTITCRASQGIRNDLHWYQQKP GKAPKRLIYAASSLQSGVPSRFSGSGSGTEFTLTISSLQPE DFATYYCLQHYSYPWTFGQGTKVEIK |
| MESO2 heavy chain variable region | SEQ ID NO. 11 | QVQLVQSGAEVKKPGESLKISCKGSGYSFTNYWIGWVRQ MPGKGLEWMGVIMPSDSYTRYSPSFQGQVTISADKSISTA YLQWSSLKASDTAMYYCARYGHGMYGGALDVWGQGTLV TVSS |
| MESO2 light chain variable region | SEQ ID NO. 12 | DIVLTQSPATLSLSPGERATLSCRASQSVRSSRLAWYQQK PGQAPRLLIYGASKRATGVPARFSGSGSGTDFTLTISSLEP EDFAVYYCQQYSHDPSGTFGQGTKVEIKRT |
| Linker | SEQ ID NO. 13 | GGGGSGGGGSGGGGS |

TABLE 2

Amino acid sequence of the different domains, others than the scFv, constituting the MSLN CARs according to the invention.

| Functional domains | SEQ ID # | Raw amino acid sequence |
|---|---|---|
| CD8α signal peptide | SEQ ID NO: 14 | MALPVTALLLPLALLLHAARP |
| R2 suicide switch | SEQ ID NO: 15 | SDPGSGGGGSCPYSNPSLCSGGGGSCPYSNPSLCS GGGGS |
| CD8α hinge | SEQ ID NO: 16 | TTTPAPRPPTPAPTIASQPLSLRPEACRPAAGGAVHTR GLDFACD |
| CD8α transmembrane domain | SEQ ID NO: 17 | IYIWAPLAGTCGVLLLSLVITLYC |
| 4-1BB co-stimulatory domain | SEQ ID NO: 18 | KRGRKKLLYIFKQPFMRPVQTTQEEDGCSCRFPEEEE GGCEL |

TABLE 2-continued

Amino acid sequence of the different domains, others than the scFv, constituting the MSLN CARs according to the invention.

| Functional domains | SEQ ID # | Raw amino acid sequence |
|---|---|---|
| CD3ζ signalling domain | SEQ ID NO: 19 | RVKFSRSADAPAYQQGQNQLYNELNLGRREEYDVLD KRRGRDPEMGGKPRRKNPQEGLYNELQKDKMAEAY SEIGMKGERRRGKGHDGLYQGLSTATKDTYDALHMQ ALPPR |

TABLE 3

Amino acid sequences of P4-R2, Meso1-R2, Meso1 and MESO2-R2 CARs.

| | Domains | | | | | | | | |
|---|---|---|---|---|---|---|---|---|---|
| CAR Designation Full | signal peptide (optional) | VH | linker | VL | R2 suicide switch | CD8α hinge | CD8α TM | 4-1BB IC | CD3ζ IC |
| P4-R2 (SEQ ID NO: 20) | SEQ ID NO: 14 | SEQ ID NO: 1 | SEQ ID NO: 13 | SEQ ID NO: 2 | SEQ ID NO: 15 | SEQ ID NO: 16 | SEQ ID NO: 17 | SEQ ID NO: 18 | SEQ ID NO: 19 |
| Meso1-R2 (SEQ ID NO: 21) | SEQ ID NO: 14 | SEQ ID NO: 9 | SEQ ID NO: 13 | SEQ ID NO: 10 | SEQ ID NO: 15 | SEQ ID NO: 16 | SEQ ID NO: 17 | SEQ ID NO: 18 | SEQ ID NO: 19 |
| Meso1 CAR (SEQ ID NO: 22) | SEQ ID NO: 14 | SEQ ID NO: 9 | SEQ ID NO: 13 | SEQ ID NO: 10 | None | SEQ ID NO: 16 | SEQ ID NO: 17 | SEQ ID NO: 18 | SEQ ID NO: 19 |
| MESO2-R2 (SEQ ID NO: 23) | SEQ ID NO: 14 | SEQ ID NO: 11 | SEQ ID NO: 13 | SEQ ID NO: 12 | SEQ ID NO: 15 | SEQ ID NO: 16 | SEQ ID NO: 17 | SEQ ID NO: 18 | SEQ ID NO: 19 |

TABLE 4 full polypeptide sequences of MSLN CARs, dnTGFβRII and MSLN epitope region

| CAR Designation | Polypeptide Sequence |
|---|---|
| P4-R2 (SEQ ID NO: 20) | MALPVTALLLPLALLLHAARPQVQLQQSGPGLVTPSQTLSLTCAISGDSV SSNSATWNWIRQSPSRGLEWLGRTYYRSKWYNDYAVSVKSRMSINPDT SKNQFSLQLNSVTPEDTAVYYCARGMMTYYYGMDVWGQGTTVTVSSGI LGGGGGSGGGGSGGGGSQPVLTQSSSLSASPGASASLTCTLRSGINVG PYRIYWYQQKPGSPPQYLLNYKSDSDKQQGSGVPSRFSGSKDASANAG VLLISGLRSEDEADYYCMIWHSSAAVFGGGTQLTVLSSDPGSGGGGSCP YSNPSLCSGGGGSCPYSNPSLCSGGGGSTTTPAPRPPTPAPTIASQPLS LRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADA PAYQQGQNQLYNELNLGRREEYDVLDKRRGRDPEMGGKPRRKNPQEG LYNELQKDKMAEAYSEIGMKGERRRGKGHDGLYQGLSTATKDTYDALH MQALPPR |
| Meso1-R2 (SEQ ID NO: 21) | MALPVTALLLPLALLLHAARPQVQLQESGPGLVKPSETLSLTCTVSGGSIS SYYWSWIRQPPGKGLEWIGYIYYSGSTNYNPSLKSRVTISVDTSKNQFSL KLSSVTAADTAVYYCARVDYKAFDIWGQGTMVTVSSGGGGSGGGGSG GGGSDIQMTQSPSSLSASVGDRVTITCRASQGIRNDLHWYQQKPGKAPK RLIYAASSLQSGVPSRFSGSGSGTEFTLTISSLQPEDFATYYCLQHYSYP WTFGQGTKVEIKSDPGSGGGGSCPYSNPSLCSGGGGSCPYSNPSLCS GGGGSTTTPAPRPPTPAPTIASQPLSLRPEACRPAAGGAVHTRGLDFAC DIYIWAPLAGTCGVLLLSLVITLYCKRGRKKLLYIFKQPFMRPVQTTQEED GCSCRFPEEEEGGCELRVKFSRSADAPAYQQGQNQLYNELNLGRREEY DVLDKRRGRDPEMGGKPRRKNPQEGLYNELQKDKMAEAYSEIGMKGE RRRGKGHDGLYQGLSTATKDTYDALHMQALPPR |
| P4 CAR SEQ ID NO: 161 | MALPVTALLLPLALLLHAARPQVQLQQSGPGLVTPSQTLSLTCAISGDSV SSNSATWNWIRQSPSRGLEWLGRTYYRSKWYNDYAVSVKSRMSINPDT SKNQFSLQLNSVTPEDTAVYYCARGMMTYYYGMDVWGQGTTVTVSSGI LGGGGGSGGGGSGGGGSQPVLTQSSSLSASPGASASLTCTLRSGINVG PYRIYWYQQKPGSPPQYLLNYKSDSDKQQGSGVPSRFSGSKDASANAG VLLISGLRSEDEADYYCMIWHSSAAVFGGGTQLTVLSTTTPAPRPPTPAP TIASQPLSLRPEACRPAAGGAVHTRGLDFACDIYIWAPLAGTCGVLLLSLV ITLYCKRGRKKLLYIFKQPFMRPVQTTQEEDGCSCRFPEEEEGGCELRVK FSRSADAPAYQQGQNQLYNELNLGRREEYDVLDKRRGRDPEMGGKPR |

TABLE 4-continued full polypeptide sequences of MSLN CARs, dnTGFβRII and MSLN epitope region

| CAR Designation | Polypeptide Sequence |
|---|---|
| | RKNPQEGLYNELQKDKMAEAYSEIGMKGERRRGKGHDGLYQGLSTATK<br>DTYDALHMQALPPR |
| Meso1 CAR<br>(SEQ ID NO: 22) | MALPVTALLLPLALLLHAARPQVQLQESGPGLVKPSETLSLTCTVSGGSIS<br>SYYWSWIRQPPGKGLEWIGYIYYSGSTNYNPSLKSRVTISVDTSKNQFSL<br>KLSSVTAADTAVYYCARVDYKAFDIWGQGTMVTVSSGGGGSGGGGSG<br>GGGSDIQMTQSPSSLSASVGDRVTITCRASQGIRNDLHWYQQKPGKAPK<br>RLIYAASSLQSGVPSRFSGSGSGTEFTLTISSLQPEDFATYYCLQHYSYP<br>WTFGQGTKVEIKTTTPAPRPPTPAPTIASQPLSLRPEACRPAAGGAVHTR<br>GLDFACDIYIWAPLAGTCGVLLLSLVITLYCKRGRKKLLYIFKQPFMRPVQ<br>TTQEEDGCSCRFPEEEEGGCELRVKFSRSADAPAYQQGQNQLYNELNL<br>GRREEYDVLDKRRGRDPEMGGKPRRKNPQEGLYNELQKDKMAEAYSEI<br>GMKGERRRGKGHDGLYQGLSTATKDTYDALHMQALPPR |
| MESO2-R2<br>(SEQ ID NO: 23) | MALPVTALLLPLALLLHAARPQVQLVQSGAEVKKPGESLKISCKGSGYSF<br>TNYWIGWVRQMPGKGLEWMGVIMPSDSYTRYSPSFQGQVTISADKSIST<br>AYLQWSSLKASDTAMYYCARYGHGMYGGALDVWGQGTLVTVSSGGGG<br>SGGGGSGGGGSDIVLTQSPATLSLSPGERATLSCRASQSVRSSRLAWY<br>QQKPGQAPRLLIYGASKRATGVPARFSGSGSGTDFTLTISSLEPEDFAVY<br>YCQQYSHDPSGTFGQGTKVEIKRTSDPGSGGGGSCPYSNPSLCSGGG<br>GSCPYSNPSLCSGGGGSTTTPAPRPPTPAPTIASQPLSLRPEACRPAAG<br>GAVHTRGLDFACDIYIWAPLAGTCGVLLLSLVITLYCKRGRKKLLYIFKQPF<br>MRPVQTTQEEDGCSCRFPEEEEGGCELRVKFSRSADAPAYQQGQNQL<br>YNELNLGRREEYDVLDKRRGRDPEMGGKPRRKNPQEGLYNELQKDKM<br>AEAYSEIGMKGERRRGKGHDGLYQGLSTATKDTYDALHMQALPPR |
| dnTGFβRII<br>Decoy truncated<br>version of TGFβRII<br>(SEQ ID NO: 24) | MGRGLLRGLWPLHIVLWTRIASTIPPHVQKSVNNDMIVTDNNGAVKFPQL<br>CKFCDVRFSTCDNQKSCMSNCSITSICEKPQEVCVAVWRKNDENITLETV<br>CHDPKLPYHDFILEDAASPKCIMKEKKKPGETFFMCSCSSDECNDNIIFSE<br>EYNTSNPDLLLVIFQVTGISLLPPLGVAISVIIIFYCYRVNRQQKLSS |
| MSLN target antigen<br>region (SEQ ID<br>NO: 25) | EVEKTACPSGKKAREIDESLIFYKKWELEACVDAALLATQMDRVNAIPFTY<br>EQLDVLKHKLDELYPQGYPESVIQHLGYLFLKMSPEDIRKWNVTSLETLK<br>ALLEVNKGHEMSPQAPRRPLPQVATLIDRFVKGRGQLDKDTLDTLTAFYP<br>GYLCSLSPEELSSVPPSSIWAVRPQDLDTCDPRQLDVLYPKARLAFQNM<br>NGSEYFVKIQSFLGGAPTEDLKALSQQNVSMDLATFMKLRTDAVLPLTVA<br>EVQKLLGPHVEGLKAEERHRPVRDWILRQRQDDLDTLGLGL |

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence selected from the group consisting of (SEQ ID NO: 9).

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

In a preferred embodiment, the signal transduction domain of the CAR of the present invention comprises a part of co-stimulatory signal molecule selected from the group consisting of fragment of 4-1BB (GenBank: AAA53133.) and CD28 (NP_006130.1). In particular the signal transduction domain of the CAR of the present invention comprises amino acid sequence which comprises at least 70%, preferably at least 80%, more preferably at least 90%, 95% 97% or 99% sequence identity with either 4-1BB or CD28. Accordingly, the mesothelin specific chimeric antigen receptor as per the present invention preferably comprises a CD3 zeta signalling domain that has at least 80% identity with SEQ ID NO. 19 and generally comprises a co-stimulatory domain that has at least 80% identity with SEQ ID NO.18. (4-1BB).

A CAR according to the present invention is generally expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ζ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively, or hinge polypeptides which display preferably at least 80%, more preferably at least 90%, 95% 97% or 99% sequence identity with these polypeptides.

Accordingly mesothelin specific chimeric antigen receptor (CAR) according to the present invention comprises a hinge between the extracellular ligand-binding domain and the transmembrane domain, said hinge being generally selected from CD8α hinge, IgG1 hinge and FcγRIIIα hinge or polypeptides sharing at least 80%, preferably at least 90%, more preferably at least 95%, and even more preferably at least 99% sequence identity with these polypeptides, in particular with SEQ ID NO:16 (CD8a).

A CAR according to the invention generally further comprises a transmembrane domain (TM) preferably selected from CD8α and 4-1B, more preferably from CD8α-TM or a polypeptide showing at least 80%, more preferably at least 90%, 95% 97% or 99% sequence identity with SEQ ID NO.17 (CD8α TM).

According to a further embodiment, the mesothelin specific CAR according to the invention comprises a safety switch useful for sorting, purifying and/or depleting the engineered immune cells. Although the methods of the invention are designed to be performed ex-vivo, depletion may be performed in-vivo to control immune cell's expansion into the patient and to potentially stop the effects of the treatment by using antibodies approved for human therapeutic use by regulatory agencies. Examples of mAb-specific epitopes (and their corresponding mAbs) that can be integrated in the extracellular binding domain of the CAR of the invention are listed in Table 5.

TABLE 5

Examples of mAb-specific epitopes (and their corresponding mAbs), which can be inserted in the extracellular binding domain of the CAR of the invention.

| | | |
|---|---|---|
| **Rituximab** | | |
| Mimotope | SEQ ID NO: 26 | CPYSNPSLC |
| **Palivizumab** | | |
| Epitope | SEQ ID NO: 27 | NSELLSLINDMPITNDQKKLMSNN |
| **Cetuximab** | | |
| Mimotope 1 | SEQ ID NO: 28 | CQFDLSTRRLKC |
| Mimotope 2 | SEQ ID NO: 29 | CQYNLSSRALKC |

TABLE 5-continued

Examples of mAb-specific epitopes (and their corresponding mAbs), which can be inserted in the extracellular binding domain of the CAR of the invention.

| | | |
|---|---|---|
| Mimotope 3 | SEQ ID NO: 30 | CVWQRWQKSYVC |
| Mimotope 4 | SEQ ID NO: 31 | CMWDRFSRWYKC |
| **Nivolumab** | | |
| Epitope 1 | SEQ ID NO: 32 | SFVLNWYRMSPSNQTDKLAAFPEDR |
| Epitope 2 | SEQ ID NO: 33 | SGTYLCGAISLAPKAQIKE |
| **QBEND-10** | | |
| Epitope | SEQ ID NO: 34 | ELPTQGTFSNVSTNVSPAKPTTTA |
| **Alemtuzumab** | | |
| Epitope | SEQ ID NO: 35 | GQNDTSQTSSPS |

Accordingly, a mesothelin specific CAR according to the invention preferably comprises a safety switch which comprises at least one exogenous mAb epitope listed in Table 5. Preferably, a mesothelin specific CAR according to the invention preferably comprises a safety switch which comprises the epitope CPYSNPSLC (SEQ ID NO:26) that is specifically bound by rituximab. More preferably, a mesothelin specific CAR comprises a safety switch referred to as "R2", that has at least 90% identity with SEQ ID NO:15.

A mesothelin specific CAR according to the invention generally also comprises a signal peptide to help its expression at the surface of the engineered cells. The chimeric antigen receptor (CAR) generally form single-chain polypeptides, but may also be produced in multi-chain formats as described for instance in WO2014039523.

As illustrated in the examples, preferred CARs according to the invention is MSLN-CAR-Meso1-R2 or MSLN-CAR-Meso1, which has respectively at least 80%, preferably at least 90%, more preferably at least 95%, and even more preferably at least 99% overall amino acid sequence identity with SEQ ID NO:21 (Meso1-R2) or SEQ ID NO:22 (Meso1).

The structure of the preferred polypeptide structure of the MSLN-CARs of the present invention are illustrated in FIG. 1.

More generally, the CARs of the present invention are produced by assembling the different polynucleotides sequences encoding the successive fragments of the CAR polypeptide(s) into vectors for transfection and expression into immune cells as described in the art and as reviewed for instance by [Boyiadzis, M. M., et al. (2018) Chimeric antigen receptor (CAR) T therapies for the treatment of hematologic malignancies: clinical perspective and significance. *j. immunotherapy cancer* 6, 137].

The present invention is drawn to the polynucleotides and vectors as well as any intermediary steps intervening in the process of manufacturing the immune cells referred herein.

By "vector" is meant a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous repli¬cation (episomal vector) and/or expression of nucleic acids to which they are linked (expression vectors). Large numbers of suitable vectors are known to those of skill in the art and commercially available. Viral vectors include retrovirus, adenovirus, parvovirus (e.g. adeno¬associated viruses (AAV), coronavirus, negative strand RNA viruses such as ortho¬myxovirus (e.g., influenza virus), rhabdovirus (e.g., rabies and vesicular stoma¬titis virus), para¬myxovirus (e.g. measles and Sendai), positive strand RNA viruses such as picor¬navirus and alphavirus, and double-stranded DNA viruses including adenovirus, herpesvirus (e.g., Herpes Simplex virus types 1 and 2, Epstein-Barr virus, cytomega¬lovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lenti¬virus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

In particular, the present invention provides inter alia an expression vector in the form of a lentiviral vector or an AAV vector comprising a polynucleotide sequence encoding a CAR as described herein.

Such lentiviral vector may comprise a polynucleotide sequence encoding a CAR according to the present invention operably linked to a promoter (such as the Spleen Focus Forming Virus promoter (SFFV)). By "operably linked" it is meant a juxtaposition wherein the components described are in a relationship permitting them to function in their intended manner. A gene (such as a CAR encoding polynucleotide sequence) is "operably linked" to a promoter when its transcription is under the control of said promoter and this transcription results in the production of the product encoded by said gene.

The lentiviral vector of the present invention typically contains regulatory elements such as 5' and 3' long terminal repeat (LTR) sequences, but may also contain other structural and functional genetic elements that are primarily derived from a lentivirus. Such structural and functional genetic elements are well known in the art. The lentiviral vector may, for example, contain the genes gag, pol and env. Preferably, however, the lentiviral vector of the present invention does not contain the genes gag, pol and env. As further regulatory elements the lentiviral vector may include one or more (such as two or more) of a packaging signal (such as the packaging signal ψ), a primer binding site, a trans-activation-responsive region (TAR) and a rev-responsive element (RRE).

The 5' and 3' long terminal repeat (LTR) sequences typically flanking the lentiviral genome have promoter/enhancer activity and are essential for the correct expression of the full-length lentiviral vector transcript. The LTRs usually include the repetitive sequence U3RU5 present at both the 5'- and 3' ends of a double-stranded DNA molecule, which is a combination of 5' R-U5 segment and the 3' U3-R segment of the single-stranded RNA, wherein repetition R occurs at both termini of the RNA, while U5 (unique sequence 5) only occurs at the 5' end of the RNA and U3 (unique sequence 3) only occurs at the 3' end of the RNA. Lentiviral vectors can been improved in their safety by removal of the U3 sequence, resulting in "self-inactivating" vectors that are entirely devoid of viral promoter and enhancer sequences originally present within the LTRs. Consequently, the vector is capable of infecting and then integrating into the host genome only once, and cannot be passed further, thereby increasing the safety of the use of the vector as a gene delivery vector.

According to some embodiments, the lentiviral vector is a self-inactivating (SIN) lentiviral vector. According to particular embodiments, the lentiviral vector contains a 3' LTR in which the 3' LTR enhancer-promoter sequence (i.e. U3 sequence) has been modified (e.g., deleted).

According to some embodiments, the lentiviral vector comprises a polynucleotide sequence which comprises one or several of the following elements in a 5' to 3' order:
- a 5' long terminal repeat (5' LTR);
- a promoter (such as the EF1-alpha promoter);
- a polynucleotide sequence encoding a chimeric antigen receptor according to the present invention; and/or
- a 3' long terminal repeat (3' LTR), preferably 3' self-inactivating LTR.

According to particular embodiments, the lentiviral vector can further comprise a polynucleotide sequence which comprises at least one of the following elements in a 5' to 3' order:
- a 5' long terminal repeat (5' LTR);
- a promoter (such as the EF1-alpha promoter);
- a CAR according to the present invention optionally comprising a safety switch, such as R2,
- a polynucleotide sequence encoding a 2A peptide;
- a polynucleotide sequence encoding a or any further polypeptide to be co-expressed with the CAR, such as dnTGFβR;

and/or
- a 3' long terminal repeat (3' LTR), preferably 3' self-inactivating LTR.

Alternatively, the lentiviral vector can comprise at least one of the following elements in a 5' to 3' order:
- a 5' long terminal repeat (5' LTR);
- a promoter (such as the EF1-alpha promoter);
- a polynucleotide sequence encoding a or any further polypeptide to be co-expressed with the CAR, such as dnTGFβR;
- a polynucleotide sequence encoding a 2A peptide;
- a CAR according to the present invention optionally comprising a safety switch, such as R2, and/or
- a 3' long terminal repeat (3' LTR), preferably 3' self-inactivating LTR.

In general, the resulting vector form a single transcription unit operably linked to the promoter of item (b) and are all transcribed under the control of said promoter.

AAV vectors, especially vectors from the AAV6 family [Wang, J., et al. (2015) Homology-driven genome editing in hematopoietic stem and progenitor cells using ZFN mRNA and AAV6 donors. Nat Biotechnol 33, 1256-1263] are particularly useful to introduce the MSLN-CARs according to the present invention into the genome by using site-specific homologous recombination. In general, site specific homologous recombination is induced in immune cells by expressing rare-cutting endonucleases, such as TALEN, as already taught in EP3276000 and WO2018073391 with respect to other CARs for treating blood cancers. CAR site-specific integration can have several benefits, such as a more stable integration, an integration that places the transgene under the transcription control of an endogenous promoter at a selected locus, an integration that can inactivate an endogenous locus. These later aspects are detailed into the following section pertaining to the genome engineering of the therapeutic immune cells.

As one object of the present invention is provided an AAV vector comprising a polynucleotide sequence encoding a MSLN-CAR as previously specified and optionally another sequence encoding a cis-regulatory elements (e.g. 2A peptide cleavage site) or an internal ribosome entry site (IRES), allowing the co-expression of a third sequence encoding a product improving the therapeutic potency of the engineered immune cells. Example is given herein of over expression of dnTGFβRII, which was found to reduce SMAD2-3 phosphorylation, which concurs to reduce exhaustion of the cells that is induced by TGFβ in the tumor environment.

The term "therapeutic properties" encompasses the different ways such cells can be improved in the perspective of their use in therapeutic treatments. This means that the cells are genetically engineered to confer them a therapeutic advantage benefit (i.e. therapeutic potency) or to facilitate their use or their production. For instance, the genetic engineering can concur to the effector cells having better survival, faster growth, shorter cell cycles, improved immune activity, be more functional, more differentiated, more specific with respect to their target cells, more sensitive or resistant to drugs, less sensitive to glucose deprivation, oxygen or amino acid depletion (i.e. resilient to tumor microenvironment). Progenitor cells may be more productive, better tolerated by the recipient patient, more likely to produce cells that will differentiate in the desired effector cells. These examples of "therapeutic properties" are given as examples without limitation.

Genome Engineering of the MSLN CAR Immune Cells for Cell Therapy

The invention more particularly involves cells and reagents with the following characteristics:

Effector cells: Effector cells are the relatively short-lived activated cells that defend the body in an immune response. Activated T cells, which include cytotoxic T cells and helper T cells are preferred effector cells to carry out cell-mediated responses. The category of effector T cell is a broad one that includes various T cell types that actively respond to a stimulus, such as co-stimulation. This includes helper, killer, regulatory, and potentially other T cell types.

By "immune cell" is meant a cell of hematopoietic origin functionally involved in the initiation and/or execution of innate and/or adaptative immune response, such as typically CD3 or CD4 positive cells. The immune cell according to the present invention may be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes.

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

Primary immune cells can be obtained from a number of non-limiting sources, including peripheral blood mononuclear cells (PBMC), bone marrow, lymph node tissue, cord blood, thymus tissue, tissue from a site of infection, ascites, pleural effusion, spleen tissue, and from tumors, such as tumor infiltrating lymphocytes. In some embodiments, said immune cell can be derived from a healthy donor, from a patient diagnosed with cancer or from a patient diagnosed with an infection. In another embodiment, said cell is part of a mixed population of immune cells which present different phenotypic characteristics, such as comprising CD4, CD8 and CD56 positive cells. Primary immune cells are provided from donors or patients through a variety of methods known in the art, as for instance by leukapheresis techniques as reviewed by Schwartz J. et al. (Guidelines on the use of therapeutic apheresis in clinical practice-evidence-based approach from the Writing Committee of the American Society for Apheresis: the sixth special issue (2013) *J Clin Apher.* 28(3):145-284).

The immune cells derived from stem cells are also regarded as primary immune cells according to the present invention, in particular those deriving from induced pluripotent stem cells (iPS) [Yamanaka, K. et al. (2008). "Generation of Mouse Induced Pluripotent Stem Cells Without Viral Vectors". *Science.* 322 (5903): 949-53]. Lentiviral expression of reprogramming factors has been used to induce multipotent cells from human peripheral blood cells [Staerk, J. et al. (2010). "Reprogramming of human peripheral blood cells to induced pluripotent stem cells". *Cell stem cell.* 7 (1): 20-4] [Loh, Y H. et al. (2010). "Reprogramming of T cells from human peripheral blood". *Cell stem cell.* 7 (1): 15-9].

According to a preferred embodiment of the invention, the immune cells are derived from human embryonic stem cells by techniques well known in the art that do not involve the destruction of human embryos [Chung et al. (2008) Human Embryonic Stem Cell lines generated without embryo destruction, *Cell Stem Cell* 2(2):113-117].

By "Genetic engineering" is meant any methods aiming to introduce, modify and/or withdraw genetic material from a cell. By "gene editing" is meant a genetic engineering allowing genetic material to be added, removed, or altered at specific locations (loci) in the genome, including punctual mutations. Gene editing generally involves sequence specific reagents.

By "sequence-specific reagent" is meant any active molecule that has the ability to specifically recognize a selected polynucleotide sequence at a genomic locus, referred to as "target sequence", which is generally of at least 9 bp, more preferably of at least 10 bp and even more preferably of at least 12 pb in length, in view of modifying the expression of said genomic locus. Said expression can be modified by mutation, deletion or insertion into coding or regulatory polynucleotide sequences, by epigenetic change, such as by methylation or histone modification, or by interfering at the transcriptional level by interacting with transcription factors or polymerases.

Examples of sequence-specific reagents are endonucleases, RNA guides, RNAi, methylases, exonucleases, histone deacetylases, endonucleases, end-processing enzymes such as exonucleases, and more particularly cytidine deaminases such as those coupled with the CRISPR/cas9 system to perform base editing (i.e. nucleotide substitution) without necessarily resorting to cleavage by nucleases as described for instance by Hess, G. T. et al. [Methods and applications of CRISPR-mediated base editing in eukaryotic genomes (2017) *Mol Cell.* 68(1): 26-43.

According to a preferred aspect of the invention, said sequence-specific reagent is preferably a sequence-specific nuclease reagent, such as a RNA guide coupled with a guided endonuclease.

The present invention aims to improve the therapeutic potential of immune cells through gene editing techniques, especially by gene targeted integration.

By "gene targeting integration" is meant any known site-specific methods allowing to insert, replace or correct a genomic coding sequence into a living cell.

According to a preferred aspect of the present invention, said gene targeted integration involves homologous gene recombination at the locus of the targeted gene to result the insertion or replacement of at least one exogenous nucleotide, preferably a sequence of several nucleotides (i.e. polynucleotide), and more preferably a coding sequence.

By "DNA target", "DNA target sequence", "target DNA sequence", "nucleic acid target sequence", "target sequence", or "processing site" is intended a polynucleotide sequence that can be targeted and processed by a sequence-specific nuclease reagent according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

"Rare-cutting endonucleases" are sequence-specific endonuclease reagents of choice, insofar as their recognition sequences generally range from 10 to 50 successive base pairs, preferably from 12 to 30 bp, and more preferably from 14 to 20 bp.

According to a preferred aspect of the invention, said endonuclease reagent is a nucleic acid encoding an "engineered" or "programmable" rare-cutting endonuclease, such as a homing endonuclease as described for instance by Arnould S., et al. [WO2004067736], a zinc finger nuclease (ZFN) as described, for instance, by Urnov F., et al. [Highly efficient endogenous human gene correction using designed zinc-finger nucleases (2005) *Nature* 435:646-651], a TALE-Nuclease as described, for instance, by Mussolino et al. [A novel TALE nuclease scaffold enables high genome editing activity in combination with low toxicity (2011) *Nucl. Acids Res.* 39(21):9283-9293], or a MegaTAL nuclease as described, for instance by Boissel et al. [MegaTALs: a rare-cleaving nuclease architecture for therapeutic genome engineering (2013) *Nucleic Acids Research* 42(4):2591-2601].

According to another embodiment, the endonuclease reagent is a RNA-guide to be used in conjunction with a RNA guided endonuclease, such as Cas9 or Cpf1, as per, inter alia, the teaching by Doudna, J., and Chapentier, E., [The new frontier of genome engineering with CRISPR-Cas9 (2014) *Science* 346 (6213):1077], which is incorporated herein by reference.

According to a preferred aspect of the invention, the endonuclease reagent is transiently expressed into the cells, meaning that said reagent is not supposed to integrate into the genome or persist over a long period of time, such as be the case of RNA, more particularly mRNA, proteins or complexes mixing proteins and nucleic acids (eg: Ribonucleoproteins).

An endonuclease under mRNA form is preferably synthetized with a cap to enhance its stability according to techniques well known in the art, as described, for instance, by Kore A. L., et al. [Locked nucleic acid (LNA)-modified dinucleotide mRNA cap analogue: synthesis, enzymatic incorporation, and utilization (2009) *J Am Chem Soc.* 131 (18):6364-5].

In general, electroporation steps that are used to transfect primary immune cells, such as PBMCs are typically performed in closed chambers comprising parallel plate electrodes producing a pulse electric field between said parallel plate electrodes greater than 100 volts/cm and less than 5,000 volts/cm, substantially uniform throughout the treatment volume such as described in WO2004083379, which is incorporated by reference, especially from page 23, line 25 to page 29, line 11. One such electroporation chamber preferably has a geometric factor ($cm^{-1}$) defined by the quotient of the electrode gap squared (cm2) divided by the chamber volume ($cm^3$), wherein the geometric factor is less than or equal to 0.1 $cm^{-1}$, wherein the suspension of the cells and the sequence-specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

Due to their higher specificity, TALE-nuclease have proven to be particularly appropriate sequence specific nuclease reagents for therapeutic applications, especially under heterodimeric forms—i.e. working by pairs with a "right" monomer (also referred to as "5'" or "forward") and "left" monomer (also referred to as "3'" or "reverse") as reported for instance by Mussolino et al. [TALEN facilitate targeted genome editing in human cells with high specificity and low cytotoxicity (2014) *Nucl. Acids Res.* 42(10): 6762-6773].

As previously stated, the sequence specific reagent is preferably under the form of nucleic acids, such as under DNA or RNA form encoding a rare cutting endonuclease a subunit thereof, but they can also be part of conjugates involving polynucleotide(s) and polypeptide(s) such as so-called "ribonucleoproteins". Such conjugates can be formed with reagents as Cas9 or Cpf1 (RNA-guided endonucleases) as respectively described by Zetsche, B. et al. [Cpf1 Is a Single RNA-Guided Endonuclease of a Class 2 CRISPR-Cas System (2015) *Cell* 163(3): 759-771] and by Gao F. et al. [DNA-guided genome editing using the *Natronobacterium gregoryi* Argonaute (2016) *Nature Biotech*], which involve RNA or DNA guides that can be complexed with their respective nucleases.

"Exogenous sequence" refers to any nucleotide or nucleic acid sequence that was not initially present at the selected locus. This sequence may be homologous to, or a copy of, a genomic sequence, or be a foreign sequence introduced into the cell. By opposition "endogenous sequence" means a cell genomic sequence initially present at a locus. The exogenous sequence preferably codes for a polypeptide which expression confers a therapeutic advantage over sister cells that have not integrated this exogenous sequence at the locus. An endogenous sequence that is gene edited by the insertion of a nucleotide or polynucleotide as per the method of the present invention, in order to express a different polypeptide is broadly referred to as an exogenous coding sequence.

By using the above reagents and techniques, the present invention concurs to develop methods for producing therapeutic cells by proceeding with one or several of the following steps:

- Providing immune cells, preferably primary cells, from a donor or a patient;
- Expressing into such cells a MSLN-CAR as previously described, generally by introducing the MSLN-CAR coding sequence into the cell's genome via a viral vector;
- Introducing into such immune cells a sequence specific-reagent, such as rare-cutting endonuclease to induce a modification (mutations or coding sequence insertion) at an endogenous gene locus; and/or
- Introducing into said cell an exogenous coding sequence to improve the therapeutic potency thereof, in particular its immune properties.

According to some aspects of the invention the immune cells originate from a patient or a compatible donor, in which the MSLN CAR is expressed in view of performing so called "autologous" infusion of the engineered immune cells. They can also be derived from stem cells, such as iPS cells, originating from such patient or compatible donor or from tumor infiltrating lymphocytes (TILL).

According to some aspects of the invention, the method aims to provide "off the shelf" compositions of immune cells, said immune cells being engineered for allogeneic therapeutic treatments.

By "allogeneic" is meant that the cells originate from a donor, is produced or differentiated from stem cells in view of being infused into patients having a different haplotype.

Such immune cells are generally engineered to be less alloreactive and/or become more persistent with respect to their patient host. More specifically the present methods comprise the steps of reducing or inactivating TCR expression into T-cells, or stem cells to be derived into T-cells. This can be obtained by different sequence specific-reagents, such as by gene silencing or gene editing techniques (nuclease, base editing, RNAi . . . ).

The applicant has formerly made available robust protocols and gene editing strategies to produce allogeneic therapeutic grade T-cells from PBMCs, especially by providing very safe and specific endonuclease reagents under the form of TALE-nucleases (TALEN®). The production of so-called "universal T-cells", which are $[TCR]^{neg}$ T-cells from donors was achieved and successfully injected to patients with reduced Graft versus Host Disease (GVhD) [Poirot et al. (2015) Multiplex Genome-Edited T-cell Manufacturing Platform for "Off-the-Shelf" Adoptive T-cell Immunotherapies. *Cancer. Res.* 75 (18): 3853-3864] [Qasim, W. et al.

(2017) Molecular remission of infant B-ALL after infusion of universal TALEN gene-edited CAR T cells. *Science Translational* 9(374)]. Meanwhile, inactivation of TCR or β2m components in primary T-cells can be combined with the inactivation of further genes encoding checkpoint inhibitor proteins, such as described for instance in WO2014184744.

In preferred embodiments, the present invention provides with a method to engineer an immune cell, wherein at least one gene encoding TCRalpha or TCRbeta is inactivated in said immune cell, preferably by expression of a rare-cutting endonuclease, whereas an exogenous polynucleotide encoding MSLN-CAR is introduced into the genome of said cell for stable expression. Preferably, said exogenous sequence is integrated at said locus encoding TCRalpha or TCRbeta, more preferably under transcriptional control of an endogenous promoter of TCRalpha or TCRbeta.

In further embodiments, the engineered immune cell can be further modified to confer resistance to at least one immune suppressive drug, such as by inactivating CD52 the target of anti-CD52 antibody (e.g.: alemtuzumab), which has been previously described with respect to the treatment of blood cancers for instance in WO2013176915.

While the use of anti-CD52 lymphodepletion agents had been limited so far to liquid tumor cancers [Quasim W. et al. (2019) Allogeneic CAR T cell therapies for leukemia *Am J Hematol.* 94:S50-S54.], one major aspect of the present invention is the use of genetically engineered lymphocytes made resistant to lymphodepletion regimen for the treatment of solid tumors.

Also the present invention provides engineered lymphocytes endowed with chimeric antigen receptors directed against solid tumors, especially against mesothelin positive cells, for their use in solid tumor cancer treatments in combination with, or preceded by, a lymphodepletion treatment step.

Such lymphodepletion regimen can comprise anti-CD52 reagents, such as Alemtuzumab, or purine analogues, as those used for treating blood cancers.

In preferred embodiments, the engineered lymphocytes endowed with MSLN-CAR described herein are made resistant to such lymphodepleting regimen by inhibiting or disrupting the expression of the molecules that are targeted by the lymphodepletion reagents, like for instance the antigen CD52 in the case of Alemtuzumab.

In further embodiments, the engineered immune cell can be further modified to confer resistance to and/or a chemotherapy drug, in particular a purine analogue drug, for example by inactivating DCK as described in WO201575195.

As indicated before, it is an important aspect of the present invention to treat solid tumor cancers with genetically engineered lymphocytes endowed with chimeric antigen receptors, which are made resistant to chemotherapy or lymphodepletion regimen. Such regimen can comprise antibodies targeting antigens present at the surface of immune cells, such as CD52, CD3, CD4, CD8, CD45, or other specific markers, but also less specific drugs such as purine analogues (ex: fludarabine and/or chlorofarabine) and glucocorticoids. One aspect of the invention is to make the engineered lymphocytes resistant to such regimen by inactivating or reducing the expression of the genes that encode at least one molecular target of these lymphodepletion reagents, for instance the gene DCK that metabolizes purine analogues or the genes encoding glucocorticoid receptors (GR).

The present invention is therefore more particularly focused on CAR positive cells, which expression of TCR, CD52 and/or DCK and/or GR is reduced, inactivated or deficient to make them less alloreactive and resistant to lymphodepletion regimen, for their allogeneic use in solid cancer treatments.

In further embodiments, the engineered immune cell can be further modified to improve its persistence or its lifespan into the patient, in particular inactivating a gene encoding MHC-I component(s) such as HLA or β2m, such as described in WO2015136001 or by Liu, X. et al. [CRISPR-Cas9-mediated multiplex gene editing in CAR-T cells (2017) *Cell Res* 27:154-157].

According to a preferred aspect of the invention, the engineered immune cell is mutated to improve its CAR-dependent immune activation, in particular to reduce or suppress the expression of immune checkpoint proteins and/or their receptors thereof, such as PD1 or CTLA4 as described in WO2014184744.

In further embodiments, the engineered immune cell can be further modified to obtain co-expression in said cell of another exogenous genetic sequence selected from one encoding:

- NK cell inhibitor, such as HLAG, HLAE or ULBP1;
- CRS inhibitor, such as is a mutated IL6Ra, sGP130 or IL18-BP;
- Cytochrome(s) P450, CYP2D6-1, CYP2D6-2, CYP2C9, CYP3A4, CYP2C19 or CYP1A2, conferring hypersensitivity of said immune cells to a drug, such as cyclophosphamide and/or isophosphamide;
- Dihydrofolate reductase (DHFR), inosine monophosphate dehydrogenase 2 (IMPDH2), calcineurin or methylguanine transferase (MGMT), mTORmut or Lckmut, conferring drug resistance;
- Chemokine or a cytokine, such as IL-2, IL-12 and IL-15;
- Chemokine receptors, such as CCR2, CXCR2, or CXCR4; and/or
- a secreted inhibitor of Tumor Associated Macrophages (TAM), such as a CCR2/CCL2 neutralization agent, to enhance the therapeutic activity of the immune cells;

The present application claims immune cells co-expressing in engineered immune cells at least one exogenous sequence encoding MSLN-CAR as described herein, with another exogenous sequence encoding a human polypeptide selected in the above list for the purpose of producing therapeutic compositions against solid tumors.

Combination of Expression of MSLN-CAR and Disruption of TGFbRII Signalling Pathway in the Therapeutic Engineered Immune Cells The present invention more particularly combines the expression of an exogenous sequence encoding MSLN-CAR as previously described, with another exogenous sequence encoding an inhibitor of a TGFbeta receptor, especially an inhibitor of TGFβRII (Uniprot-P37173).

TGFbeta receptors have been described as having preponderant roles in tumor microenvironment [Papageorgis, P. et al. (2015). Role of TGFβ in regulation of the tumor microenvironment and drug delivery (Review). International Journal of Oncology, 46, 933-943].

Although, the exact role of TGFbeta receptors in tumorogenesis remains controversial, the inventors have found that co-expressing mesothelin-specific chimeric antigen receptor (CAR) with another exogenous genetic sequence encoding an inhibitor of TGFBRII signalling and/or inactivating or reducing TGFbeta receptor signalling by using a sequence-specific reagent, was leading to an improved therapeutic potency of the engineered immune cells. In particular, the inventors have used two different approaches to impair TGFβRII signalling pathway, which may be combined together:

expression of an inactive ligand of TGFβRII, such as a dominant negative TGFβRII (SEQ ID NO:26), as described by Hiramatsu, K., et al. [Expression of dominant negative TGF-β receptors inhibits cartilage formation in conditional transgenic mice (2011) *J. Bone. Miner. Metab.* 29: 493]. or a similar inactive form of TGFβRII having at least 80%, preferably at least 90%, more preferably at least 95% identity with the polypeptide sequence SEQ ID NO:26.

and/or inactivation of endogenous genetic sequence of TGFβRIII, in particular by using a rare cutting endonuclease, such as a TALE-nuclease or RNA-guided endonuclease (e.g.: Cas9 or Cpf1).

An anti-TGFβRII $IgG_1$ monoclonal antibody that inhibits receptor-mediated signaling activation such as LY3022859 [Tolcher, A. W. et al. (2017) A phase 1 study of anti-TGFβ receptor type-II monoclonal antibody LY3022859 in patients with advanced solid tumors *Cancer Chemother Pharmacol.* 79(4):673-680] can also be used to inhibit TGFbeta receptor signalling in combination of the CAR as per the present invention.

The present application discloses herein a selection of TALE-nucleases, which are particularly specific to a selection of target sequences within the TGFβRII gene. These TALE-nucleases have displayed highest TGFβRII knockout efficiency with very little off-target cleavage resulting into large populations of viable engineered cells, sufficient for dosing several patients. These preferred TALE-nuclease and their corresponding target sequences are listed in Table 6.

TABLE 6

TALE-nuclease target sequences for TGFβRII gene.

| TALEN | Target Sequence into TGFβRII gene |
|---|---|
| T003387 | TTTTGTTTCCCCATCAGAATATAACACCAGCAATCCTGACTTGTTGCTA (SEQ ID NO: 36) |
| T003401 | TCCCTATGAGGAGTATGCCTCTTGGAAGACAGAGAAGGACATC TTCTCA (SEQ ID NO: 37) |
| T003400 | TGGCAGTCAAGATCTTTCCCTATGAGGAGTATGCCTCTTGGAA GACAGA (SEQ ID NO: 38) |
| T003405 | TGTGGGAGGCCCAAGATGCCCATCGTGCACAGGGACCTCAAG AGCTCCA (SEQ ID NO: 39) |

RNA guides avec also been designed to inactivate TGFβRII gene by using Cas9 nuclease reagent. Their corresponding respective target sequences are disclosed in Table 7.

TABLE 7

CRISPR target sequences for TGFβRII gene.

| sgRNA Sequence | sgRNA Sequence with PAM | SEQ ID NO:# | PAM Sequence |
|---|---|---|---|
| ACAGTGATCACACTCCATGT | ACAGTGATCACACTCCATGTGGG | 40 | GGG |
| GCAGAAGCTGAGTTCAACCT | GCAGAAGCTGAGTTCAACCTGGG | 41 | GGG |
| AGGTTAGGTCGTTCTTCACG | AGGTTAGGTCGTTCTTCACGAGG | 42 | AGG |
| AAAGCGACCTTTCCCCACCA | AAAGCGACCTTTCCCCACCAGGG | 43 | GGG |
| TGGATGACCTGGCTAACAGT | TGGATGACCTGGCTAACAGTGGG | 44 | GGG |
| CCTGGGAAACCGGCAAGACG | CCTGGGAAACCGGCAAGACGCGG | 45 | CGG |
| ACAGATATGGCAACTCCCAG | ACAGATATGGCAACTCCCAGTGG | 46 | TGG |
| GTGGAGGTGAGCAATCCCCC | GTGGAGGTGAGCAATCCCCCGGG | 47 | GGG |
| ACCTACAGGAGTACCTGACG | ACCTACAGGAGTACCTGACGCGG | 48 | CGG |
| GTGATCACACTCCATGTGGG | GTGATCACACTCCATGTGGGAGG | 49 | AGG |
| GCTGGTGTTATATTCTGATG | GCTGGTGTTATATTCTGATGGGG | 50 | GGG |
| CACAGTGATCACACTCCATG | CACAGTGATCACACTCCATGTGG | 51 | TGG |
| CACATGGAGTGTGATCACTG | CACATGGAGTGTGATCACTGTGG | 52 | TGG |
| CAGAGTAGGGTCCAGACGCA | CAGAGTAGGGTCCAGACGCAGGG | 53 | GGG |
| GCTTCTGCTGCCGGTTAACG | GCTTCTGCTGCCGGTTAACGCGG | 54 | CGG |
| GTGGATGACCTGGCTAACAG | GTGGATGACCTGGCTAACAGTGG | 55 | TGG |
| GGGAAAGCCCAAAGTCACAC | GGGAAAGCCCAAAGTCACACAGG | 56 | AGG |
| AATATGACTAGCAACAAGTC | AATATGACTAGCAACAAGTCAGG | 57 | AGG |
| ATGGAGTGTGATCACTGTGG | ATGGAGTGTGATCACTGTGGAGG | 58 | AGG |
| ATCACCGCCTTCCACGCCAA | ATCACCGCCTTCCACGCCAAGGG | 59 | GGG |
| AGGAGCGGAAGACGGAGTTG | AGGAGCGGAAGACGGAGTTGGGG | 60 | GGG |
| CCACGCCAAGGGCAACCTAC | CCACGCCAAGGGCAACCTACAGG | 61 | AGG |
| CAAGATGCCCATCGTGCACA | CAAGATGCCCATCGTGCACAGGG | 62 | GGG |
| GATATGGCAACTCCCAGTGG | GATATGGCAACTCCCAGTGGTGG | 63 | TGG |
| AGCAGAAGCTGAGTTCAACC | AGCAGAAGCTGAGTTCAACCTGG | 64 | TGG |
| CCTGTAGGTTGCCCTTGGCG | CCTGTAGGTTGCCCTTGGCGTGG | 65 | TGG |
| GTGAGCAATCCCCCGGGCGA | GTGAGCAATCCCCCGGGCGAGGG | 66 | GGG |
| ACAGAGTAGGGTCCAGACGC | ACAGAGTAGGGTCCAGACGCAGG | 67 | AGG |
| GACGCGGCATGTCATCAGCT | GACGCGGCATGTCATCAGCTGGG | 109 | GGG |
| GGTCATCCACAGACAGAGTA | GGTCATCCACAGACAGAGTAGGG | 110 | GGG |
| AGTCAAGATCTTTCCCTATG | AGTCAAGATCTTTCCCTATGAGG | 111 | AGG |
| GAACATACTCCAGTTCCTGA | GAACATACTCCAGTTCCTGACGG | 112 | CGG |
| ACGTGGAGCTGATGTCAGAG | ACGTGGAGCTGATGTCAGAGCGG | 113 | CGG |
| GGGGAAAGGTCGCTTTGCTG | GGGGAAAGGTCGCTTTGCTGAGG | 114 | AGG |
| TCTGGACCCTACTCTGTCTG | TCTGGACCCTACTCTGTCTGTGG | 115 | TGG |

TABLE 7-continued

CRISPR target sequences for TGFβRII gene.

| sgRNA Sequence | sgRNA Sequence with PAM | SEQ ID NO:# | PAM Sequence |
|---|---|---|---|
| TGGGCAGCTCCCTCGCCCGG | TGGGCAGCTCCCTCGCCCGGGGG | 116 | GGG |
| AGCTGATGACATGCCGCGTC | AGCTGATGACATGCCGCGTCAGG | 117 | AGG |
| GCCGCGTCAGGTACTCCTGT | GCCGCGTCAGGTACTCCTGTAGG | 118 | AGG |
| CAAGAGGCATACTCCTCATA | CAAGAGGCATACTCCTCATAGGG | 119 | GGG |
| GGTGAGCAATCCCCCGGGCG | GGTGAGCAATCCCCCGGGCGAGG | 120 | AGG |
| TTGCTGGTGTTATATTCTGA | TTGCTGGTGTTATATTCTGATGG | 121 | TGG |
| CCTATGAGGAGTATGCCTCT | CCTATGAGGAGTATGCCTCTTGG | 122 | TGG |
| TGCTGGTGTTATATTCTGAT | TGCTGGTGTTATATTCTGATGGG | 123 | GGG |
| CGAGGATATTGGAGCTCTTG | CGAGGATATTGGAGCTCTTGAGG | 124 | AGG |
| GTTGATGTTGTTGGCACACG | GTTGATGTTGTTGGCACACGTGG | 125 | TGG |
| TGACGCGGCATGTCATCAGC | TGACGCGGCATGTCATCAGCTGG | 126 | TGG |
| TTGAGCTGGACACCCTGGTG | TTGAGCTGGACACCCTGGTGGGG | 127 | GGG |
| TTCAGAGCAGTTTGAGACAG | TTCAGAGCAGTTTGAGACAGTGG | 128 | TGG |
| GCGGCATGTCATCAGCTGGG | GCGGCATGTCATCAGCTGGGAGG | 129 | AGG |
| AGGTCATCCACAGACAGAGT | AGGTCATCCACAGACAGAGTAGG | 130 | AGG |
| GAAGATGATGATGACAGATA | GAAGATGATGATGACAGATATGG | 131 | TGG |
| TGACCTGGCTAACAGTGGGC | TGACCTGGCTAACAGTGGGCAGG | 132 | AGG |
| TCTACTGCTACCGCGTTAAC | TCTACTGCTACCGCGTTAACCGG | 133 | CGG |
| GTCCTTCTCTGTCTTCCAAG | GTCCTTCTCTGTCTTCCAAGAGG | 134 | AGG |
| ATTGAGCTGGACACCCTGGT | ATTGAGCTGGACACCCTGGTGGG | 135 | GGG |
| GTCGTTCTTCACGAGGATAT | GTCGTTCTTCACGAGGATATTGG | 136 | TGG |
| CATCAGCCTCCTGCCACCAC | CATCAGCCTCCTGCCACCACTGG | 137 | TGG |
| AGTTCCTGACGGCTGAGGAG | AGTTCCTGACGGCTGAGGAGCGG | 138 | CGG |
| ACTCCAGTTCCTGACGGCTG | ACTCCAGTTCCTGACGGCTGAGG | 139 | AGG |
| CTTGAGGTCCCTGTGCACGA | CTTGAGGTCCCTGTGCACGATGG | 140 | TGG |
| TTGAGGTCCCTGTGCACGAT | TTGAGGTCCCTGTGCACGATGGG | 141 | GGG |
| CCGCGTCTTGCCGGTTTCCC | CCGCGTCTTGCCGGTTTCCCAGG | 142 | AGG |
| GTTGCCCTTGGCGTGGAAGG | GTTGCCCTTGGCGTGGAAGGCGG | 143 | CGG |
| CTTTGGGCTTTCCCTGCGTC | CTTTGGGCTTTCCCTGCGTCTGG | 144 | TGG |
| GATCACCGCCTTCCACGCCA | GATCACCGCCTTCCACGCCAAGG | 145 | AGG |
| TGAAGTGTTCTGCTTCAGCT | TGAAGTGTTCTGCTTCAGCTTGG | 146 | TGG |
| CTGTGCACGATGGGCATCTT | CTGTGCACGATGGGCATCTTGGG | 147 | GGG |
| GGCATCTTGGGCCTCCCACA | GGCATCTTGGGCCTCCCACATGG | 148 | TGG |
| TTACCTGCCCACTGTTAGCC | TTACCTGCCCACTGTTAGCCAGG | 149 | AGG |
| ATCAGCCTCCTGCCACCACT | ATCAGCCTCCTGCCACCACTGGG | 150 | GGG |
| TCGCTTTGCTGAGGTCTATA | TCGCTTTGCTGAGGTCTATAAGG | 151 | AGG |
| AGTCACACAGGCAGCAGGTT | AGTCACACAGGCAGCAGGTTAGG | 152 | AGG |
| GAGGAGCGGAAGACGGAGTT | GAGGAGCGGAAGACGGAGTTGGG | 153 | GGG |

TABLE 7-continued

| CRISPR target sequences for TGFβRII gene. | | | |
|---|---|---|---|
| sgRNA Sequence | sgRNA Sequence with PAM | SEQ ID NO:# | PAM Sequence |
| TGGGCAGCAGCTCTGTGTTG | TGGGCAGCAGCTCTGTGTTGTGG | 154 | TGG |
| TAGCAACAAGTCAGGATTGC | TAGCAACAAGTCAGGATTGCTGG | 68 | TGG |
| CCAAGATGCCCATCGTGCAC | CCAAGATGCCCATCGTGCACAGG | 69 | AGG |
| TGTGGAGGTGAGCAATCCCC | TGTGGAGGTGAGCAATCCCCCGG | 70 | CGG |
| TGCCTCTTGGAAGACAGAGA | TGCCTCTTGGAAGACAGAGAAGG | 71 | AGG |
| GCCCATTGAGCTGGACACCC | GCCCATTGAGCTGGACACCCTGG | 72 | TGG |
| CTGAGTTCAACCTGGGAAAC | CTGAGTTCAACCTGGGAAACCGG | 73 | CGG |
| TGGGAGGACCTGCGCAAGCT | TGGGAGGACCTGCGCAAGCTGGG | 74 | GGG |
| GTACTCCTGTAGGTTGCCCT | GTACTCCTGTAGGTTGCCCTTGG | 75 | TGG |
| TCTTCCGCTCCTCAGCCGTC | TCTTCCGCTCCTCAGCCGTCAGG | 76 | AGG |
| CTGGGCAGCTCCCTCGCCCG | CTGGGCAGCTCCCTCGCCCGGGG | 77 | GGG |
| CATTGAGCTGGACACCCTGG | CATTGAGCTGGACACCCTGGTGG | 78 | TGG |
| TGGCAACTCCCAGTGGTGGC | TGGCAACTCCCAGTGGTGGCAGG | 79 | AGG |
| CAACTCCCAGTGGTGGCAGG | CAACTCCCAGTGGTGGCAGGAGG | 80 | AGG |
| CGAGCACTGTGCCATCATCC | CGAGCACTGTGCCATCATCCTGG | 81 | TGG |
| GCGGTCATCTTCCAGGATGA | GCGGTCATCTTCCAGGATGATGG | 82 | TGG |
| AGAGCTGCTGCCCATTGAGC | AGAGCTGCTGCCCATTGAGCTGG | 83 | TGG |
| ACCAGGGTGTCCAGCTCAAT | ACCAGGGTGTCCAGCTCAATGGG | 84 | GGG |
| CTGGACACCCTGGTGGGGAA | CTGGACACCCTGGTGGGGAAAGG | 85 | AGG |
| CAAAGCGACCTTTCCCCACC | CAAAGCGACCTTTCCCCACCAGG | 86 | AGG |
| GACGGCTGAGGAGCGGAAGA | GACGGCTGAGGAGCGGAAGACGG | 87 | CGG |
| TACTCTGTCTGTGGATGACC | TACTCTGTCTGTGGATGACCTGG | 88 | TGG |
| CGGCAAGACGCGGAAGCTCA | CGGCAAGACGCGGAAGCTCATGG | 89 | TGG |
| CCCAAAGTCACACAGGCAGC | CCCAAAGTCACACAGGCAGCAGG | 90 | AGG |
| TAGGTTGCCCTTGGCGTGGA | TAGGTTGCCCTTGGCGTGGAAGG | 91 | AGG |
| TGAGGAGCGGAAGACGGAGT | TGAGGAGCGGAAGACGGAGTTGG | 92 | TGG |
| CCTGTGCACGATGGGCATCT | CCTGTGCACGATGGGCATCTTGG | 93 | TGG |
| GGGAGCTGCCCAGCTTGCGC | GGGAGCTGCCCAGCTTGCGCAGG | 94 | AGG |
| TTGAACTCAGCTTCTGCTGC | TTGAACTCAGCTTCTGCTGCCGG | 95 | CGG |
| CCAAGAGGCATACTCCTCAT | CCAAGAGGCATACTCCTCATAGG | 96 | AGG |
| CATGAGCTTCCGCGTCTTGC | CATGAGCTTCCGCGTCTTGCCGG | 97 | CGG |
| CGGAGTTGGGGAAACAATAC | CGGAGTTGGGGAAACAATACTGG | 98 | TGG |
| GCTCCTCAGCCGTCAGGAAC | GCTCCTCAGCCGTCAGGAACTGG | 99 | TGG |
| CACCAGGGTGTCCAGCTCAA | CACCAGGGTGTCCAGCTCAATGG | 100 | TGG |
| CTAGTCATATTTCAAGTGAC | CTAGTCATATTTCAAGTGACAGG | 101 | AGG |
| GCTGGGCAGCTCCCTCGCCC | GCTGGGCAGCTCCCTCGCCCGGG | 102 | GGG |
| TGTCAGAGCGGTCATCTTCC | TGTCAGAGCGGTCATCTTCCAGG | 103 | AGG |
| CTGGGAGGACCTGCGCAAGC | CTGGGAGGACCTGCGCAAGCTGG | 104 | TGG |

TABLE 7-continued

CRISPR target sequences for TGFβRII gene.

| sgRNA Sequence | sgRNA Sequence with PAM | SEQ ID NO:# | PAM Sequence |
|---|---|---|---|
| AGCTGGGCAGCTCCCTCGCC | AGCTGGGCAGCTCCCTCGCCCGG | 105 | CGG |
| TGTGTTGTGGTTGATGTTGT | TGTGTTGTGGTTGATGTTGTTGG | 106 | TGG |
| CCTGCTGCCTGTGTGACTTT | CCTGCTGCCTGTGTGACTTTGGG | 107 | GGG |
| ACCTGCTGCCTGTGTGACTT | ACCTGCTGCCTGTGTGACTTTGG | 108 | TGG |

The present invention thus encompasses the use of a TALE-nuclease or RNA-guided endonuclease designed to bind any of the target sequences SEQ ID NO:X to Y referred to in table 5 or 6 for the inactivation or reducing of expression of TGFβRII for the production of therapeutic immune cells within the teaching of the present specification.

The present invention also pertains to engineered immune cells comprising an exogenous polynucleotide encoding a nuclease, such as one referred to before, to inactivate or reduce the expression of its endogenous TGFβRII gene.

The present application thus reports engineered immune cells, especially CAR immune cells, into which an exogenous sequence encoding an inhibitor of TGFbeta receptor has been introduced, more particularly a sequence encoding a dominant negative TGFbeta receptor. Such cells are more particularly dedicated to the treatment of solid tumors, especially MSLN positive tumors.

Accordingly, the present application also claims vectors, especially viral vectors, such as lentiviral vectors or AAV vectors as described in the art, comprising at least a polynucleotide sequence encoding a dominant negative TGFβRII, and optionally, a mesothelin-specific chimeric antigen receptor. In preferred embodiments, said vectors comprise a first polynucleotide sequence encoding said dominant negative TGFβRII, a second polynucleotide sequence encoding 2A self-cleaving peptide and a third one encoding said mesothelin-specific chimeric antigen receptor.

Targeted insertion into immune cells can be significantly improved by using AAV vectors, especially vectors from the AAV6 family or chimeric vectors AAV2/6 previously described by Sharma A., et al. [Transduction efficiency of AAV 2/6, 2/8 and 2/9 vectors for delivering genes in human corneal fibroblasts. (2010) *Brain Research Bulletin.* 81 (2-3): 273-278].

One aspect of the present invention is thus the transduction of AAV vectors comprising MSLN-CAR coding sequence in human primary immune cells, in conjunction with the expression of sequence-specific endonuclease reagents, such as TALE endonucleases, to increase gene integration at the loci previously cited.

According to a preferred aspect of the invention, sequence specific endonuclease reagents can be introduced into the cells by transfection, more preferably by electroporation of mRNA encoding said sequence specific endonuclease reagents.

The obtained insertion of the exogenous nucleic acid sequence may result into the introduction of genetic material, correction or replacement of the endogenous sequence, more preferably "in frame" with respect to the endogenous gene sequences at that locus.

According to another aspect of the invention, from $10^5$ to $10^7$, preferably from $10^6$ to $10^7$, more preferably about $5 \cdot 10^6$ viral genomes viral genomes are transduced per cell.

According to another aspect of the invention, the cells can be treated with proteasome inhibitors, such as Bortezomib or HDAC inhibitors to further help homologous recombination.

As one object of the present invention, the AAV vector used in the method can comprise an exogenous coding sequence that is promoter less, said coding sequence being any of those referred to in this specification.

The present invention also provides with an efficient method for obtaining primary immune cells, which can be gene edited in various gene loci more particularly involved into host-graft interaction and recognition. Other loci may also be edited in view of improving the activity, the survival or the life-time of the engineered primary cells, especially primary T cells.

FIG. 2 maps the main cell functions that can be modified by gene editing according to the present invention to improve the efficiency of the engineered immune cells. Any gene inactivation listed under each function can be combined with another to obtain a synergistic effect on the overall therapeutic potency of the immune cells.

The present invention provides more particularly with combinations of genetic modifications (genotypes) into immune cells prompt to improve immune cells potency against solid tumor, especially against MSLN positive malignant cells, such as:

[MSLN-CAR]$^+$,
[MSLN-CAR]$^+$[dnTGFβRII]$^+$
[MSLN-CAR]$^+$[dnTGFβRII]$^+$[TCR]$^-$,
[MSLN-CAR]$^+$[dnTGFβRII]$^+$[TGFβRII]$^-$[TCR]$^-$,
[MSLN-CAR]$^+$[TGFβRII]$^-$,
[MSLN-CAR]$^+$[TGFβRII]$^-$[TCR]$^-$,
[MSLN-CAR]$^+$[β2m]$^-$,
[MSLN-CAR]$^+$[dnTGFβRII]+[β2m]$^-$,
[MSLN-CAR]$^+$[TGFβRII]$^-$[β2m]$^-$,
[MSLN-CAR]$^+$[dnTGFβRII]$^+$[β2m]$^-$[TCR]$^-$,
[MSLN-CAR]$^+$[TGFβRII]$^-$[β2m]$^-$[TCR]$^-$,
[MSLN-CAR]$^+$[dnTGFβRII]$^+$[TGFβRII]$^-$[β2m]$^-$[TCR]$^-$,
[MSLN-CAR]$^+$[PD1]$^-$,
[MSLN-CAR]$^+$[TGFβRII]$^-$[PD1]$^-$,
[MSLN-CAR]$^+$[dnTGFβRII]$^+$[PD1]$^-$,
[MSLN-CAR]$^+$[dnTGFβRII]$^+$[TGFβRII]$^-$[PD1]$^-$,
[MSLN-CAR]$^+$[dnTGFβRII]$^+$[β2m]$^-$[PD1]$^-$,
[MSLN-CAR]$^+$[TGFβRII]$^-$[PD1]$^-$[TCR]$^-$,
[MSLN-CAR]$^+$[dnTGFβRII]$^+$[TGFβRII]$^-$[PD1]$^-$[TCR]$^-$,
[MSLN-CAR]$^+$[PD1]$^-$[β2m]$^-$,
[MSLN-CAR]$^+$[TGFβRII]$^-$[PD1]$^-$[β2m]$^-$,
[MSLN-CAR]$^+$[dnTGFβRII]$^+$[PD1]$^-$[β2m]$^-$,
[MSLN-CAR]$^+$[dnTGFβRII]$^+$[TGFβRII]$^-$[PD1]$^-$[β2m]$^-$,

[MSLN-CAR]$^+$[dnTGFβRII]$^+$[β2m]$^-$[PD1]$^-$[TCR]$^-$,
[MSLN-CAR]$^+$[TGFβRII]$^-$[PD1]$^-$[TCR]$^-$[β2m]$^-$,
[MSLN-CAR]$^+$[dnTGFβRII]$^+$[TGFβRII]$^-$[PD1]$^-$[TCR]$^-$[β2m]$^-$.

As mentioned before, the present invention is also particularly focused on the use of CAR positive cells in solid cancer treatments, which are made resistant to lymphodepleting agents, so that they can be combined with or preceded by lymphodepletion regimen for their use in allogeneic settings. Such cells preferably display the following genotypes:

with respect to anti-CD52 antibody partial or complete tolerance:
[MSLN-CAR]$^+$[CD52]$^-$[TCR]$^-$,
[MSLN-CAR]$^+$[CD52]$^-$[TCR]$^-$[β2m]$^-$,
[MSLN-CAR]$^+$[TGFβRII]$^-$[CD52]$^-$[TCR]$^-$,
[MSLN-CAR]$^+$[TGFβRII]$^-$[CD52]$^-$[TCR]$^-$[β2m]$^-$,
[MSLN-CAR]$^+$[dnTGFβRII]$^+$[CD52]$^-$[TCR]$^-$,
[MSLN-CAR]$^+$[dnTGFβRII]$^+$[CD52]$^-$[TCR]$^-$[β2m]$^-$, with respect to purine analogues partial or complete tolerance:
[MSLN-CAR]$^+$[DCK]$^-$[TCR]$^-$,
[MSLN-CAR]$^+$[DCK]$^-$[TCR]$^-$[β2m]$^-$,
[MSLN-CAR]$^+$[TGFβRII]$^-$[DCK]$^-$[TCR]$^-$,
[MSLN-CAR]$^+$[TGFβRII]$^-$[DCK]$^-$[TCR]$^-$[β2m]$^-$,
[MSLN-CAR]$^+$[dnTGFβRII]$^+$[DCK]$^-$[TCR]$^-$,
[MSLN-CAR]$^+$[dnTGFβRII]$^+$[DCK]$^-$[TCR]$^-$[β2m]$^-$, with respect to glucocorticoids partial or complete tolerance:
[MSLN-CAR]$^+$[GR]$^-$[TCR]$^-$,
[MSLN-CAR]$^+$[GR]$^-$[TCR]$^-$[β2m]$^-$,
[MSLN-CAR]$^+$[TGFβRII]$^-$[GR]$^-$[TCR]$^-$,
[MSLN-CAR]$^+$[TGFβRII]$^-$[GR]$^-$[TCR]$^-$[β2m]$^-$,
[MSLN-CAR]$^+$[dnTGFβRII]$^+$[GR]$^-$[TCR]$^-$,
[MSLN-CAR]$^+$[dnTGFβRII]$^+$[GR]$^-$[TCR]$^-$[β2m]$^-$, Further Improving Therapeutic Immune Cells by Expression of Transgenes at Inactivated Loci The above preferred genotypes can be obtained by gene targeting integration, preferably at the PD1, TCR (TCRalpha and/or TCRbeta) or TGFβRII loci, but also at further selected loci as described here after.

By "gene targeting integration" is meant any known site-specific methods allowing to insert, replace or correct a genomic sequence into a living cell. Gene targeted integration usually involves the mechanisms of homologous gene recombination or NHEJ (Non homologous Ends Joining), which are enhanced by endonuclease sequence specific reagents, to result into insertion or replacement of at least one exogenous nucleotide, preferably a sequence of several nucleotides (i.e. polynucleotide), and more preferably a coding sequence at a predefined locus.

The method of the present invention can be associated with other methods involving genetic transformations, such as a viral transduction, and also may be combined with other transgene expression not necessarily involving integration.

According to one aspect, the method according to the invention comprises the steps of introducing into an immune cell a mutation or polynucleotide coding sequence at an endogenous locus selected from:

a) polynucleotide sequence(s), which expression is(are) involved into reduction of glycolysis and calcium signaling in response to a low glucose condition, such as SERCA3 to increase calcium signaling, miR101 and mir26A to increase glycolysis, BCAT to mobilize glycolytic reserves; and/or
b) polynucleotide sequence(s), which expression up regulate(s) immune checkpoint proteins (e.g. TIM3, CEACAM, LAG3, TIGIT), such as IL27RA, STAT1, STAT3; and/or
c) polynucleotide sequence(s), which expression mediate(s) interaction with HLA-G, such as ILT2 or ILT4; and/or
d) polynucleotide sequence(s), which expression is(are) involved into the down regulation of T-cell proliferation such as SEMA7A, SHARPIN to reduce Treg proliferation, STAT1 to lower apoptosis, PEA15 to increase IL-2 secretion and RICTOR to favor CD8 memory differentiation; and/or
e) polynucleotide sequence(s), which expression is(are) involved into the down regulation of T-cell activation, such as mir21; and/or
f) polynucleotide sequence(s), which expression is(are) involved in signaling pathways responding to cytokines, such as JAK2 and AURKA; and/or
g) polynucleotide sequence(s), which expression is(are) involved in T-cell exhaustion, such as DNMT3, miRNA31, MT1A, MT2A, PTGER2;

preferably, by expressing into said cell a sequence-specific reagent that specifically targets said selected endogenous locus.

Said transgene or exogenous polynucleotide sequence is preferably inserted so that its expression is placed under transcriptional control of at least one endogenous promoter present at one of said locus.

Targeting one locus as referred to above by performing gene integration is beneficial to further improve the potency of the therapeutic immune cells of the invention.

Examples of such exogenous sequences or transgenes that can be expressed or overexpressed at the selected loci are given hereafter:

Expression of Transgenes Conferring Resistance to Drugs or Immune Depletion Agents According to one aspect of the present method, the exogenous sequence that is integrated into the immune cells genomic locus encodes a molecule that confers resistance of said immune cells to a drug.

Examples of preferred exogenous sequences are variants of dihydrofolate reductase (DHFR) conferring resistance to folate analogs such as methotrexate, variants of inosine monophosphate dehydrogenase 2 (IMPDH2) conferring resistance to IMPDH inhibitors such as mycophenolic acid (MPA) or its prodrug mycophenolate mofetil (MMF), variants of calcineurin or methylguanine transferase (MGMT) conferring resistance to calcineurin inhibitor such as FK506 and/or CsA, variants of mTOR such as mTORmut conferring resistance to rapamycin) and variants of Lck, such as Lckmut conferring resistance to Imatinib and Gleevec.

The term "drug" is used herein as referring to a compound or a derivative thereof, preferably a standard chemotherapy agent that is generally used for interacting with a cancer cell, thereby reducing the proliferative or living status of the cell. Examples of chemotherapeutic agents include, but are not limited to, alkylating agents (e.g., cyclophosphamide, ifosamide), metabolic antagonists (e.g., purine nucleoside antimetabolite such as clofarabine, fludarabine or 2'-deoxyadenosine, methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

As used herein, an immune cell is made "resistant or tolerant" to a drug when said cell, or population of cells is modified so that it can proliferate, at least in-vitro, in a culture medium containing half maximal inhibitory concentration (IC50) of said drug (said IC50 being determined with respect to an unmodified cell(s) or population of cells).

In a particular embodiment, said drug resistance can be conferred to the immune cells by the expression of at least one "drug resistance coding sequence". Said drug resistance coding sequence refers to a nucleic acid sequence that confers "resistance" to an agent, such as one of the chemotherapeutic agents referred to above. A drug resistance coding sequence of the invention can encode resistance to anti-metabolite, methotrexate, vinblastine, cisplatin, alkylating agents, anthracyclines, cytotoxic antibiotics, anti-immunophilins, their analogs or derivatives, and the like (Takebe, N., S. C. Zhao, et al. (2001) "Generation of dual resistance to 4-hydroperoxycyclophosphamide and methotrexate by retroviral transfer of the human aldehyde dehydrogenase class 1 gene and a mutated dihydrofolate reductase gene". *Mol. Ther.* 3(1): 88-96), (Zielske, S. P., J. S. Reese, et al. (2003) "In vivo selection of MGMT(P140K) lentivirus-transduced human NOD/SCID repopulating cells without pretransplant irradiation conditioning." *J. Clin. Invest.* 112 (10): 1561-70) (Nivens, M. C., T. Felder, et al. (2004) "Engineered resistance to camptothecin and antifolates by retroviral coexpression of tyrosyl DNA phosphodiesterase-I and thymidylate synthase" Cancer Chemother Pharmacol 53(2): 107-15), (Bardenheuer, W., K. Lehmberg, et al. (2005). "Resistance to cytarabine and gemcitabine and in vitro selection of transduced cells after retroviral expression of cytidine deaminase in human hematopoietic progenitor cells". *Leukemia* 19(12): 2281-8), (Kushman, M. E., S. L. Kabler, et al. (2007) "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1" *Carcinogenesis* 28(1): 207-14).

The expression of such drug resistance exogenous sequences in the immune cells as per the present invention more particularly allows the use of said immune cells in cell therapy treatment schemes where cell therapy is combined with chemotherapy or into patients previously treated with these drugs.

Several drug resistance coding sequences have been identified that can potentially be used to confer drug resistance according to the invention. One example of drug resistance coding sequence can be for instance a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance coding sequence according to the present invention can be a nucleic acid sequence encoding a mutant form of human wild type DHFR (GenBank: AAH71996.1), which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer et al. (1990) "Dihydrofolate reductase as a therapeutic target" *Faseb J* 4(8): 2441-52; International application WO94/24277; and U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

Another example of drug resistance coding sequence can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (Genebank: NP_000875.2) leading to a significantly increased resistance to IMPDH inhibitor. Mutations in these variants are preferably at positions T333 and/or S351 (Yam, P., M. Jensen, et al. (2006) "Ex vivo selection and expansion of cells based on expression of a mutated inosine monophosphate dehydrogenase 2 after HIV vector transduction: effects on lymphocytes, monocytes, and CD34+ stem cells" *Mol. Ther.* 14(2): 236-44) (Jonnalagadda, M., et al. (2013) "Engineering human T cells for resistance to methotrexate and mycophenolate mofetil as an in vivo cell selection strategy." *PLoS One* 8(6): e65519).

Another drug resistance coding sequence is the mutant form of calcineurin. Calcineurin (PP2B—NCBI: ACX34092.1) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin et al. (2009) "Generation of EBV-specific cytotoxic T cells that are resistant to calcineurin inhibitors for the treatment of post-transplantation lymphoproliferative disease" *Blood* 114(23): 4792-803). In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue. In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagines at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence. Correspondence of amino acid positions described herein is frequently expressed in terms of the positions of the amino acids of the form of wild-type human calcineurin heterodimer b polypeptide (NCBI: ACX34095.1).

Another drug resistance coding sequence is O(6)-methylguanine methyltransferase (MGMT—UniProtKB: P16455) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, R. et al. (1999) "Retroviral-mediated expression of the P140A, but not P140A/G156A, mutant form of O6-methylguanine DNA methyltransferase protects hematopoietic cells against O6-benzylguanine sensitization to chloroethylnitrosourea treatment" J. Pharmacol. Exp. Ther. 290(3): 1467-74). In a particular embodiment, AGT mutant form can comprise a mutated amino acid of the wild type AGT position P140. In a preferred embodiment, said proline at position 140 is replaced with a lysine residue.

Another drug resistance coding sequence can be multidrug resistance protein (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (Genebank NP_000918).

Another drug resistance coding sequence can contribute to the production of cytotoxic antibiotics, such as those from ble or mcrA genes. Ectopic expression of ble gene or mcrA in an immune cell gives a selective advantage when exposed to the respective chemotherapeutic agents bleomycine and mitomycin C (Belcourt, M. F. (1999) "Mitomycin resistance in mammalian cells expressing the bacterial mitomycin C resistance protein MCRA". *PNAS.* 96(18):10489-94).

Another drug resistance coding sequence can come from genes encoded mutated version of drug targets, such as mutated variants of mTOR (mTOR mut) conferring resistance to rapamycin such as described by Lorenz M. C. et al. (1995) "TOR Mutations Confer Rapamycin Resistance by Preventing Interaction with FKBP12-Rapamycin" *The Journal of Biological Chemistry* 270, 27531-27537, or certain mutated variants of Lck (Lckmut) conferring resistance to Gleevec as described by Lee K. C. et al. (2010) "Lck is a key target of imatinib and dasatinib in T-cell activation", *Leukemia,* 24: 896-900.

As described above, the genetic modification step of the method can comprise a step of introduction into cells of an exogeneous nucleic acid comprising at least a sequence encoding the drug resistance coding sequence and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Expression of Transgene Enhancing Persistence of the Immune Cells In-Vivo

According to one aspect of the present method, the exogenous sequence that is integrated into the immune cells genomic locus encodes a molecule that enhances persistence of the immune cells, especially in-vivo persistence in a tumor environment.

By "enhancing persistence" is meant extending the survival of the immune cells in terms of life span, especially once the engineered immune cells are injected into the patient. For instance, persistence is enhanced, if the mean survival of the modified cells is significantly longer than that of non-modified cells, by at least 10%, preferably 20%, more preferably 30%, even more preferably 50%.

This especially relevant when the immune cells are allogeneic. This may be done by creating a local immune protection by introducing coding sequences that ectopically express and/or secrete immunosuppressive polypeptides at, or through, the cell membrane. A various panel of such polypeptides in particular antagonists of immune checkpoints, immunosuppressive peptides derived from viral envelope or NKG2D ligand can enhance persistence and/or an engraftment of allogeneic immune cells into patients.

According to one embodiment, the immunosuppressive polypeptide to be encoded by said exogenous coding sequence is a ligand of Cytotoxic T-Lymphocyte Antigen 4 (CTLA-4 also known as CD152, GenBank accession number AF414120.1). Said ligand polypeptide is preferably an anti-CTLA-4 immunoglobulin, such as CTLA-4a Ig and CTLA-4b Ig or a functional variant thereof.

According to one embodiment, the immunosuppressive polypeptide to be encoded by said exogenous coding sequence is an antagonist of PD1, such as PD-L1 (other names: CD274, Programmed cell death 1 ligand; ref. UniProt for the human polypeptide sequence Q9NZQ7), which encodes a type I transmembrane protein of 290 amino acids consisting of a Ig V-like domain, a Ig C-like domain, a hydrophobic transmembrane domain and a cytoplasmic tail of 30 amino acids. Such membrane-bound form of PD-L1 ligand is meant in the present invention under a native form (wild-type) or under a truncated form such as, for instance, by removing the intracellular domain, or with one or more mutation(s) (Wang S et al., 2003, *J Exp Med.* 2003; 197(9): 1083-1091). Of note, PD1 is not considered as being a membrane-bound form of PD-L1 ligand according to the present invention. According to another embodiment, said immunosuppressive polypeptide is under a secreted form. Such recombinant secreted PD-L1 (or soluble PD-L1) may be generated by fusing the extracellular domain of PD-L1 to the Fc portion of an immunoglobulin (Haile S T et al., 2014, *Cancer Immunol. Res.* 2(7): 610-615; Song M Y et al., 2015, *Gut.* 64(2):260-71). This recombinant PD-L1 can neutralize PD-1 and abrogate PD-1-mediated T-cell inhibition. PD-L1 ligand may be co-expressed with CTLA4 Ig for an even enhanced persistence of both.

According to another embodiment, the exogenous sequence encodes a non-human MHC homolog, especially a viral MHC homolog, or a chimeric β2m polypeptide such as described by Margalit A. et al. (2003) "Chimeric β2 microglobulin/CD3ζ polypeptides expressed in T cells convert MHC class I peptide ligands into T cell activation receptors: a potential tool for specific targeting of pathogenic CD8+ T cells" Int. Immunol. 15 (11): 1379-1387.

According to one embodiment, the exogenous sequence encodes NKG2D ligand. Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A et al. (2003) "Selective intracellular retention of virally induced NKG2D ligands by the human cytomegalovirus UL16 glycoprotein". *Eur. J. Immunol.,* 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. *Blood* 102: 1389-1396).

According to one embodiment, the exogenous sequence encodes a cytokine receptor, such as an IL-12 receptor. IL-12 is a well known activator of immune cells activation (Curtis J. H. (2008) "IL-12 Produced by Dendritic Cells Augments CD8+ T Cell Activation through the Production of the Chemokines CCL1 and CCL171". *The Journal of Immunology.* 181 (12): 8576-8584.

According to one embodiment the exogenous sequence encodes an antibody that is directed against inhibitory peptides or proteins. Said antibody is preferably be secreted under soluble form by the immune cells. Nanobodies from shark and camels are advantageous in this respect, as they are structured as single chain antibodies (Muyldermans S. (2013) "Nanobodies: Natural Single-Domain Antibodies" *Annual Review of Biochemistry* 82: 775-797). Same are also deemed more easily to fuse with secretion signal polypeptides and with soluble hydrophilic domains.

The different aspects developed above to enhance persistence of the cells are particularly preferred, when the exogenous coding sequence is introduced by disrupting an endogenous gene encoding β2m or another MHC component, as detailed further on.

Expression of Transgenes Enhancing the Therapeutic Activity of Immune Cells

According to one aspect of the present method, the exogenous sequence that is integrated into the immune cells genomic locus encodes a molecule that enhances the therapeutic activity of the immune cells.

By "enhancing the therapeutic activity" is meant that the immune cells, or population of cells, engineered according to the present invention, become more aggressive than non-engineered cells or population of cells with respect to a selected type of target cells. Said target cells consists of a defined type of cells, or population of cells, preferably characterized by common surface marker(s). In the present specification, "therapeutic potential" reflects the therapeutic activity, as measured through in-vitro experiments. In general sensitive cancer cell lines, such as Daudi cells, are used to assess whether the immune cells are more or less active towards said cells by performing cell lysis or growth reduction measurements. This can also be assessed by measuring levels of degranulation of immune cells or chemokines and cytokines production. Experiments can also be performed in mice with injection of tumor cells, and by monitoring the resulting tumor expansion. Enhancement of activity is deemed significant when the number of developing cells in these experiments is reduced by the immune cells by more than 10%, preferably more than 20%, more preferably more than 30%, even more preferably by more than 50%.

According to one aspect of the invention, said exogenous sequence encodes a chemokine or a cytokine, such as IL-12. It is particularly advantageous to express IL-12 as this cytokine is extensively referred to in the literature as promoting immune cell activation (Colombo M. P. et al. (2002) "Interleukin-12 in anti-tumor immunity and immunotherapy" *Cytokine Growth Factor Rev.* 13(2):155-68).

According to a preferred aspect of the invention the exogenous coding sequence encodes or promote secreted factors that act on other populations of immune cells, such as T-regulatory cells, to alleviate their inhibitory effect on said immune cells.

According to one aspect of the invention, said exogenous sequence encodes an inhibitor of regulatory T-cell activity is a polypeptide inhibitor of forkhead/winged helix transcription factor 3 (FoxP3), and more preferably is a cell-penetrating peptide inhibitor of FoxP3, such as that referred as P60 (Casares N. et al. (2010) "A peptide inhibitor of FoxP3 impairs regulatory T cell activity and improves vaccine efficacy in mice." *J Immunol* 185(9):5150-9).

By "inhibitor of regulatory T-cells activity" is meant a molecule or precursor of said molecule secreted by the T-cells and which allow T-cells to escape the down regulation activity exercised by the regulatory T-cells thereon. In general, such inhibitor of regulatory T-cell activity has the effect of reducing FoxP3 transcriptional activity in said cells.

According to one aspect of the invention, said exogenous sequence encodes a secreted inhibitor of Tumor Associated Macrophages (TAM), such as a CCR2/CCL2 neutralization agent. Tumor-associated macrophages (TAMs) are critical modulators of the tumor microenvironment. Clinicopathological studies have suggested that TAM accumulation in tumors correlates with a poor clinical outcome. Consistent with that evidence, experimental and animal studies have supported the notion that TAMs can provide a favorable microenvironment to promote tumor development and progression. (Theerawut C. et al. (2014) "Tumor-Associated Macrophages as Major Players in the Tumor Microenvironment" *Cancers* (*Basel*) 6(3): 1670-1690). Chemokine ligand 2 (CCL2), also called monocyte chemoattractant protein 1 (MCP1—NCBI NP_002973.1), is a small cytokine that belongs to the CC chemokine family, secreted by macrophages, that produces chemoattraction on monocytes, lymphocytes and basophils. CCR2 (C—C chemokine receptor type 2—NCBI NP_001116513.2), is the receptor of CCL2.

Although the coding sequence which is inserted at said locus generally encodes polypeptide(s) improving the therapeutic potential of the engineered immune cells, the inserted sequence can also be a nucleic acid able to direct or repress expression of other genes, such as interference RNAs or guide-RNAs. The polypeptides encoded by the inserted sequence may act directly or indirectly, such as signal transducers or transcriptional regulators.

Engineered Immune Cells and Populations of Immune Cells

The present invention is also drawn to the variety of engineered immune cells obtainable according to one of the method described herein, under isolated form, or as part of populations of cells.

According to a preferred aspect of the invention the engineered cells are primary immune cells, such as NK cells or T-cells, which are generally part of populations of cells that may involve different types of cells. In general, population deriving from patients or donors isolated by leukapheresis from PBMC (peripheral blood mononuclear cells).

The present invention encompasses immune cells comprising any combinations of the different exogenous coding sequences and gene inactivation, which have been respectively and independently described above. Among these combinations are particularly preferred those combining the expression of a CAR under the transcriptional control of an endogenous promoter that is active during immune cell activation, in particular one promoter present at one TCR locus, in particular a TCRalpha promoter.

Another preferred combination is the insertion of an exogenous sequence encoding a CAR or one of its constituents under the transcription control of the hypoxia-inducible factor 1 gene promoter (Uniprot: Q16665).

The invention is also drawn to a pharmaceutical composition comprising an engineered primary immune cell or immune cell population as previously described for the treatment of infection or cancer, and to a method for treating a patient in need thereof, wherein said method comprises:

- preparing a population of engineered primary immune cells according to the method of the invention as previously described;
- optionally, purifying or sorting said engineered primary immune cells;
- activating said population of engineered primary immune cells upon or after infusion of said cells into said patient.

Activation and Expansion of T-Cells

Whether prior to or after genetic modification, the immune cells according to the present invention can be activated or expanded, even if they can activate or proliferate independently of antigen binding mechanisms. T-cells, in particular, can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T-cells can be expanded in vitro or in vivo. T cells are generally expanded by contact with an agent that stimulates a CD3 TCR complex and a co-stimulatory molecule on the surface of the T-cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-2, IL-15, TGFβ, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Therapeutic Compositions and Applications

The method of the present invention described above allows producing engineered primary immune cells within a limited time frame of about 15 to 30 days, preferably between 15 and 20 days, and most preferably between 18 and 20 days so that they keep their full immune therapeutic potential, especially with respect to their cytotoxic activity.

These cells form a population of cells, which preferably originate from a single donor or patient. These populations of cells can be expanded under closed culture recipients to comply with highest manufacturing practices requirements and can be frozen prior to infusion into a patient, thereby providing "off the shelf" or "ready to use" therapeutic compositions.

As per the present invention, a significant number of cells originating from the same Leukapheresis can be obtained, which is critical to obtain sufficient doses for treating a patient. Although variations between populations of cells originating from various donors may be observed, the number of immune cells procured by a leukapheresis is generally about from $10^8$ to $10^{10}$ cells of PBMC. PBMC comprises several types of cells: granulocytes, monocytes and lymphocytes, among which from 30 to 60% of T-cells, which generally represents between $10^8$ to $10^9$ of primary T-cells from one donor. The method of the present invention generally ends up with a population of engineered cells that reaches generally more than about $10^8$ T-cells, more generally more than about $10^9$ T-cells, even more generally more than about $10^{10}$ T-cells, and usually more than $10^{11}$ T-cells.

The invention is thus more particularly drawn to a therapeutically effective population of primary immune cells, wherein at least 30%, preferably 50%, more preferably 80% of the cells in said population have been modified according to any one the methods described herein.

According to a preferred aspect of the invention, more than 50% of the immune cells comprised in said population are TCR negative T-cells. According to a more preferred aspect of the invention, more than 50% of the immune cells comprised in said population are CAR positive T-cells.

Engineered immune cells, Populations of cells, therapeutic compositions and uses.

Such compositions or populations of cells can therefore be used as medicaments; especially for treating cancer, particularly for the treatment of lymphoma, but also for solid tumors such as melanomas, neuroblastomas, gliomas or carcinomas such as lung, breast, colon, prostate or ovary tumors in a patient in need thereof.

The invention is more particularly drawn to populations of primary TCR negative T-cells originating from a single donor, wherein at least 20%, preferably 30%, more preferably 50% of the cells in said population have been modified using sequence-specific reagents in at least two, preferably three different loci.

In another aspect, the present invention relies on methods for treating patients in need thereof, said method comprising at least one of the following steps:

(a) Determining specific antigen markers present at the surface of patients tumors biopsies;

(b) providing a population of engineered primary immune cells engineered by one of the methods of the present invention as previously described, preferably expressing a recombinant receptor directed against said specific antigen markers;

(c) Administrating said engineered population of engineered primary immune cells to said patient, Generally, said populations of cells mainly comprises CD4 and CD8 positive immune cells, such as T-cells, which can undergo robust in vivo T cell expansion and can persist for an extended amount of time in-vitro and in-vivo.

The treatments involving the engineered primary immune cells according to the present invention can be ameliorating, curative or prophylactic. It may be either part of an autologous immunotherapy or part of an allogenic immunotherapy treatment.

In another embodiment, said isolated cell according to the invention or cell line derived from said isolated cell can be used for the treatment of solid tumors, in particular solid tumors, such as typically: oesophageal cancer, breast cancer, gastric cancer, cholangiocarcinoma, pancreatic cancer, colon cancer, lung cancer, thymic carcinoma, mesothelioma, ovarian cancer and/or endometrial cancer.

Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The present invention thus can provide more than 10, generally more than 50, more generally more than 100 and usually more than 1000 doses comprising between $10^6$ to $10^8$ gene edited cells originating from a single donor's or patient's sampling.

The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The present invention is also particularly drawn to a general method of treating solid tumor(s) in a patient, comprising the steps of immunodepleting said patient with a lymphodepletion regimen and infusing genetically engineered lymphocytes made resistant to the lymphodepletion agent used in the lymphodepletion regimen and specifically targeting said solid tumor(s). Such genetically engineered lymphocytes are preferably CAR positive T-cells, more preferably endowed with a MSLN-CAR as described herein.

The lymphodepletion regimen preferably comprises an antibody directed against an antigen present at the surface of immune cells, such as CD52, CD3, CD4, CD8, CD45, or other specific markers, or being drugs such as purine analogues (ex: fludarabine and/or chlorofarabine) and glucocorticoids.

According to a preferred embodiment of the invention, the method comprises submitting the patient to a lymphodepletion regimen comprising an antibody directed against CD52, and administrating an engineered CAR T-cell endowed with a MSLN-CAR, which expression of CD52 is reduced, deficient or inactivated.

As a preferred embodiment of the present invention, the lymphodepleting treatment can comprise an anti-CD52 antibody, such as alemtuzumab, alone or in combination. The lymphodepletion regimen may for instance combine cyclophosphamide, typically for 1 to 3 days, fludarabine for 1 to 5 days, and alemtuzumab from 1 to 5 days. In general, the lymphodepletion regimen can comprise cyclophosphamide between 50 and 70 mg/kg/day, fludarabine between 20 and 40 mg/m2/day, and alemtuzumab 0.1 to 0.5 mg/kg/day alone or in combination.

To this aim, the present invention provides with the combined use of a composition for lymphodepleting a patient affected by a solid tumor, said composition comprising an anti-CD52 antibody, and a population of engineered lymphocytes targeting MSLN that are not sensitive to said antibody, such population preferably comprising cells that express MSLN-CAR and have impaired CD52 expression. In such engineered cells, allele(s) of the CD52 gene has been preferably inactivated by a rare-cutting endonuclease, such as a TALE-nuclease or a RNA-guided endonuclease as previously described.

The present invention also provides with a medical kit comprising said lymphodepleting composition and said population of engineered cells resistant thereto for its use in solid tumors cancer treatment.

By "cytolytic activity" or "cytotoxic activity" or "cytotoxicity" is meant the percentage of cell lysis of target cells conferred by an immune cell.

A method for determining the cytotoxicity is described below:

With adherent target cells: $2.10^4$ specific target antigen (STA)-positive or STA-negative cells are seeded in 0.1 ml per well in a 96 well plate. The day after the plating, the STA-positive and the STA-negative cells are labeled with CellTrace CFSE and co-cultured with $4\times10^5$ T cells for 4 hours. The cells are then harvested, stained with a fixable viability dye (eBioscience) and analyzed using the MACSQuant flow cytometer (Miltenyi).

With suspension target cells: STA-positive and STA-negative cells are respectively labeled with CellTrace CFSE and CellTrace Violet. About $2\times10^4$ ROR1-positive cells are co-cultured with $2\times10^4$ STA-negative cells with $4\times10^5$ T cells in 0.1 ml per well in a 96-well plate. After a 4 hour incubation, the cells are harvested and stained with a fixable viability dye (eBioscience) and analyzed using the MACSQuant flow cytometer (Miltenyi).

The percentage of specific lysis can be calculated using the following formula:

$$\%\text{ cell lysis} = 100\% - \frac{\dfrac{\%\text{ viable target cells upon coculture with } CAR \text{ modified } T \text{ cells}}{\%\text{ viable control cells upon coculture with } CAR \text{ modified } T \text{ cells}}}{\dfrac{\%\text{ viable target cells upon coculture with non modified } T \text{ cells}}{\%\text{ viable control cells upon coculture with non modified } T \text{ cells}}}$$

By "increased cytotoxicity" is meant that the % cell lysis of target cells conferred by the engineered immune cells is increased by at least 10%, such as at least 20%, at least 30%, at least 40%, at least 50%, at least 60%, at least 70%, at least 80%, at least 90% or at least 100% or more, compared to the % cell lysis of target cells conferred by the immune cell not being engineered.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein generally refers to mammalians, preferably to primates and more preferably to humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

EXAMPLES

Mesothelin (MSLN) is a glycophosphatidylinsositol (GPI)-linked cell surface protein normally expressed in mesothelioma cells that line the pleura, peritoneum, and pericardium. The MSLN gene encodes a precursor protein of 71 kDa that is processed to a 31 kDa shed protein called MPF (megakaryocyte potentiating factor) and a 40 kDa membrane bound protein, mesothelin.

Mesothelin is reported to be highly expressed in several types of malignant tumors, such as malignant mesothelioma, ovarian cancer, pancreatic adenocarcinoma, and lung adenocarcinoma (Morello et al., 2016; O'Hara et al., 2016). In some cases, mesothelin expression has been associated with increased tumor aggressiveness and poor clinical outcome.

Description of the MSLN-Specific CARs Used in the Study

Three second-generation CARs composed of the respective scFvs P4, meso1 and MESO2, comprising CD8α hinge/transmembrane domain, and the 4-1BB and CD3ζ activation domains, were generated and screened for chimeric antigen receptor (CAR) expression and anti-tumor activity in vitro, through the activity of primary mesoCAR$^{+}$ T-cells against target cell lines expressing different levels of Mesothelin (MSLN). In certain versions, a suicide switch "R2" was introduced in the CAR architecture. The "R2" polypeptide, which includes two CD20 mimotopes, was located between the scFv and the hinge to confer sensitivity to anti-CD20 therapeutic antibodies, such as rituximab, as previously described in WO2016120216.

A schematic representation of the CAR structure is presented in FIG. 1.

The different sequences comprised into each CARs are detailed in tables 1, 2 and 3 and the full amino acid sequence thereof are shown in table 4.

1—In-Vitro Assays

CARs were screened for expression in primary T-cells from PBMC and assayed for their anti-tumor activity against 3 target cell lines expressing different levels of MSLN, respectively:

- HeLa (ATCC® CCL-2), an epithelial cervix adenocarcinoma,
- HPAC (ATCC® CRL-2119), an epithelial pancreatic adenocarcinoma, and
- 293H or A2058 cells mesothelin negative cells.

Expression of mesothelin at the surface of these cells was assessed by flow cytometry as shown in FIGS. 3 and 4.

2—Production of Gene Edited MSLN-UCART Cells

- At day 0, frozen human Peripheral Blood Mononuclear Cells (PBMC) from Hemacare (Northridge, CA 91325, USA) were thawed, washed, counted and resuspended in X-vivo 15 medium supplemented with 5% AB serum. The cells were then transferred to an incubator set at 37° C., 5% CO2.
- At day 1, PBMC were counted, analyzed by flow cytometry to assess the % of CD3+ cells, centrifuged and resuspended in X-vivo 15 medium supplemented with 5% AB serum, 350 UI/ml IL2 and MACS GMP T Cell TransAct (60 μl per million of CD3+ cells). The cells were then transferred to an incubator set at 37° C., 5% CO2.
- At day 4, T cells and rLV vectors bearing the polynucleotide sequences encoding the anti MSLN CARs were resuspended in X-vivo 15 medium supplemented with 5% AB serum and 350 UI/ml IL2, and seeded over retronectin coated plates. The plates were then transferred to an incubator set at 37° C., 5% CO2.
- At day 5, T cells were washed and resuspended in X-vivo 15 medium-supplemented with 5% AB serum, 350 UI/ml IL2. The cells were then transferred to an incubator set at 37° C., 5% CO2.
- At day 6, T cells were co-electroporated with mRNA encoding the right and the left arms of respectively the TRAC TALEN and CD52 TALEN. as previously reported [Poirot et al. (2013) Blood. 122 (21): 1661] to efficiently inactivate TCRα and CD52 gene and prevent TCRαβ expression at the surface of the primary T-cells. TALEN is the registered name for the TALE-nucleases designed by Cellectis (8, rue de la Croix Jarry, 75013 Paris, France). The genomic target sequences for these TALE nucleases are indicated in Table 8 below. Transfection was performed using the AgilePulse technology. The cells were then transferred to an incubator set at 37° C., 5% CO2.
- At day 7, T cells were washed and resuspended in X-vivo 15 medium-supplemented with 5% AB serum, 350 UI/ml IL2. The cells were then transferred to an incubator set at 37° C., 5% CO2.
- Between days 7/8 and 18, T cells were expanded in GRex devices. When GRex 6 multi-well cell culture plates were used, half the culture media was removed at days 11 and 15 and replaced with fresh medium containing IL2, and fresh IL2 was added at day 13. When GRex 100M were used, fresh IL2 was added at days 11, 13 and 15 without any medium change. During the expansion period, the cell cultures were incubated at 37° C. under 5% CO2.
- At day 18, the totality of the UCART cells was cryopreserved for later used in in vitro and in vivo assays.

TABLE 8

Genomic sequences targeted by the TALE-nucleases (TALEN)

| Gene coding sequence (human) | SEQ ID NO: # | Target sequence (5' > 3') |
|---|---|---|
| TRAC | 159 | TTGTCCCACAGATATCCAgaaccctgaccctgCCGTGTACCAGCTGAGA (spacer) |
| CD52 | 160 | TTCCTCCTACTCACCATcagcctcctggttatGGTACAGGTAAGAGCAA (spacer) |

2.1 MSLN-CAR Expression Analysis

P4-R2, Meso1-R2 and MESO2-R2 CARs were used to generate three MSLN-specific UCART cell products. The different UCART cell products were then evaluated in vitro.

The first in vitro study performed on the four UCART cell products aimed at determining the phenotype of UCART cells at day 18. For this purpose, CAR and TCRαβ expression at the surface of UCART cells, as well as CD4 and CD8 expression at the surface of the CAR+ fraction of UCART cells were analyzed by flow cytometry. CAR surface expression was evaluated using either His-tagged recombinant human mesothelin protein, or biotinylated protein L, that all recognize the scFv portion of the CARs or biotinylated rituximab that recognizes the R2 suicide switch portion of the CARs. TCRαβ receptor surface expression was evaluated using PE-vio770 conjugated anti-TCRαβ antibody. CD4 and CD8 surface expression were evaluated using FITC-conjugated CD4 and BV510-conjugated CD8 antibodies.

CAR surface expression was evaluated by flow cytometry using either His-tagged recombinant human mesothelin protein that recognizes the scFv portion of the CARs, or biotinylated rituximab that recognizes the R2 suicide switch portion of the CARs.

As shown in FIG. 6, at least 50% of the UCART cells modified with either P4-R2, Meso1-R2 or MESO2-R2 were CAR positive. However P4-R2 CAR displayed higher expression level than Meso1-R2, and MESO2-R2 CARs.

As shown in FIG. 7, at least 51% of the CAR+ fraction of UCART cells modified with P4-R2, Meso1-R2 and MESO2-R2 CAR were CD4+.

2.2 IFNg Production and Killing Activity

The second in vitro study performed on the three UCART cell products aimed at analysing UCART cells function. The capacity of UCART cells to produce cytokines upon a 24 hours coculture with HPAC (MSLN+) or 293H (MSLN−) cells was evaluated by quantifying the IFNg in cell culture supernatants by ELISA according to standard procedures.

As shown in FIG. 8, UCART cells modified with P4-R2 and Meso1-R2 CARs produced repectively more than 40000 μg/ml and 50000 μg/ml of IFNg upon coculture with a MSLN+ cell line and less than 1500 and 200 μg/ml of IFNg respectively upon coculture with a MSLN− cell line. Despite the fact that UCART cells modified with Meso1-R2 CAR produced similar level of IFNg than UCART cells modified with P4-R2 CARs upon coculture with a MSLN+ cell line, the Meso1-R2 CAR endowed cells produced extremely low level of IFNg upon culture with a MSLN− cell line. UCART cells modified with MESO2-R2 CAR produced no more than 15000 μg/ml of IFNg upon coculture with a MSLN+ cell line.

The capacity of UCART cells to perform serial killing of HPAC cells was then evaluated over a period of 15 days including 6 rounds of exposure to MSLN+(HPAC) cells at ratios 1:2 and 1:8.

As shown in FIG. 9, CART cells modified with P4-R2, Meso1-R2 and MESO2-R2 CARs displayed similar level of killing activity after a single round of exposure to HPAC cells. However, upon several rounds of exposure, T-cells endowed with Meso1-R2 and P4-R2 displayed much higher serial killing activity than the CART cells endowed with MESO2-R2 CARs, while CART cells modified with Meso1-R2 showed more sustained activity than those modified with P4-R2

Importantly, none of these CART cell products displayed significant killing activity against mesothelin negative A2058 and 293H cells.

3. Functional Validation of the UCART MSLN Cells Genetic Attributes 3.1 Knock-Out of the TRAC and/or CD52 Genes As shown in FIG. 10, less than 20% of the UCART cells modified with P4-R2, Meso1-R2 and MESO2-R2 CAR remained TCRαβ+, suggesting that the level of TALEN-mediated inactivation of the TCRα gene was highly efficient in the population of cells.

Further, according to the flow cytometry data presented in FIG. 11, the depletion of TCRαβ+ was an efficient step to remove non engineered cells and select $[CAR]^+[TCR]^-$ UCART cells: 84% of non-engineered T-cells were TCRαβ+ as compared to 8% for the T-cells knocked-out for the TRAC gene and 0.2% for the T-cells knocked-out for the TRAC gene and depleted in TCRαβ+ cells.

To fully demonstrate that the absence of detection of the TCRαβ receptor at the surface of cells knocked-out for the TRAC gene and depleted in TCRαβ+ cells was associated with an absence of expression of functional TCRαβ receptor, non-engineered T-cells, T-cells knocked-out for the TRAC gene, and T-cells knocked-out for the TRAC gene and depleted in TCRαβ+ cells, were exposed for 24 hours to phytohaemagglutinin (PHA) and analyzed by flow cytometry to monitor the expression of the activation marker CD25.

As shown in FIG. 12, only the non-engineered T-cells expressed significant level of CD25 at their surface upon exposure to PHA. These data clearly demonstrate that the knock out of the TRAC gene in T-cells prevents the expression of a functional TCRαβ receptor at the cell surface.

Inactivation of CD52 genes was assessed by incubating the engineered Cells after 7 days of culture in 50 μg/ml anti-CD52 monoclonal antibody (or rat IgG as control) with or without 30% rabbit complement (Cedarlane). After 2 hours of incubation at 37° C., the cells were labeled with a fluorochrome-conjugated anti-CD52 antibody together with a fluorescent viability dye (eBioscience) and analyzed by flow cytometry to measure the frequency of CD52-positive and CD52-negative cells among live cells. On another hand the cells were cultured with the antibody to select resistant 3.2 UCART Cell Depletion by Using Rituximab Against R2 Polypeptide Another in vitro study performed on the UCART cell products aimed at evaluating the ability of the CAR+ fraction of UCART cells to be depleted upon treatment with rituximab.

UCART cells modified with P4-R2, Meso1-R2 and MESO2-R2 CARs were co-cultured for two days with HPAC cells, exposed for two hours to medium, rituximab (RTX), baby rabbit complement (BRC) or a mixture of rituximab and baby rabbit complement, and analyzed by flow cytometry to monitor the percentage of CAR+ cells. As shown in FIG. 13, UCART cells modified with P4-R2, Meso1-R2 and MESO2-R2 were efficiently depleted upon rituximab and baby rabbit complement treatment. By contrast, UCART cells modified with P4-naked (MSLN CAR with the P4 structure without R2 sequences) were not depleted.

3.3 Inactivation of TGFβ Signaling Pathway in CAR T Cells

Another attribute provided to MesoCAR T cell, was to resist to tumor microenvironment by inactivating TGFb signaling pathway. Two different strategies were investigated, either inactivating the expression of TGFbRII gene by knock out or by overexpressing a dominant negative form of the TGFbRII gene (dnTGFbRII).

3.3.1. Inactivation of TGFbRII by KO

Activated T cells were electroporated with 10 μg of mRNA encoding the right and the left arms of two TALENs targeting TGFbRII gene (SEQ ID NO:155 (pCLS32939) and SEQ ID NO:156 (pCLS32940) or SEQ ID NO:157 (pCLS32967) and SEQ ID NO:158 (pCLS32968)). Three days post transfection, T cells were harvested, gDNA was extracted and PCR was performed in order to amplify the amplicons. PCR products were analyzed by deepsequencing and results show that transfection with TALEN encoded by pCLS32939 and pCLS32940 or with TALEN encoded by pCLS32967 and pCLS32968 showed 96.62% and 97.28% of gene editions (i.e. insertions and/or deletions) respectively, demonstrating the high efficiency of TGFbRII KO.

3.3.2. Inactivation of TGFbRII by Overexpression of dnTGFbRII

MSLN-CAR T cells were produced as described in Example 2 using two different Donors and with rLV vectors encoding the different MSLN CARs and with or without a dnTGFbRII (SEQ ID NO:24) separated by a 2A cleavage peptide. After the production process, the different MSLN-CAR T cells were thawed and seeded at 3 millions cells/ml with 70 UI/ml of IL-2. One day post thawing cells were exposed to 5 ng/ml of TGFb (R&D systems). One hour later, cells were stained for CAR expression by performing a cell surface staining of the cells with biotinylated recombinant mesothelin protein (LakePharma) and brilliant Violet 421 streptavidin (BD). In addition, an intracellular staining of the MSLN-CAR T cells was performed with PE-conjugated anti-phospho SMAD2/3 (BD) according to the provider's instructions. Cells were analyzed by flow cytometry and phosphorylated SMAD2/3 status was determined in either CAR positive or CAR negative subpopulation (FIG. 14). The results demonstrate that in absence of dnTGFbRII, the cells were positive for phosphorylation of SMAD2/3 (FIG. 14, left panels) while in presence of dnTGFbRII only CAR positive cells could show a reduction of SMAD2/3 phosphorylation (FIG. 14, right panels). These results showed that TGFb signaling could be impaired in MSLN-CART cells expressing a dnTGFbRII.

4—In-Vivo Experiments

Preliminary in vivo studies were performed to define and validate the animal/tumor model and route of administration of the CAR T-cells. HPAC tumor cells injected subcutaneously (SC) in NSG mice was selected as the animal/tumor model to be used to evaluate the anti-tumor activity in vivo of T-cells expressing the 3 selected mesoCAR constructs. Although meso1-R2 was below in terms of level of expression at the cell surface, cytotoxicity and IFNγ secretion, this was kept in the study and compared to P4-R2 and MESO2-R2 CARs Human T-cells expressing the mesoCAR candidates and the P4-CAR were then evaluated for their anti-tumor activity in vivo. Briefly, NSG mice were engrafted with a MSLN$^+$ cell line (HPAC cells, SC injection) and then treated with mesoCAR$^+$ T-cells (IV injection, 3 doses). mesoCAR$^+$ T-cells activity was assessed by the monitoring of tumor growth. The 3 mesoCAR$^+$ T-cells evaluated showed anti-tumor activity in vivo against HPAC tumor cells with different level of activity. T-cells expressing the MESO2-R2 CAR showed less activity compared to the other mesoCAR$^+$ T-cells evaluated.

4.1 Rationale for the Choice of the Animal Model

Because of the human specificity of the mesoCAR$^+$ T-cells, studies in standard immunocompetent animal models are not applicable due to the rapid targeting and elimination of human T-cells by xenogeneic immune reactions. The animal model selected is the highly immunodeficient NSG mice strain (NOD.Cg-Prkdc$^{scid}$ Il2rg$^{tmw1\,Wjl}$/SzJ strain from the Jackson laboratory) as it allows the engraftment of both human MSLN$^+$ tumor cells and human CAR T-cells.

4.2 Establishment of the Animal/Tumor Model 4.2.1 Hela and HPAC Engraftment

Two mesothelin-expressing tumor cell lines: HeLa (ATCC® CCL-2), an epithelial cervix adenocarcinoma, and HPAC (ATCC® CRL-2119), an epithelial pancreatic adenocarcinoma, were used in this study. The aim of this first study was to evaluate the tumor take and tumor growth parameters of HeLa and HPAC cells after subcutaneous (SC) injection of NSG mice (6-8 weeks old).

Briefly, on Day 0, mice were randomized according to their individual body weight into 4 groups of 6 mice each and received a SC injection of HeLa ($1\times10^6$ or $10\times10^6$ cells/mouse) or HPAC cells ($2\times10^6$ or $10\times10^6$ cells/mouse). Quantity of tumor cells were chosen according to the literature [Abate-Daga, D., et al. (2014). A Novel Chimeric Antigen Receptor Against Prostate Stem Cell Antigen Mediates Tumor Destruction in a Humanized Mouse Model of Pancreatic. *Cancer. Hum. Gene Ther*, Arjomandnejad et al. (2014) Hela cell line xenograft tumor as a suitable cervical cancer model: Growth kinetic characterization and immunohistochemistry array. *Arch. Iran. Med.*; Kusakawa et al. (2015) Characterization of in vivo tumorigenicity tests using severe immunodeficient NOD/Shi-scid IL2Rγnull mice for detection of tumorigenic cellular impurities in human cell-processed therapeutic products. *Regen. Ther.*).

Body weight, viability and behavior were monitored every day. The tumor volume was measured three times a week. Surviving mice were terminated at Day 61 (end of study). Necropsy (macroscopic examination) was performed on all terminated animal in the study, and, if possible, on all euthanized moribund or found dead animal.

Both HPAC and Hela tumors have grown in NSG mice. HPAC tumor grew faster than Hela tumor. Mean tumor volume V (500 mm$^3$) for mice injected with $1\times10^6$ and $10\times10^6$ HeLa cells was respectively 519 mm$^3$ and 498 mm$^3$ with a mean time to reach of 55 days and 49 days. Mean tumor volume V (500 mm$^3$) for mice injected with $2\times10^6$ and $10\times10^6$ HPAC cells was respectively 557 mm$^3$ and 500 mm$^3$ with a mean time to reach of 24 days and 23 days.

4.2.2 Mesothelin Expression on Hela and HPAC Tumors in NSG Mice

The aim of the second study was to evaluate the level of expression of the mesothelin in both HPAC and Hela tumors after subcutaneous injection and growth of tumor cells in NSG mice.

Briefly, on Day 0, mice were randomized according to their individual body weight into 2 groups of 3 mice each and received a SC injection of HeLa ($10\times10^6$ cells/mouse) or HPAC cells ($2\times10^6$ cells/mouse). Body weight, viability and behavior were monitored every day. The tumor volume was measured three times a week. Tumors were collected when tumor volume reached 300-500 mm$^3$. Tumor samples were analyzed by immunohistochemical (IHC) analysis of mesothelin expression. Last mouse was sacrificed at Day 63 (end of study).

Both HPAC and Hela tumors have grown in NSG mice. As observed in the previous study, HPAC tumors have grown faster than Hela tumors. The mean tumor volume of 300 mm$^3$ for mice injected with HeLa cells or HPAC cells was respectively reached at 40 days and 28 days.

In addition, the expression of mesothelin on the tumor cells was checked using IHC on tumors collected on the mice. Both tumors expressed mesothelin.

Based on these confirmatory data, it was decided to use HPAC cells (2×10$^6$ cells, SC injected) to evaluate the anti-tumor activity of mesoCAR$^+$ T-cells.

4.2.3 HPAC-luc-GFP Tumor Cells Engraftment

HPAC cells expressing firefly luciferase and GFP (HPAC-luc-GFP) were generated by Cellectis and the tumor take and tumor growth of HPAC-luc-GFP cells in NSG mice was evaluated as previously described.

Briefly, on Day 0, 3 mice received a SC injection of HPAC-luc-GFP cells (2×10$^6$ cells/mouse). Body weight, viability and behavior were monitored every day. The tumor volume was measured three times a week and bioluminescence imaging was performed on Day 7, 14 and 24. Viability and behavior were monitored every day.

Since these conditions offered sensitivity for this assay, it was decided to use wild type HPAC cells (SC injection, 2×10$^6$ cells/mouse) to evaluate mesoCAR$^+$ T-cells activity in vivo.

4.3 Evaluation of Anti-Tumor Activity of UCARTmeso Candidates Against HPAC Tumors in NSG Mice The aim of this study was to compare the anti-tumor activity of the 3 UCARTmeso candidates (P4-R2, MESO2-R2 and meso1-R2) in NSG mice bearing subcutaneous HPAC tumors using the treatment conditions defined using the pilot study. 3 doses of CAR$^+$ T-cells were evaluated (1, 3 and 10×10$^6$ CAR positive cells/mouse).

UCARTmeso and control T-cells were produced with PBMCs from the same donor. UCARTmeso and controls T-cells were not purified for TCRαβ-negative cells. Characteristics of the T-cells used are in Table 9.

TABLE 9

Characteristics of the T-cells used in the study.

| | Product | | | |
|---|---|---|---|---|
| | UCARTmeso | | | Control T-cells (KO |
| CAR | P4-R2 | Meso1-R2 | MESO2-R2 | TRAC/NT) none |
| % CAR$^+$ | 67.24 | 49.6 | 25.8 | NA |
| % CD4$^+$ among CAR+ | 59.11 | 54.5 | 51.4 | 90.34 |
| % CD8$^+$ among CAR+ | 36.72 | 34.7 | 29.6 | 8.19 |
| % TCRαβ$^-$ | 84.91 | 89.62 | 87.84 | 90.22 |

Day 18: end of production process (before freezing);
% CAR$^+$: % CD45$^+$/CAR$^+$ over CD45$^+$ at Day 18 (measured by flow cytometry using the recombinant MSLN protein for P4-R2 CARs and using L-protein for Meso1-R2 and MESO2-R2 CARs)
% CD4$^+$: % CD45$^+$/CAR$^+$/CD4$^+$ over CD45$^+$ at Day 18
% CD8$^+$: % CD45$^+$/CAR$^+$/CD8$^+$ over CD45$^+$ at Day 18
% TCRαβ$^-$: % CD45$^+$/TCRαβ$^-$ over CD45$^+$ at Day 18

Briefly, 85 NSG mice received a subcutaneous injection of HPAC tumor cells (2×10$^6$ cells/mouse) at Day −7. At Day 0, 80 tumor bearing mice were randomized according to the tumor volume into 16 groups of 5 mice.

Human T-cells (UCARTmeso cells and KO TRAC/NT cells in control) were injected on Day 0 (for groups 1 to 15) or on Day 12 (for group 16). For UCARTmeso cells, the total number of cells injected was defined according to the percentage of CAR positive cells in the batch in order to inject the indicated number of CAR positive cells per mouse (1, 3 or 10×10$^6$ CAR positive cells).

The anti-tumor activity of UCARTmeso candidates CARs (P4-R2, Meso1-R2 and MESO2-R2) was evaluated by measuring the tumor volume (FIGS. 15, 16 and 17). All UCARTmeso cells showed an anti-tumor activity, although with different level of activity between the different CAR T-cells.

As shown in FIG. 18, at the higher dose (10×10$^6$), an anti-tumor activity was observed for all CAR candidates. 3×10$^6$ MESO2-R2 CAR$^+$ cells were unable to control the HPAC tumor growth.

Conclusions

An animal/tumor model and treatment conditions allowing the evaluation of anti-tumor activity of CAR T-cells targeting mesothelin has been set-up. Activity of the 3 CAR candidates MESO2-R2, Meso1-R2 and P4-R2) was evaluated in vivo using this animal model and all CAR T-cells showed anti-tumor activity against HPAC cells.

However, activity was lower for MESO2-R2 CAR+ T-cells compared to CAR+ T-cells expressing Meso1-R2.

Among the CAR T-cells bearing the selected attributes (R2 suicide switch and TRAC KO), Meso1-R2 CAR T-cells candidate is displaying the highest in-vivo activity at the 3 evaluated doses.

4.4—Evaluation of Anti-Tumor Activity of UCARTmeso Candidates Expressing dnTGFBRII The aim of this study was to compare, in NSG mice, the anti-tumor activity of 2 UCARTmeso candidates (P4-R2, MESO1-R2) that are also expressing dnTGFBRII. Briefly, on Day 0, 4 to 6 mice per group received a SC injection of HPAC cells (2×10$^6$ cells/mouse). Body weight, viability and behavior were monitored every day. The tumor volume was measured three times a week. Viability and behavior were monitored every day.

All UCARTmeso expressing dnTGFBRII were produced with PBMCs from the same donor and 2 doses of CAR$^+$ T-cells were evaluated (3 and 10×10$^6$ CAR positive cells/mouse).

The anti-tumor activity of UCARTmeso candidates expressing dnTGFBRII (P4-R2, MESO1-R2) was evaluated by measuring the tumor volume (FIG. 19). Both UCARTmeso cells showed an anti-tumor activity, although with different level of activity with MESO1 construct showing a better antitumoral activity.

5—Comparison of TGFBRII Gene Inactivation (KO TGFBRII) and the dnTGFBRII Gene Overexpression Approaches for UCART Targeting Mesothelin (UCART MESO)

The work presented in this study aimed at comparing the TGFBRII KO and the dnTGFBRII gene overexpression approaches and to select the best approach for UCART MESO.

To conduct this study, six types of genetically modified T cells (as define in Table 10) were generated and tested.

TABLE 10

Description of the six types of genetically modified T cells generated for the study.

| | $[TCR]^-$ $[P4\ CAR]^+$ | | | $[TCR]^-$ $[MESO1\ CAR]^+$ | | |
|---|---|---|---|---|---|---|
| | 1 | 2 | 3 | 4 | 5 | 6 |
| Overexpression | P4 CAR | P4 CAR dnTGFBRII | P4 CAR | MESO1 CAR | MESO1 CAR dnTGFBRII | MESO1 CAR |
| Gene inactivation (TALEN) | KO TRAC | KO TRAC | KO TRAC KO TGFBRII | KO TRAC | KO TRAC | KO TRAC KO TGFBRII |

5.1 Production of the Different UCART MESO

At day 0, frozen human Peripheral Blood Mononuclear Cells (PBMC) from Hemacare (Northridge, CA 91325, USA) were thawed, washed, counted and resuspended in X-vivo 15 medium supplemented with 5% AB serum. The cells were then transferred to an incubator set at 37° C., 5% CO2.

At day 1, PBMC were counted, analyzed by flow cytometry to assess the % of CD3+ cells, centrifuged and resuspended in X-vivo 15 medium supplemented with 5% AB serum, 350 UI/ml IL2 and MACS GMP T Cell TransAct (60 µl per million of CD3+ cells). The cells were then transferred to an incubator set at 37° C., 5% CO2.

At day 4, T cells and rLV vectors bearing the polynucleotide sequences encoding the different anti mesothelin CARs P4-CAR (SEQ ID NO:161) and MESO1 CAR (SEQ ID NO:22) with or without the dnTGFBRII gene (SEQ ID NO: 24) were resuspended in X-vivo 15 medium supplemented with 5% AB serum and 350 UI/ml IL2, and seeded over retronectin coated plates. The plates were then transferred to an incubator set at 37° C., 5% CO2.

At day 5, T cells were washed and resuspended in X-vivo 15 medium-supplemented with 5% AB serum, 350 UI/ml IL2. The cells were then transferred to an incubator set at 37° C., 5% CO2.

At day 6, T cells were electroporated with mRNA encoding the right and the left arms of the TRAC TALEN and with or without mRNA encoding the right and left arms of TGFBRII TALEN (SEQ ID NO:157 and SEQ ID NO:158). Transfection was performed using the AgilePulse technology. The cells were then transferred to an incubator set at 37° C., 5% CO2.

At day 7, T cells were washed and resuspended in X-vivo 15 medium-supplemented with 5% AB serum, 350 UI/ml IL2. The cells were then transferred to an incubator set at 37° C., 5% CO2.

Between days 7/8 and 18, T cells were expanded in GRex devices. During the expansion period, the cell cultures were incubated at 37° C. under 5% CO2 and culture medium was changed from time to time.

At day 18, the totality of the UCART cells was cryopreserved for later used in in vitro and in vivo assays.

5.2 Evaluation of the UCART Cell Population

At day 18, the UCART were analyzed by flow cytometry. CAR surface expression was evaluated using biotinylated recombinant mesothelin protein, that recognize the scFv portion of the CARs and PE-conjugated streptavidin. The dnTGFBRII was evaluated using an anti-TGFBRII (from Abcam) and an APC-conjugated anti mouse IgG antibody. CD4 and CD8 surface expression were evaluated using FITC-conjugated CD4 and BV510-conjugated CD8 antibodies. In addition, the stemness of the UCART cells in CAR+CD4+ or CAR+ CD8+ positive cells where analyzed using anti-CD62L conjugated to PECy7 and anti-CD45RA coupled to APC.

As shown in FIG. 20A, 58% of the UCART cells were detected for the expression of the P4 and 37% of the UCART cells were detected for the expression of the MESO1. In addition, the dnTGFBR2 was detected in 32% and 17% of the UCART cells when transduced with the P4-dnTGFBRII and the MESO1-dnTGFBRII constructs. These results could reflect a lower expression of dnTGFBRII placed downstream a 2A peptide and the CAR.

Interestingly, among CAR positive cells, the percentage of CD8+ positive cells was varying between 27 and 35% when the UCART cells expressed the P4 CAR construct. Whereas when expressing the MESO1 construct, the percentage CD8+ cells (among CAR positive cells) was varying from 36 to 51% (FIG. 20B).

In addition, the analysis of stemness revealed that in CAR+CD4+ cells (FIG. 21A), naïve (Tn) and Memory Stem T cells (Tscm) vary from 1 to 3% with the P4CAR, whereas in MESO1 CAR expressing T cells, this subset was higher and varying around 6%. This effect was also observed in CAR+CD8+ cells, to a less extent, since this T cell subset was varying from 15 to 19% or from 19 to 22% with the P4 or MESO1 constructs, respectively (FIG. 21B).

These results demonstrate that even if less expressed or detected, the MESO1 CAR led to a higher proportion of CD8+ (i.e. cytotoxic) and a higher proportion of Tn and Tscm subset than the P4CAR. Importantly the inactivation of TGFBRII either by overexpression of the dnTGFBRII construct or by KO had no impact on any of the phenotypes analysed.

5.3 Evaluation of Cytotoxicity and IFNγ Production of UCARTs

After a 16 hours post thaw recovery period, T cells genetically modified as indicated in Table 9 were mixed with H226-Luc/GFP cells at 1:3, 1:1, 3:1, 10:1 effector-to-target (E:T) ratios. Cocultures were then incubated overnight at 37° C. and bioluminescence was measured to quantify the lysis of H226 cells. Alternatively, after the post thawing recovery period, these genetically modified T cells were resuspended in culture medium and seeded at a density of 200000 cells/well in 96 well untreated or previously coated with 75 ng/well of His-tagged recombinant mesothelin protein plates. Following a 24 hours incubation period, cell supernatants were collected and analyzed by ELISA to quantify the production of IFNg.

As shown in FIG. 22, the UCART expressing MESO1 could induce higher cytotoxicity at the lowest doses (1:3 and 1:1 ratio) than the UCART expressing P4.

FIG. 23A demonstrates that the recombinant mesothelin protein was able to induce IFNg secretion in all the UCAR T produced. This production was varying from 40,000 up to 90,000 µg/ml and no obvious impact of the CAR construct or the TGFB pathway inhibition could be observed. However, when analyzing the IFNg secretion in absence of recombinant mesothelin (FIG. 23B), surprisingly the MESO1 CAR construct was producing less IFNg than the P4 construct. This result suggests that UCART cells expressing MESO1 CAR constructs are less stimulated in absence of antigen, which means that MESO1 CAR has reduced "auto-activation". This is an important property in therapeutic settings because "auto activation" tends to exhaust CAR T-cells.

5.4 Evaluation of TGFb Sensitivity

In order to determine the impact of TGFB pathway inactivation either by KO or by overexpression of a dnTGFBRII, the genetically modified T cells as described in Table 9 were exposed to TGFb for one hour and were analyzed by flow cytometry to evaluate the fraction of pSMAD2/3 positive vs pSMAD2/3 negative cells among CAR positive cells. In another set of experiment, the produced UCART cells were exposed to recombinant mesothelin protein in presence or not of TGFb and were counted 7 days later to assess proliferation.

FIG. 24A shows that without inhibition of TGFb pathway, more than 95% of the CAR positive fraction of UCART cells were pSMAD2/3 positive. When inhibiting by overexpression with dnTGFBRII, 67 and 60% of the CAR positive fraction of UCART expressing P4 or MESO1 construct were pSMAD2/3 negative. Interestingly, inactivation by KO led to 85 ad 83% of pSMAD2/3 negative cells when expressing P4 or MESO1 construct, respectively. This result demonstrates that TGFBRII KO has a stronger ability to reduce SMAD2/3 phosphorylation.

FIG. 24B shows that TGFb is able to inhibit the antigen-mediated proliferation of UCART expressing P4 or MESO1 construct to the same extent. Importantly TGFB pathway inhibition by either KO or dnTGFBRII overexpression are able to decrease or even abolish such inhibition.

The invention claimed is:

1. A mesothelin specific chimeric antigen receptor (CAR) comprising at least:

an extracellular ligand binding-domain comprising VH and VL from a monoclonal anti-mesothelin antibody;

a transmembrane domain; and a cytoplasmic domain comprising a CD3 zeta signalling domain and a co-stimulatory domain, wherein said extracellular ligand binding-domain is directed against the MSLN antigen polypeptide region SEQ ID NO:25, wherein said extracellular ligand binding-domain comprises:

a variable heavy VH chain comprising CDRs from the antibody Meso1 having the amino acid sequence of SEQ ID NO:3 (CDRH1-Meso1), SEQ ID NO:4 (CDRH2-Meso1) and SEQ ID NO:5 (CDRH3-Meso1), and a variable heavy VL chain comprising CDRs from the antibody Meso1 having the amino acid sequence of SEQ ID NO:6 (CDRL1-Meso1), SEQ ID NO:7 (CDRL2-Meso1) and SEQ ID NO:8 (CDRL3-Meso1).

2. The mesothelin specific chimeric antigen receptor according to claim 1, wherein said extracellular ligand binding-domain comprises VH and VL chains having at least 90% sequence identity respectively with SEQ ID NO:9 (Meso1-VH) and SEQ ID NO:10 (Meso1-VL).

3. The mesothelin specific chimeric antigen receptor (CAR) according to claim 1, wherein the transmembrane domain shares at least 90% sequence identity with SEQ ID NO.6 from CD8α.

4. The mesothelin specific chimeric antigen receptor (CAR) according to claim 1, further comprising a hinge between the extracellular ligand-binding domain and the transmembrane domain, wherein said hinge is selected from CD8α hinge, IgG1 hinge and FcγRIIIα hinge.

5. The mesothelin specific chimeric antigen receptor according to claim 1, wherein said CAR comprises a co-stimulatory domain from 4-1BB that has at least 80% identity with SEQ ID NO:18.

6. The mesothelin specific CAR according to claim 1, wherein said CD3 zeta signalling domain has at least 80% identity with SEQ ID NO:19.

7. The mesothelin specific chimeric antigen receptor (CAR) according to claim 1, wherein said CAR has at least 95% overall amino acid sequence identity with SEQ ID NO:21 (Meso1 CAR) or SEQ ID NO:22 (Meso1-R2 CAR).

8. A polynucleotide encoding a chimeric antigen receptor comprising at least:

an extracellular ligand binding-domain comprising VH and VL from a monoclonal anti-mesothelin antibody;

a transmembrane domain; and a cytoplasmic domain comprising a CD3 zeta signalling domain and a co-stimulatory domain, wherein said extracellular ligand binding-domain is directed against the MSLN antigen polypeptide region SEQ ID NO:25, wherein said extracellular ligand binding-domain comprises:

a variable heavy VH chain comprising CDRs from the antibody Meso1 having the amino acid sequence of SEQ ID NO:3 (CDRH1-Meso1), SEQ ID NO:4 (CDRH2-Meso1) and SEQ ID NO:5 (CDRH3-Meso1), and a variable heavy VL chain comprising CDRs from the antibody Meso1 having the amino acid sequence of SEQ ID NO:6 (CDRL1-Meso1), SEQ ID NO:7 (CDRL2-Meso1) and SEQ ID NO:8 (CDRL3-Meso1) according to claim 1.

9. An engineered immune cell comprising a polynucleotide according to claim 8.

10. An engineered immune cell expressing at the cell surface membrane a mesothelin specific chimeric antigen receptor comprising at least:

an extracellular ligand binding-domain comprising VH and VL from a monoclonal anti-mesothelin antibody;

a transmembrane domain; and a cytoplasmic domain comprising a CD3 zeta signalling domain and a co-stimulatory domain, wherein said extracellular ligand binding-domain is directed against the MSLN antigen polypeptide region SEQ ID NO:25, wherein said extracellular ligand binding-domain comprises:

a variable heavy VH chain comprising CDRs from the antibody Meso1 having the amino acid sequence of SEQ ID NO:3 (CDRH1-Meso1), SEQ ID NO:4 (CDRH2-Meso1) and SEQ ID NO:5 (CDRH3-Meso1), and a variable heavy VL chain comprising CDRs from the antibody Meso1 having the amino acid sequence of SEQ ID NO:6 (CDRL1-Meso1), SEQ ID NO:7 (CDRL2-Meso1) and SEQ ID NO:8 (CDRL3-Meso1).

11. An engineered immune cell according to claim 10, wherein expression of TCR is reduced or suppressed in said immune cell.

12. An engineered immune cell according to claim 10, wherein said immune cell is mutated to confer resistance to an anti-CD52 antibody.

13. An engineered immune cell according to claim 10, wherein said immune cell has been further mutated to confer resistance to a purine analogue drug.

14. An engineered immune cell according to claim 10, wherein said immune cell has been mutated in a gene encoding HLA or B2m.

15. An engineered immune cell according to claim 10, wherein said mesothelin-specific chimeric antigen receptor (CAR) is co-expressed in said immune cell with another exogenous genetic sequence encoding an inhibitor or decoy of TGFbeta receptor having at least 80% polypeptide sequence identity with SEQ ID NO.24.

16. An engineered immune cell according to claim 10, wherein said cell has at least one TGFbeta receptor gene expression reduced or inactivated.

17. An engineered immune cell according to claim 10, wherein said mesothelin-specific chimeric antigen receptor (CAR) is co-expressed in said immune cell with another exogenous genetic sequence selected from one encoding:

NK cell inhibitor selected from the group consisting of HLAG, HLAE or ULBP1;

CRS inhibitor selected from the group consisting of a mutated IL6Ra, sGP130 or IL18-BP; or cytochrome(s) selected from the group consisting of P450, CYP2D6-1, CYP2D6-2, CYP2C9, CYP3A4, CYP2C19 or CYP1A2, conferring hypersensitivity of said immune cells to a drug, cyclophosphamide and/or isophosphamide;

dihydrofolate reductase (DHFR), inosine monophosphate dehydrogenase 2 (IMPDH2), calcineurin or methylguanine transferase (MGMT), mTORmut or Lckmut, conferring drug resistance;

a chemokine or a cytokine selected from the group consisting of IL-2, IL-12 and IL-15;

a chemokine receptor selected from the group consisting of CCR2, CXCR2, or CXCR4; and a secreted inhibitor of Tumor Associated Macrophages (TAM), or a CCR2/CCL2 neutralization agent, to enhance the therapeutic activity of the immune cells.

* * * * *

SEQUENCE LISTING

```
<160> NUMBER OF SEQ ID NOS: 161

<210> SEQ ID NO 1
<211> LENGTH: 127
<212> TYPE: PRT
<213> ORGANISM: artificial
<220> FEATURE:
<223> OTHER INFORMATION: P4 heavy chain variable region

<400> SEQUENCE: 1

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Tyr Gly Met Asp Val
            100                 105                 110

Trp Gly Gln Gly Thr Thr Val Thr Val Ser Ser Gly Ile Leu Gly
        115                 120                 125


<210> SEQ ID NO 2
<211> LENGTH: 116
<212> TYPE: PRT
<213> ORGANISM: artificial
<220> FEATURE:
<223> OTHER INFORMATION: P4 light chain variable region

<400> SEQUENCE: 2

Gln Pro Val Leu Thr Gln Ser Ser Ser Leu Ser Ala Ser Pro Gly Ala
1               5                   10                  15

Ser Ala Ser Leu Thr Cys Thr Leu Arg Ser Gly Ile Asn Val Gly Pro
            20                  25                  30

Tyr Arg Ile Tyr Trp Tyr Gln Gln Lys Pro Gly Ser Pro Pro Gln Tyr
        35                  40                  45

Leu Leu Asn Tyr Lys Ser Asp Ser Asp Lys Gln Gln Gly Ser Gly Val
```

```
    50                  55                  60

Pro Ser Arg Phe Ser Gly Ser Lys Asp Ala Ser Ala Asn Ala Gly Val
65                  70                  75                  80

Leu Leu Ile Ser Gly Leu Arg Ser Glu Asp Glu Ala Asp Tyr Tyr Cys
                85                  90                  95

Met Ile Trp His Ser Ser Ala Ala Val Phe Gly Gly Gly Thr Gln Leu
            100                 105                 110

Thr Val Leu Ser
        115


<210> SEQ ID NO 3
<211> LENGTH: 5
<212> TYPE: PRT
<213> ORGANISM: artificial
<220> FEATURE:
<223> OTHER INFORMATION: CDRH1- meso1

<400> SEQUENCE: 3

Ser Tyr Tyr Trp Ser
1               5


<210> SEQ ID NO 4
<211> LENGTH: 16
<212> TYPE: PRT
<213> ORGANISM: artificial
<220> FEATURE:
<223> OTHER INFORMATION: CDRH2- meso1

<400> SEQUENCE: 4

Tyr Ile Tyr Tyr Ser Gly Ser Thr Asn Tyr Asn Pro Ser Leu Lys Ser
1               5                   10                  15


<210> SEQ ID NO 5
<211> LENGTH: 8
<212> TYPE: PRT
<213> ORGANISM: artificial
<220> FEATURE:
<223> OTHER INFORMATION: CDRH3- meso1

<400> SEQUENCE: 5

Val Asp Tyr Lys Ala Phe Asp Ile
1               5


<210> SEQ ID NO 6
<211> LENGTH: 11
<212> TYPE: PRT
<213> ORGANISM: artificial
<220> FEATURE:
<223> OTHER INFORMATION: CDRL1- meso1

<400> SEQUENCE: 6

Arg Ala Ser Gln Gly Ile Arg Asn Asp Leu His
1               5                   10


<210> SEQ ID NO 7
<211> LENGTH: 7
<212> TYPE: PRT
<213> ORGANISM: artificial
<220> FEATURE:
<223> OTHER INFORMATION: CDRL2- meso1

<400> SEQUENCE: 7

Ala Ala Ser Ser Leu Gln Ser
1               5
```

<210> SEQ ID NO 8
<211> LENGTH: 9
<212> TYPE: PRT
<213> ORGANISM: artificial
<220> FEATURE:
<223> OTHER INFORMATION: CDRL3- meso1

<400> SEQUENCE: 8

Leu Gln His Tyr Ser Tyr Pro Trp Thr
1               5

<210> SEQ ID NO 9
<211> LENGTH: 116
<212> TYPE: PRT
<213> ORGANISM: artificial
<220> FEATURE:
<223> OTHER INFORMATION: meso1 heavy chain variable region

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Asp Tyr Lys Ala Phe Asp Ile Trp Gly Gln Gly Thr Met Val
            100                 105                 110

Thr Val Ser Ser
        115

<210> SEQ ID NO 10
<211> LENGTH: 107
<212> TYPE: PRT
<213> ORGANISM: artificial
<220> FEATURE:
<223> OTHER INFORMATION: meso1 light chain variable region

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu His Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Tyr Ser Tyr Pro Trp
                85                  90                  95

Thr Phe Gly Gln Gly Thr Lys Val Glu Ile Lys
            100                 105

<210> SEQ ID NO 11
<211> LENGTH: 121
<212> TYPE: PRT
<213> ORGANISM: artificial
<220> FEATURE:
<223> OTHER INFORMATION: meso2 heavy chain variable region

<400> SEQUENCE: 11

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Val Ile Met Pro Ser Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly His Gly Met Tyr Gly Gly Ala Leu Asp Val Trp Gly
            100                 105                 110

Gln Gly Thr Leu Val Thr Val Ser Ser
        115                 120
```

<210> SEQ ID NO 12
<211> LENGTH: 111
<212> TYPE: PRT
<213> ORGANISM: artificial
<220> FEATURE:
<223> OTHER INFORMATION: meso2 light chain variable region

<400> SEQUENCE: 12

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Arg Leu Ala Trp Tyr Gln Gln Lys Pro Gly Gln Ala Pro Arg Leu Leu
        35                  40                  45

Ile Tyr Gly Ala Ser Lys Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Asp Pro
                85                  90                  95

Ser Gly Thr Phe Gly Gln Gly Thr Lys Val Glu Ile Lys Arg Thr
            100                 105                 110
```

<210> SEQ ID NO 13
<211> LENGTH: 15
<212> TYPE: PRT
<213> ORGANISM: artificial
<220> FEATURE:
<223> OTHER INFORMATION: Linker

<400> SEQUENCE: 13

```
Gly Gly Gly Gly Ser Gly Gly Gly Gly Ser Gly Gly Gly Gly Ser
1               5                   10                  15
```

<210> SEQ ID NO 14

<211> LENGTH: 21
<212> TYPE: PRT
<213> ORGANISM: artificial
<220> FEATURE:
<223> OTHER INFORMATION: CD8α signal peptide

<400> SEQUENCE: 14

Met Ala Leu Pro Val Thr Ala Leu Leu Leu Pro Leu Ala Leu Leu Leu
1 5 10 15

His Ala Ala Arg Pro
20

<210> SEQ ID NO 15
<211> LENGTH: 40
<212> TYPE: PRT
<213> ORGANISM: artificial
<220> FEATURE:
<223> OTHER INFORMATION: R2 suicide switch

<400> SEQUENCE: 15

Ser Asp Pro Gly Ser Gly Gly Gly Gly Ser Cys Pro Tyr Ser Asn Pro
1 5 10 15

Ser Leu Cys Ser Gly Gly Gly Gly Ser Cys Pro Tyr Ser Asn Pro Ser
20 25 30

Leu Cys Ser Gly Gly Gly Gly Ser
35 40

<210> SEQ ID NO 16
<211> LENGTH: 45
<212> TYPE: PRT
<213> ORGANISM: artificial
<220> FEATURE:
<223> OTHER INFORMATION: CD8α hinge

<400> SEQUENCE: 16

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 17
<211> LENGTH: 24
<212> TYPE: PRT
<213> ORGANISM: artificial
<220> FEATURE:
<223> OTHER INFORMATION: CD8α transmembrane domain

<400> SEQUENCE: 17

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 18
<211> LENGTH: 42
<212> TYPE: PRT
<213> ORGANISM: artificial
<220> FEATURE:
<223> OTHER INFORMATION: 4-1BB co-stimulatory domain

<400> SEQUENCE: 18

Lys Arg Gly Arg Lys Lys Leu Leu Tyr Ile Phe Lys Gln Pro Phe Met

```
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 19
<211> LENGTH: 112
<212> TYPE: PRT
<213> ORGANISM: artificial
<220> FEATURE:
<223> OTHER INFORMATION: CD3&#950; signalling domain

<400> SEQUENCE: 19

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 20
<211> LENGTH: 542
<212> TYPE: PRT
<213> ORGANISM: artificial
<220> FEATURE:
<223> OTHER INFORMATION: P4-R2 CAR full sequence

<400> SEQUENCE: 20

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Thr Pro Ser Gln Thr Leu Ser Leu Thr Cys Ala Ile Ser Gly Asp
        35                  40                  45

Ser Val Ser Ser Asn Ser Ala Thr Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Met Ser Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Gly Met Met Thr Tyr Tyr
        115                 120                 125

Tyr Gly Met Asp Val Trp Gly Gln Gly Thr Thr Val Thr Val Ser Ser
    130                 135                 140

Gly Ile Leu Gly Gly Gly Gly Gly Ser Gly Gly Gly Gly Ser Gly Gly
145                 150                 155                 160
```

```
Gly Gly Ser Gln Pro Val Leu Thr Gln Ser Ser Ser Leu Ser Ala Ser
                165                 170                 175

Pro Gly Ala Ser Ala Ser Leu Thr Cys Thr Leu Arg Ser Gly Ile Asn
            180                 185                 190

Val Gly Pro Tyr Arg Ile Tyr Trp Tyr Gln Gln Lys Pro Gly Ser Pro
        195                 200                 205

Pro Gln Tyr Leu Leu Asn Tyr Lys Ser Asp Ser Asp Lys Gln Gln Gly
    210                 215                 220

Ser Gly Val Pro Ser Arg Phe Ser Gly Ser Lys Asp Ala Ser Ala Asn
225                 230                 235                 240

Ala Gly Val Leu Leu Ile Ser Gly Leu Arg Ser Glu Asp Glu Ala Asp
                245                 250                 255

Tyr Tyr Cys Met Ile Trp His Ser Ser Ala Ala Val Phe Gly Gly Gly
            260                 265                 270

Thr Gln Leu Thr Val Leu Ser Ser Asp Pro Gly Ser Gly Gly Gly Gly
        275                 280                 285

Ser Cys Pro Tyr Ser Asn Pro Ser Leu Cys Ser Gly Gly Gly Gly Ser
    290                 295                 300

Cys Pro Tyr Ser Asn Pro Ser Leu Cys Ser Gly Gly Gly Gly Ser Thr
305                 310                 315                 320

Thr Thr Pro Ala Pro Arg Pro Pro Thr Pro Ala Pro Thr Ile Ala Ser
                325                 330                 335

Gln Pro Leu Ser Leu Arg Pro Glu Ala Cys Arg Pro Ala Ala Gly Gly
            340                 345                 350

Ala Val His Thr Arg Gly Leu Asp Phe Ala Cys Asp Ile Tyr Ile Trp
        355                 360                 365

Ala Pro Leu Ala Gly Thr Cys Gly Val Leu Leu Leu Ser Leu Val Ile
    370                 375                 380

Thr Leu Tyr Cys Lys Arg Gly Arg Lys Lys Leu Leu Tyr Ile Phe Lys
385                 390                 395                 400

Gln Pro Phe Met Arg Pro Val Gln Thr Thr Gln Glu Glu Asp Gly Cys
                405                 410                 415

Ser Cys Arg Phe Pro Glu Glu Glu Glu Gly Gly Cys Glu Leu Arg Val
            420                 425                 430

Lys Phe Ser Arg Ser Ala Asp Ala Pro Ala Tyr Gln Gln Gly Gln Asn
        435                 440                 445

Gln Leu Tyr Asn Glu Leu Asn Leu Gly Arg Arg Glu Glu Tyr Asp Val
    450                 455                 460

Leu Asp Lys Arg Arg Gly Arg Asp Pro Glu Met Gly Gly Lys Pro Arg
465                 470                 475                 480

Arg Lys Asn Pro Gln Glu Gly Leu Tyr Asn Glu Leu Gln Lys Asp Lys
                485                 490                 495

Met Ala Glu Ala Tyr Ser Glu Ile Gly Met Lys Gly Glu Arg Arg Arg
            500                 505                 510

Gly Lys Gly His Asp Gly Leu Tyr Gln Gly Leu Ser Thr Ala Thr Lys
        515                 520                 525

Asp Thr Tyr Asp Ala Leu His Met Gln Ala Leu Pro Pro Arg
    530                 535                 540
```

<210> SEQ ID NO 21
<211> LENGTH: 522
<212> TYPE: PRT
<213> ORGANISM: artificial
<220> FEATURE:
<223> OTHER INFORMATION: meso1-R2 CAR full sequence

<400> SEQUENCE: 21

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Val Asp Tyr Lys Ala Phe Asp Ile Trp Gly
        115                 120                 125

Gln Gly Thr Met Val Thr Val Ser Ser Gly Gly Gly Gly Ser Gly Gly
    130                 135                 140

Gly Gly Ser Gly Gly Gly Gly Ser Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Gly Ile Arg Asn Asp Leu His Trp Tyr Gln Gln Lys Pro
            180                 185                 190

Gly Lys Ala Pro Lys Arg Leu Ile Tyr Ala Ala Ser Ser Leu Gln Ser
        195                 200                 205

Gly Val Pro Ser Arg Phe Ser Gly Ser Gly Ser Gly Thr Glu Phe Thr
    210                 215                 220

Leu Thr Ile Ser Ser Leu Gln Pro Glu Asp Phe Ala Thr Tyr Tyr Cys
225                 230                 235                 240

Leu Gln His Tyr Ser Tyr Pro Trp Thr Phe Gly Gln Gly Thr Lys Val
                245                 250                 255

Glu Ile Lys Ser Asp Pro Gly Ser Gly Gly Gly Gly Ser Cys Pro Tyr
            260                 265                 270

Ser Asn Pro Ser Leu Cys Ser Gly Gly Gly Gly Ser Cys Pro Tyr Ser
        275                 280                 285

Asn Pro Ser Leu Cys Ser Gly Gly Gly Gly Ser Thr Thr Thr Pro Ala
    290                 295                 300

Pro Arg Pro Pro Thr Pro Ala Pro Thr Ile Ala Ser Gln Pro Leu Ser
305                 310                 315                 320

Leu Arg Pro Glu Ala Cys Arg Pro Ala Ala Gly Gly Ala Val His Thr
                325                 330                 335

Arg Gly Leu Asp Phe Ala Cys Asp Ile Tyr Ile Trp Ala Pro Leu Ala
            340                 345                 350

Gly Thr Cys Gly Val Leu Leu Leu Ser Leu Val Ile Thr Leu Tyr Cys
        355                 360                 365

Lys Arg Gly Arg Lys Lys Leu Leu Tyr Ile Phe Lys Gln Pro Phe Met
    370                 375                 380

Arg Pro Val Gln Thr Thr Gln Glu Glu Asp Gly Cys Ser Cys Arg Phe
385                 390                 395                 400

Pro Glu Glu Glu Glu Gly Gly Cys Glu Leu Arg Val Lys Phe Ser Arg
```

```
                405                 410                 415

Ser Ala Asp Ala Pro Ala Tyr Gln Gln Gly Gln Asn Gln Leu Tyr Asn
            420                 425                 430

Glu Leu Asn Leu Gly Arg Arg Glu Glu Tyr Asp Val Leu Asp Lys Arg
        435                 440                 445

Arg Gly Arg Asp Pro Glu Met Gly Gly Lys Pro Arg Arg Lys Asn Pro
    450                 455                 460

Gln Glu Gly Leu Tyr Asn Glu Leu Gln Lys Asp Lys Met Ala Glu Ala
465                 470                 475                 480

Tyr Ser Glu Ile Gly Met Lys Gly Glu Arg Arg Arg Gly Lys Gly His
                485                 490                 495

Asp Gly Leu Tyr Gln Gly Leu Ser Thr Ala Thr Lys Asp Thr Tyr Asp
            500                 505                 510

Ala Leu His Met Gln Ala Leu Pro Pro Arg
        515                 520


<210> SEQ ID NO 22
<211> LENGTH: 482
<212> TYPE: PRT
<213> ORGANISM: artificial
<220> FEATURE:
<223> OTHER INFORMATION: meso1 CAR full sequence

<400> SEQUENCE: 22

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Val Asp Tyr Lys Ala Phe Asp Ile Trp Gly
        115                 120                 125

Gln Gly Thr Met Val Thr Val Ser Ser Gly Gly Gly Gly Ser Gly Gly
    130                 135                 140

Gly Gly Ser Gly Gly Gly Gly Ser Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Gly Ile Arg Asn Asp Leu His Trp Tyr Gln Gln Lys Pro
            180                 185                 190

Gly Lys Ala Pro Lys Arg Leu Ile Tyr Ala Ala Ser Ser Leu Gln Ser
        195                 200                 205

Gly Val Pro Ser Arg Phe Ser Gly Ser Gly Ser Gly Thr Glu Phe Thr
    210                 215                 220

Leu Thr Ile Ser Ser Leu Gln Pro Glu Asp Phe Ala Thr Tyr Tyr Cys
225                 230                 235                 240

Leu Gln His Tyr Ser Tyr Pro Trp Thr Phe Gly Gln Gly Thr Lys Val
```

```
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg


<210> SEQ ID NO 23
<211> LENGTH: 531
<212> TYPE: PRT
<213> ORGANISM: artificial
<220> FEATURE:
<223> OTHER INFORMATION: meso2-R2 full sequence

<400> SEQUENCE: 23

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Glu Ser Leu Lys Ile Ser Cys Lys Gly Ser Gly Tyr
        35                  40                  45

Ser Phe Thr Asn Tyr Trp Ile Gly Trp Val Arg Gln Met Pro Gly Lys
    50                  55                  60

Gly Leu Glu Trp Met Gly Val Ile Met Pro Ser Asp Ser Tyr Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Ser Ser Leu Lys Ala Ser Asp Thr
            100                 105                 110

Ala Met Tyr Tyr Cys Ala Arg Tyr Gly His Gly Met Tyr Gly Gly Ala
        115                 120                 125
```

```
Leu Asp Val Trp Gly Gln Gly Thr Leu Val Thr Val Ser Ser Gly Gly
    130                 135                 140

Gly Gly Ser Gly Gly Gly Gly Ser Gly Gly Gly Gly Ser Asp Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Arg Ser Ser Arg Leu Ala
            180                 185                 190

Trp Tyr Gln Gln Lys Pro Gly Gln Ala Pro Arg Leu Leu Ile Tyr Gly
        195                 200                 205

Ala Ser Lys Arg Ala Thr Gly Val Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Tyr Ser His Asp Pro Ser Gly Thr
                245                 250                 255

Phe Gly Gln Gly Thr Lys Val Glu Ile Lys Arg Thr Ser Asp Pro Gly
            260                 265                 270

Ser Gly Gly Gly Gly Ser Cys Pro Tyr Ser Asn Pro Ser Leu Cys Ser
        275                 280                 285

Gly Gly Gly Gly Ser Cys Pro Tyr Ser Asn Pro Ser Leu Cys Ser Gly
    290                 295                 300

Gly Gly Gly Ser Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365

Leu Ser Leu Val Ile Thr Leu Tyr Cys Lys Arg Gly Arg Lys Lys Leu
    370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
        435                 440                 445

Glu Glu Tyr Asp Val Leu Asp Lys Arg Arg Gly Arg Asp Pro Glu Met
    450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg
    530
```

<210> SEQ ID NO 24
<211> LENGTH: 199
<212> TYPE: PRT
<213> ORGANISM: artificial
<220> FEATURE:
<223> OTHER INFORMATION: dominant negative dnTGFβRII

<400> SEQUENCE: 24

Met Gly Arg Gly Leu Leu Arg Gly Leu Trp Pro Leu His Ile Val Leu
1 5 10 15

Trp Thr Arg Ile Ala Ser Thr Ile Pro Pro His Val Gln Lys Ser Val
20 25 30

Asn Asn Asp Met Ile Val Thr Asp Asn Asn Gly Ala Val Lys Phe Pro
35 40 45

Gln Leu Cys Lys Phe Cys Asp Val Arg Phe Ser Thr Cys Asp Asn Gln
50 55 60

Lys Ser Cys Met Ser Asn Cys Ser Ile Thr Ser Ile Cys Glu Lys Pro
65 70 75 80

Gln Glu Val Cys Val Ala Val Trp Arg Lys Asn Asp Glu Asn Ile Thr
85 90 95

Leu Glu Thr Val Cys His Asp Pro Lys Leu Pro Tyr His Asp Phe Ile
100 105 110

Leu Glu Asp Ala Ala Ser Pro Lys Cys Ile Met Lys Glu Lys Lys Lys
115 120 125

Pro Gly Glu Thr Phe Phe Met Cys Ser Cys Ser Ser Asp Glu Cys Asn
130 135 140

Asp Asn Ile Ile Phe Ser Glu Glu Tyr Asn Thr Ser Asn Pro Asp Leu
145 150 155 160

Leu Leu Val Ile Phe Gln Val Thr Gly Ile Ser Leu Leu Pro Pro Leu
165 170 175

Gly Val Ala Ile Ser Val Ile Ile Ile Phe Tyr Cys Tyr Arg Val Asn
180 185 190

Arg Gln Gln Lys Leu Ser Ser
195

<210> SEQ ID NO 25
<211> LENGTH: 291
<212> TYPE: PRT
<213> ORGANISM: homo sapiens
<220> FEATURE:
<223> OTHER INFORMATION: MSLN target antigen region

<400> SEQUENCE: 25

Glu Val Glu Lys Thr Ala Cys Pro Ser Gly Lys Lys Ala Arg Glu Ile
1 5 10 15

Asp Glu Ser Leu Ile Phe Tyr Lys Lys Trp Glu Leu Glu Ala Cys Val
20 25 30

Asp Ala Ala Leu Leu Ala Thr Gln Met Asp Arg Val Asn Ala Ile Pro
35 40 45

Phe Thr Tyr Glu Gln Leu Asp Val Leu Lys His Lys Leu Asp Glu Leu
50 55 60

Tyr Pro Gln Gly Tyr Pro Glu Ser Val Ile Gln His Leu Gly Tyr Leu
65 70 75 80

Phe Leu Lys Met Ser Pro Glu Asp Ile Arg Lys Trp Asn Val Thr Ser
85 90 95

Leu Glu Thr Leu Lys Ala Leu Leu Glu Val Asn Lys Gly His Glu Met
100 105 110

```
Ser Pro Gln Ala Pro Arg Arg Pro Leu Pro Gln Val Ala Thr Leu Ile
        115                 120                 125

Asp Arg Phe Val Lys Gly Arg Gly Gln Leu Asp Lys Asp Thr Leu Asp
    130                 135                 140

Thr Leu Thr Ala Phe Tyr Pro Gly Tyr Leu Cys Ser Leu Ser Pro Glu
145                 150                 155                 160

Glu Leu Ser Ser Val Pro Pro Ser Ser Ile Trp Ala Val Arg Pro Gln
                165                 170                 175

Asp Leu Asp Thr Cys Asp Pro Arg Gln Leu Asp Val Leu Tyr Pro Lys
            180                 185                 190

Ala Arg Leu Ala Phe Gln Asn Met Asn Gly Ser Glu Tyr Phe Val Lys
        195                 200                 205

Ile Gln Ser Phe Leu Gly Gly Ala Pro Thr Glu Asp Leu Lys Ala Leu
    210                 215                 220

Ser Gln Gln Asn Val Ser Met Asp Leu Ala Thr Phe Met Lys Leu Arg
225                 230                 235                 240

Thr Asp Ala Val Leu Pro Leu Thr Val Ala Glu Val Gln Lys Leu Leu
                245                 250                 255

Gly Pro His Val Glu Gly Leu Lys Ala Glu Glu Arg His Arg Pro Val
            260                 265                 270

Arg Asp Trp Ile Leu Arg Gln Arg Gln Asp Asp Leu Asp Thr Leu Gly
        275                 280                 285

Leu Gly Leu
    290


<210> SEQ ID NO 26
<211> LENGTH: 9
<212> TYPE: PRT
<213> ORGANISM: artificial
<220> FEATURE:
<223> OTHER INFORMATION: Mimotope R2 (Rituximab)

<400> SEQUENCE: 26

Cys Pro Tyr Ser Asn Pro Ser Leu Cys
1               5


<210> SEQ ID NO 27
<211> LENGTH: 24
<212> TYPE: PRT
<213> ORGANISM: artificial
<220> FEATURE:
<223> OTHER INFORMATION: Palivizumab epitope

<400> SEQUENCE: 27

Asn Ser Glu Leu Leu Ser Leu Ile Asn Asp Met Pro Ile Thr Asn Asp
1               5                   10                  15

Gln Lys Lys Leu Met Ser Asn Asn
            20


<210> SEQ ID NO 28
<211> LENGTH: 12
<212> TYPE: PRT
<213> ORGANISM: artificial
<220> FEATURE:
<223> OTHER INFORMATION: Cetuximab epitope 1

<400> SEQUENCE: 28

Cys Gln Phe Asp Leu Ser Thr Arg Arg Leu Lys Cys
1               5                   10
```

<210> SEQ ID NO 29
<211> LENGTH: 12
<212> TYPE: PRT
<213> ORGANISM: artificial
<220> FEATURE:
<223> OTHER INFORMATION: Cetuximab epitope 2

<400> SEQUENCE: 29

Cys Gln Tyr Asn Leu Ser Ser Arg Ala Leu Lys Cys
1 5 10

<210> SEQ ID NO 30
<211> LENGTH: 12
<212> TYPE: PRT
<213> ORGANISM: artificial
<220> FEATURE:
<223> OTHER INFORMATION: Cetuximab epitope 3

<400> SEQUENCE: 30

Cys Val Trp Gln Arg Trp Gln Lys Ser Tyr Val Cys
1 5 10

<210> SEQ ID NO 31
<211> LENGTH: 12
<212> TYPE: PRT
<213> ORGANISM: artificial
<220> FEATURE:
<223> OTHER INFORMATION: Cetuximab epitope 4

<400> SEQUENCE: 31

Cys Met Trp Asp Arg Phe Ser Arg Trp Tyr Lys Cys
1 5 10

<210> SEQ ID NO 32
<211> LENGTH: 25
<212> TYPE: PRT
<213> ORGANISM: artificial
<220> FEATURE:
<223> OTHER INFORMATION: Nivolumab epitope 1

<400> SEQUENCE: 32

Ser Phe Val Leu Asn Trp Tyr Arg Met Ser Pro Ser Asn Gln Thr Asp
1 5 10 15

Lys Leu Ala Ala Phe Pro Glu Asp Arg
20 25

<210> SEQ ID NO 33
<211> LENGTH: 19
<212> TYPE: PRT
<213> ORGANISM: artificial
<220> FEATURE:
<223> OTHER INFORMATION: Nivolumab epitope 2

<400> SEQUENCE: 33

Ser Gly Thr Tyr Leu Cys Gly Ala Ile Ser Leu Ala Pro Lys Ala Gln
1 5 10 15

Ile Lys Glu

<210> SEQ ID NO 34
<211> LENGTH: 24
<212> TYPE: PRT
<213> ORGANISM: artificial
<220> FEATURE:
<223> OTHER INFORMATION: QBEND-10 Epitope

<400> SEQUENCE: 34

```
Glu Leu Pro Thr Gln Gly Thr Phe Ser Asn Val Ser Thr Asn Val Ser
1               5                   10                  15

Pro Ala Lys Pro Thr Thr Thr Ala
            20


<210> SEQ ID NO 35
<211> LENGTH: 12
<212> TYPE: PRT
<213> ORGANISM: artificial
<220> FEATURE:
<223> OTHER INFORMATION: Alemtuzumab epitope

<400> SEQUENCE: 35

Gly Gln Asn Asp Thr Ser Gln Thr Ser Ser Pro Ser
1               5                   10


<210> SEQ ID NO 36
<211> LENGTH: 49
<212> TYPE: DNA
<213> ORGANISM: homo sapiens
<220> FEATURE:
<223> OTHER INFORMATION: T003387 target sequence TGFbetaRII

<400> SEQUENCE: 36

ttttgtttcc ccatcagaat ataacaccag caatcctgac ttgttgcta                 49


<210> SEQ ID NO 37
<211> LENGTH: 49
<212> TYPE: DNA
<213> ORGANISM: homo sapiens
<220> FEATURE:
<223> OTHER INFORMATION: T003401 target sequence TGFbetaRII

<400> SEQUENCE: 37

tccctatgag gagtatgcct cttggaagac agagaaggac atcttctca                 49


<210> SEQ ID NO 38
<211> LENGTH: 49
<212> TYPE: DNA
<213> ORGANISM: homo sapiens
<220> FEATURE:
<223> OTHER INFORMATION: T003400 target sequence TGFbetaRII

<400> SEQUENCE: 38

tccctatgag gagtatgcct cttggaagac agagaaggac atcttctca                 49


<210> SEQ ID NO 39
<211> LENGTH: 49
<212> TYPE: DNA
<213> ORGANISM: homo sapiens
<220> FEATURE:
<223> OTHER INFORMATION: T003405 target sequence TGFbetaRII

<400> SEQUENCE: 39

tgtgggaggc ccaagatgcc catcgtgcac agggacctca agagctcca                 49


<210> SEQ ID NO 40
<211> LENGTH: 23
<212> TYPE: DNA
<213> ORGANISM: homo sapiens
<220> FEATURE:
<223> OTHER INFORMATION: CRISPR target sequences for TGF&#946;RII gene

<400> SEQUENCE: 40

acagtgatca cactccatgt ggg                                             23
```

<210> SEQ ID NO 41
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 41
gcagaagctg agttcaacct ggg 23

<210> SEQ ID NO 42
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 42
aggttaggtc gttcttcacg agg 23

<210> SEQ ID NO 43
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 43
aaagcgacct ttccccacca ggg 23

<210> SEQ ID NO 44
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 44
tggatgacct ggctaacagt ggg 23

<210> SEQ ID NO 45
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 45
cctgggaaac cggcaagacg cgg 23

<210> SEQ ID NO 46
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 46
acagatatgg caactcccag tgg 23

<210> SEQ ID NO 47
<211> LENGTH: 23
<212> TYPE: DNA
<213> ORGANISM: homo sapiens
<220> FEATURE:

<223> OTHER INFORMATION: CRISPR target sequences for TGFβRII gene

<400> SEQUENCE: 47
gtggaggtga gcaatccccc ggg 23

<210> SEQ ID NO 48
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 48
acctacagga gtacctgacg cgg 23

<210> SEQ ID NO 49
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 49
gtgatcacac tccatgtggg agg 23

<210> SEQ ID NO 50
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 50
gctggtgtta tattctgatg ggg 23

<210> SEQ ID NO 51
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 51
cacagtgatc acactccatg tgg 23

<210> SEQ ID NO 52
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 52
cacatggagt gtgatcactg tgg 23

<210> SEQ ID NO 53
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 53
cagagtaggg tccagacgca ggg 23

<210> SEQ ID NO 54
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 54
gcttctgctg ccggttaacg cgg 23

<210> SEQ ID NO 55
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 55
gtggatgacc tggctaacag tgg 23

<210> SEQ ID NO 56
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 56
gggaaagccc aaagtcacac agg 23

<210> SEQ ID NO 57
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 57
aatatgacta gcaacaagtc agg 23

<210> SEQ ID NO 58
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 58
atggagtgtg atcactgtgg agg 23

<210> SEQ ID NO 59
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 59
atcaccgcct tccacgccaa ggg 23

<210> SEQ ID NO 60
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 60
aggagcggaa gacggagttg ggg 23

<210> SEQ ID NO 61
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 61
ccacgccaag ggcaacctac agg 23

<210> SEQ ID NO 62
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 62
caagatgccc atcgtgcaca ggg 23

<210> SEQ ID NO 63
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 63
gatatggcaa ctcccagtgg tgg 23

<210> SEQ ID NO 64
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 64
agcagaagct gagttcaacc tgg 23

<210> SEQ ID NO 65
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 65
cctgtaggtt gcccttggcg tgg 23

<210> SEQ ID NO 66
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 66
gtgagcaatc ccccgggcga ggg 23

<210> SEQ ID NO 67
<211> LENGTH: 23

<212> TYPE: DNA
<213> ORGANISM: homo sapiens
<220> FEATURE:
<223> OTHER INFORMATION: CRISPR target sequences for TGFβRII gene

<400> SEQUENCE: 67
acagagtagg gtccagacgc agg 23

<210> SEQ ID NO 68
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 68
tagcaacaag tcaggattgc tgg 23

<210> SEQ ID NO 69
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 69
ccaagatgcc catcgtgcac agg 23

<210> SEQ ID NO 70
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 70
tgtggaggtg agcaatcccc cgg 23

<210> SEQ ID NO 71
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 71
tgcctcttgg aagacagaga agg 23

<210> SEQ ID NO 72
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 72
gcccattgag ctggacaccc tgg 23

<210> SEQ ID NO 73
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 73
ctgagttcaa cctgggaaac cgg 23

<210> SEQ ID NO 74
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 74
tgggaggacc tgcgcaagct ggg 23

<210> SEQ ID NO 75
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 75
gtactcctgt aggttgccct tgg 23

<210> SEQ ID NO 76
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 76
tcttccgctc ctcagccgtc agg 23

<210> SEQ ID NO 77
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 77
ctgggcagct ccctcgcccg ggg 23

<210> SEQ ID NO 78
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 78
cattgagctg gacaccctgg tgg 23

<210> SEQ ID NO 79
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 79
tggcaactcc cagtggtggc agg 23

<210> SEQ ID NO 80
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 80
caactcccag tggtggcagg agg 23

<210> SEQ ID NO 81
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 81
cgagcactgt gccatcatcc tgg 23

<210> SEQ ID NO 82
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 82
gcggtcatct tccaggatga tgg 23

<210> SEQ ID NO 83
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 83
agagctgctg cccattgagc tgg 23

<210> SEQ ID NO 84
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 84
accagggtgt ccagctcaat ggg 23

<210> SEQ ID NO 85
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 85
ctggacaccc tggtggggaa agg 23

<210> SEQ ID NO 86
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 86
caaagcgacc tttccccacc agg 23

<210> SEQ ID NO 87
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 87
gacggctgag gagcggaaga cgg 23

<210> SEQ ID NO 88
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 88
tactctgtct gtggatgacc tgg 23

<210> SEQ ID NO 89
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 89
cggcaagacg cggaagctca tgg 23

<210> SEQ ID NO 90
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 90
cccaaagtca cacaggcagc agg 23

<210> SEQ ID NO 91
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 91
taggttgccc ttggcgtgga agg 23

<210> SEQ ID NO 92
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 92
tgaggagcgg aagacggagt tgg 23

<210> SEQ ID NO 93
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 93
cctgtgcacg atgggcatct tgg 23

<210> SEQ ID NO 94
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 94
gggagctgcc cagcttgcgc agg 23

<210> SEQ ID NO 95
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 95
ttgaactcag cttctgctgc cgg 23

<210> SEQ ID NO 96
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 96
ccaagaggca tactcctcat agg 23

<210> SEQ ID NO 97
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 97
catgagcttc cgcgtcttgc cgg 23

<210> SEQ ID NO 98
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 98
cggagttggg gaaacaatac tgg 23

<210> SEQ ID NO 99
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 99
gctcctcagc cgtcaggaac tgg 23

<210> SEQ ID NO 100

<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 100
caccagggtg tccagctcaa tgg 23

<210> SEQ ID NO 101
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 101
ctagtcatat ttcaagtgac agg 23

<210> SEQ ID NO 102
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 102
gctgggcagc tccctcgccc ggg 23

<210> SEQ ID NO 103
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 103
tgtcagagcg gtcatcttcc agg 23

<210> SEQ ID NO 104
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 104
ctgggaggac ctgcgcaagc tgg 23

<210> SEQ ID NO 105
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 105
agctgggcag ctccctcgcc cgg 23

<210> SEQ ID NO 106
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 106
tgtgttgtgg ttgatgttgt tgg 23

<210> SEQ ID NO 107
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 107
cctgctgcct gtgtgacttt ggg 23

<210> SEQ ID NO 108
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 108
acctgctgcc tgtgtgactt tgg 23

<210> SEQ ID NO 109
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 109
gacgcggcat gtcatcagct ggg 23

<210> SEQ ID NO 110
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 110
ggtcatccac agacagagta ggg 23

<210> SEQ ID NO 111
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 111
agtcaagatc tttccctatg agg 23

<210> SEQ ID NO 112
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 112
gaacatactc cagttcctga cgg 23

<210> SEQ ID NO 113
<211> LENGTH: 23
<212> TYPE: DNA

<213> ORGANISM: homo sapiens
<220> FEATURE:
<223> OTHER INFORMATION: CRISPR target sequences for TGFβRII gene

<400> SEQUENCE: 113
acgtggagct gatgtcagag cgg 23

<210> SEQ ID NO 114
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 114
ggggaaaggt cgctttgctg agg 23

<210> SEQ ID NO 115
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 115
tctggaccct actctgtctg tgg 23

<210> SEQ ID NO 116
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 116
tgggcagctc cctcgcccgg ggg 23

<210> SEQ ID NO 117
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 117
agctgatgac atgccgcgtc agg 23

<210> SEQ ID NO 118
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 118
gccgcgtcag gtactcctgt agg 23

<210> SEQ ID NO 119
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 119
caagaggcat actcctcata ggg 23

<210> SEQ ID NO 120
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 120
ggtgagcaat cccccgggcg agg 23

<210> SEQ ID NO 121
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 121
ttgctggtgt tatattctga tgg 23

<210> SEQ ID NO 122
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 122
cctatgagga gtatgcctct tgg 23

<210> SEQ ID NO 123
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 123
tgctggtgtt atattctgat ggg 23

<210> SEQ ID NO 124
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 124
cgaggatatt ggagctcttg agg 23

<210> SEQ ID NO 125
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 125
gttgatgttg ttggcacacg tgg 23

<210> SEQ ID NO 126
<211> LENGTH: 23
<212> TYPE: DNA
<213> ORGANISM: homo sapiens
<220> FEATURE:

<223> OTHER INFORMATION: CRISPR target sequences for TGFβRII gene

<400> SEQUENCE: 126
tgacgcggca tgtcatcagc tgg 23

<210> SEQ ID NO 127
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 127
ttgagctgga caccctggtg ggg 23

<210> SEQ ID NO 128
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 128
ttcagagcag tttgagacag tgg 23

<210> SEQ ID NO 129
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 129
gcggcatgtc atcagctggg agg 23

<210> SEQ ID NO 130
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 130
aggtcatcca cagacagagt agg 23

<210> SEQ ID NO 131
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 131
gaagatgatg atgacagata tgg 23

<210> SEQ ID NO 132
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 132
tgacctggct aacagtgggc agg 23

<210> SEQ ID NO 133
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 133
tctactgcta ccgcgttaac cgg 23

<210> SEQ ID NO 134
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 134
gtccttctct gtcttccaag agg 23

<210> SEQ ID NO 135
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 135
attgagctgg acaccctggt ggg 23

<210> SEQ ID NO 136
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 136
gtcgttcttc acgaggatat tgg 23

<210> SEQ ID NO 137
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 137
catcagcctc ctgccaccac tgg 23

<210> SEQ ID NO 138
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 138
agttcctgac ggctgaggag cgg 23

<210> SEQ ID NO 139
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 139
actccagttc ctgacggctg agg 23

<210> SEQ ID NO 140
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 140
cttgaggtcc ctgtgcacga tgg 23

<210> SEQ ID NO 141
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 141
ttgaggtccc tgtgcacgat ggg 23

<210> SEQ ID NO 142
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 142
ccgcgtcttg ccggtttccc agg 23

<210> SEQ ID NO 143
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 143
gttgcccttg gcgtggaagg cgg 23

<210> SEQ ID NO 144
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 144
ctttgggctt tccctgcgtc tgg 23

<210> SEQ ID NO 145
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 145
gatcaccgcc ttccacgcca agg 23

<210> SEQ ID NO 146
<211> LENGTH: 23

<212> TYPE: DNA
<213> ORGANISM: homo sapiens
<220> FEATURE:
<223> OTHER INFORMATION: CRISPR target sequences for TGFβRII gene

<400> SEQUENCE: 146
tgaagtgttc tgcttcagct tgg 23

<210> SEQ ID NO 147
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 147
ctgtgcacga tgggcatctt ggg 23

<210> SEQ ID NO 148
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 148
ggcatcttgg gcctcccaca tgg 23

<210> SEQ ID NO 149
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 149
ttacctgccc actgttagcc agg 23

<210> SEQ ID NO 150
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 150
atcagcctcc tgccaccact ggg 23

<210> SEQ ID NO 151
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 151
tcgctttgct gaggtctata agg 23

<210> SEQ ID NO 152
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 152
agtcacacag gcagcaggtt agg 23

<210> SEQ ID NO 153
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 153
gaggagcgga agacggagtt ggg 23

<210> SEQ ID NO 154
<211> LENGTH: 23
<212> TYPE: DNA
<213> ORGANISM: homo sapiens
<220> FEATURE:
<223> OTHER INFORMATION: CRISPR target sequences for TGFβRII gene

<400> SEQUENCE: 154
tgggcagcag ctctgtgttg tgg 23

<210> SEQ ID NO 155
<211> LENGTH: 2781
<212> TYPE: DNA
<213> ORGANISM: artificial
<220> FEATURE:
<223> OTHER INFORMATION: R-TALEN TGFbRII pCLS32939

<400> SEQUENCE: 155
atgggcgatc ctaaaaagaa acgtaaggtc atcgatatcg ccgatctacg cacgctcggc 60
tacagccagc agcaacagga gaagatcaaa ccgaaggttc gttcgacagt ggcgcagcac 120
cacgaggcac tggtcggcca cgggtttaca cacgcgcaca tcgttgcgtt aagccaacac 180
ccggcagcgt tagggaccgt cgctgtcaag tatcaggaca tgatcgcagc gttgccagag 240
gcgacacacg aagcgatcgt tggcgtcggc aaacagtggt ccggcgcacg cgctctggag 300
gccttgctca cggtggcggg agagttgaga ggtccaccgt tacagttgga cacaggccaa 360
cttctcaaga ttgcaaaacg tggcggcgtg accgcagtgg aggcagtgca tgcatggcgc 420
aatgcactga cgggtgcccc gctcaacttg acccccccagc aggtggtggc catcgccagc 480
aatggcggtg gcaagcaggc gctggagacg gtccagcggc tgttgccggt gctgtgccag 540
gcccacggct tgaccccccca gcaggtggtg gccatcgcca gcaatggcgg tggcaagcag 600
gcgctggaga cggtccagcg gctgttgccg gtgctgtgcc aggcccacgg cttgaccccc 660
cagcaggtgg tggccatcgc cagcaatggc ggtggcaagc aggcgctgga gacggtccag 720
cggctgttgc cggtgctgtg ccaggcccac ggcttgaccc cccagcaggt ggtggccatc 780
gccagcaata atggtggcaa gcaggcgctg gagacggtcc agcggctgtt gccggtgctg 840
tgccaggccc acggcttgac cccccagcag gtggtggcca tcgccagcaa tggcggtggc 900
aagcaggcgc tggagacggt ccagcggctg ttgccggtgc tgtgccaggc ccacggcttg 960 acccccccagc aggtggtggc catcgccagc aatggcggtg gcaagcaggc gctggagacg 1020
gtccagcggc tgttgccggt gctgtgccag gcccacggct tgaccccccca gcaggtggtg 1080 gccatcgcca gcaatggcgg tggcaagcag gcgctggaga cggtccagcg gctgttgccg 1140
gtgctgtgcc aggcccacgg cttgaccccg gagcaggtgg tggccatcgc cagccacgat 1200
ggcggcaagc aggcgctgga gacggtccag cggctgttgc cggtgctgtg ccaggcccac 1260
ggcttgaccc cggagcaggt ggtggccatc gccagccacg atggcggcaa gcaggcgctg 1320
gagacggtcc agcggctgtt gccggtgctg tgccaggccc acggcttgac cccggagcag 1380
gtggtggcca tcgccagcca cgatggcggc aagcaggcgc tggagacggt ccagcggctg 1440
ttgccggtgc tgtgccaggc ccacggcttg accccggagc aggtggtggc catcgccagc 1500
cacgatggcg gcaagcaggc gctggagacg gtccagcggc tgttgccggt gctgtgccag 1560
gcccacggct tgaccccgga gcaggtggtg gccatcgcca gcaatattgg tggcaagcag 1620
gcgctggaga cggtgcaggc gctgttgccg gtgctgtgcc aggcccacgg cttgaccccc 1680
cagcaggtgg tggccatcgc cagcaatggc ggtggcaagc aggcgctgga gacggtccag 1740
cggctgttgc cggtgctgtg ccaggcccac ggcttgaccc cggagcaggt ggtggccatc 1800
gccagccacg atggcggcaa gcaggcgctg gagacggtcc agcggctgtt gccggtgctg 1860
tgccaggccc acggcttgac cccggagcag gtggtggcca tcgccagcaa tattggtggc 1920
aagcaggcgc tggagacggt gcaggcgctg ttgccggtgc tgtgccaggc ccacggcttg 1980
acccctcagc aggtggtggc catcgccagc aatggcggcg gcaggccggc gctggagagc 2040
attgttgccc agttatctcg ccctgatccg gcgttggccg cgttgaccaa cgaccacctc 2100
gtcgccttgg cctgcctcgg cgggcgtcct gcgctggatg cagtgaaaaa gggattgggg 2160
gatcctatca gccgttccca gctggtgaag tccgagctgg aggagaagaa atccgagttg 2220
aggcacaagc tgaagtacgt gccccacgag tacatcgagc tgatcgagat cgcccggaac 2280
agcacccagg accgtatcct ggagatgaag gtgatggagt tcttcatgaa ggtgtacggc 2340
tacaggggca agcacctggg cggctccagg aagcccgacg gcgccatcta caccgtgggc 2400
tcccccatcg actacggcgt gatcgtggac accaaggcct actccggcgg ctacaacctg 2460
cccatcggcc aggccgacga aatgcagagg tacgtggagg agaaccagac caggaacaag 2520
cacatcaacc ccaacgagtg gtggaaggtg taccccctcca gcgtgaccga gttcaagttc 2580
ctgttcgtgt ccggccactt caagggcaac tacaaggccc agctgaccag gctgaaccac 2640
atcaccaact gcaacggcgc cgtgctgtcc gtggaggagc tcctgatcgg cggcgagatg 2700
atcaaggccg gcaccctgac cctggaggag gtgaggagga agttcaacaa cggcgagatc 2760
aacttcgcgg ccgactgata a 2781

<210> SEQ ID NO 156
<211> LENGTH: 2781
<212> TYPE: DNA
<213> ORGANISM: artificial
<220> FEATURE:
<223> OTHER INFORMATION: L-TALEN TGFbRII pCLS32940

<400> SEQUENCE: 156
atgggcgatc ctaaaaagaa acgtaaggtc atcgatatcg ccgatctacg cacgctcggc 60
tacagccagc agcaacagga gaagatcaaa ccgaaggttc gttcgacagt ggcgcagcac 120
cacgaggcac tggtcggcca cgggtttaca cacgcgcaca tcgttgcgtt aagccaacac 180
ccggcagcgt tagggaccgt cgctgtcaag tatcaggaca tgatcgcagc gttgccagag 240
gcgacacacg aagcgatcgt tggcgtcggc aaacagtggt ccggcgcacg cgctctggag 300
gccttgctca cggtggcggg agagttgaga ggtccaccgt tacagttgga cacaggccaa 360
cttctcaaga ttgcaaaacg tggcggcgtg accgcagtgg aggcagtgca tgcatggcgc 420
aatgcactga cgggtgcccc gctcaacttg accccggagc aggtggtggc catcgccagc 480
aatattggtg gcaagcaggc gctggagacg gtgcaggcgc tgttgccggt gctgtgccag 540
gcccacggct tgacccccca gcaggtggtg gccatcgcca gcaataatgg tggcaagcag 600
gcgctggaga cggtccagcg gctgttgccg gtgctgtgcc aggcccacgg cttgaccccg 660
gagcaggtgg tggccatcgc cagccacgat ggcggcaagc aggcgctgga gacggtccag 720
cggctgttgc cggtgctgtg ccaggcccac ggcttgaccc cggagcaggt ggtggccatc 780
gccagcaata ttggtggcaa gcaggcgctg gagacggtgc aggcgctgtt gccggtgctg 840
tgccaggccc acggcttgac cccggagcag gtggtggcca tcgccagcaa tattggtggc 900
aagcaggcgc tggagacggt gcaggcgctg ttgccggtgc tgtgccaggc ccacggcttg 960
accccggagc aggtggtggc catcgccagc cacgatggcg gcaagcaggc gctggagacg 1020
gtccagcggc tgttgccggt gctgtgccag gcccacggct tgaccccgga gcaggtggtg 1080
gccatcgcca gcaatattgg tggcaagcag gcgctggaga cggtgcaggc gctgttgccg 1140
gtgctgtgcc aggcccacgg cttgaccccg gagcaggtgg tggccatcgc cagcaatatt 1200
ggtggcaagc aggcgctgga gacggtgcag gcgctgttgc cggtgctgtg ccaggcccac 1260
ggcttgaccc cccagcaggt ggtggccatc gccagcaata atggtggcaa gcaggcgctg 1320
gagacggtcc agcggctgtt gccggtgctg tgccaggccc acggcttgac cccccagcag 1380
gtggtggcca tcgccagcaa tggcggtggc aagcaggcgc tggagacggt ccagcggctg 1440
ttgccggtgc tgtgccaggc ccacggcttg accccggagc aggtggtggc catcgccagc 1500
cacgatggcg gcaagcaggc gctggagacg gtccagcggc tgttgccggt gctgtgccag 1560
gcccacggct tgaccccgga gcaggtggtg gccatcgcca gcaatattgg tggcaagcag 1620
gcgctggaga cggtgcaggc gctgttgccg gtgctgtgcc aggcccacgg cttgaccccc 1680
cagcaggtgg tggccatcgc cagcaataat ggtggcaagc aggcgctgga gacggtccag 1740
cggctgttgc cggtgctgtg ccaggcccac ggcttgaccc cccagcaggt ggtggccatc 1800
gccagcaata atggtggcaa gcaggcgctg gagacggtcc agcggctgtt gccggtgctg 1860
tgccaggccc acggcttgac cccggagcag gtggtggcca tcgccagcaa tattggtggc 1920
aagcaggcgc tggagacggt gcaggcgctg ttgccggtgc tgtgccaggc ccacggcttg 1980
acccctcagc aggtggtggc catcgccagc aatggcggcg gcaggccggc gctggagagc 2040
attgttgccc agttatctcg ccctgatccg gcgttggccg cgttgaccaa cgaccacctc 2100
gtcgccttgg cctgcctcgg cgggcgtcct gcgctggatg cagtgaaaaa gggattgggg 2160
gatcctatca gccgttccca gctggtgaag tccgagctgg aggagaagaa atccgagttg 2220
aggcacaagc tgaagtacgt gccccacgag tacatcgagc tgatcgagat cgcccggaac 2280
agcacccagg accgtatcct ggagatgaag gtgatggagt tcttcatgaa ggtgtacggc 2340
tacaggggca agcacctggg cggctccagg aagcccgacg gcgccatcta caccgtgggc 2400
tcccccatcg actacggcgt gatcgtggac accaaggcct actccggcgg ctacaacctg 2460
cccatcggcc aggccgacga aatgcagagg tacgtggagg agaaccagac caggaacaag 2520
cacatcaacc ccaacgagtg gtggaaggtg taccccctcca gcgtgaccga gttcaagttc 2580
ctgttcgtgt ccggccactt caagggcaac tacaaggccc agctgaccag gctgaaccac 2640
atcaccaact gcaacggcgc cgtgctgtcc gtggaggagc tcctgatcgg cggcgagatg 2700
atcaaggccg gcaccctgac cctggaggag gtgaggagga agttcaacaa cggcgagatc 2760
aacttcgcgg ccgactgata a 2781

<210> SEQ ID NO 157
<211> LENGTH: 2781

<212> TYPE: DNA
<213> ORGANISM: artificial
<220> FEATURE:
<223> OTHER INFORMATION: R-TALEN TGFbRII pCLS32967

<400> SEQUENCE: 157

```
atgggcgatc ctaaaaagaa acgtaaggtc atcgatatcg ccgatctacg cacgctcggc     60

tacagccagc agcaacagga gaagatcaaa ccgaaggttc gttcgacagt ggcgcagcac    120

cacgaggcac tggtcggcca cgggtttaca cacgcgcaca tcgttgcgtt aagccaacac    180

ccggcagcgt tagggaccgt cgctgtcaag tatcaggaca tgatcgcagc gttgccagag    240

gcgacacacg aagcgatcgt tggcgtcggc aaacagtggt ccggcgcacg cgctctggag    300

gccttgctca cggtggcggg agagttgaga ggtccaccgt tacagttgga cacaggccaa    360

cttctcaaga ttgcaaaacg tggcggcgtg accgcagtgg aggcagtgca tgcatggcgc    420

aatgcactga cgggtgcccc gctcaacttg accccggagc aggtggtggc catcgccagc    480

cacgatggcg gcaagcaggc gctggagacg gtccagcggc tgttgccggt gctgtgccag    540

gcccacggct tgaccccgga gcaggtggtg gccatcgcca gccacgatgg cggcaagcag    600

gcgctggaga cggtccagcg gctgttgccg gtgctgtgcc aggcccacgg cttgaccccg    660

gagcaggtgg tggccatcgc cagccacgat ggcggcaagc aggcgctgga gacggtccag    720

cggctgttgc cggtgctgtg ccaggcccac ggcttgaccc cccagcaggt ggtggccatc    780

gccagcaatg gcggtggcaa gcaggcgctg gagacggtcc agcggctgtt gccggtgctg    840

tgccaggccc acggcttgac cccggagcag gtggtggcca tcgccagcaa tattggtggc    900

aagcaggcgc tggagacggt gcaggcgctg ttgccggtgc tgtgccaggc ccacggcttg    960

accccccagc aggtggtggc catcgccagc aatggcggtg gcaagcaggc gctggagacg   1020

gtccagcggc tgttgccggt gctgtgccag gcccacggct tgacccccca gcaggtggtg   1080

gccatcgcca gcaataatgg tggcaagcag gcgctggaga cggtccagcg gctgttgccg   1140

gtgctgtgcc aggcccacgg cttgaccccg gagcaggtgg tggccatcgc cagcaatatt   1200

ggtggcaagc aggcgctgga gacggtgcag gcgctgttgc cggtgctgtg ccaggcccac   1260

ggcttgaccc cccagcaggt ggtggccatc gccagcaata atggtggcaa gcaggcgctg   1320

gagacggtcc agcggctgtt gccggtgctg tgccaggccc acggcttgac cccccagcag   1380

gtggtggcca tcgccagcaa taatggtggc aagcaggcgc tggagacggt ccagcggctg   1440

ttgccggtgc tgtgccaggc ccacggcttg accccggagc aggtggtggc catcgccagc   1500

aatattggtg gcaagcaggc gctggagacg gtgcaggcgc tgttgccggt gctgtgccag   1560

gcccacggct tgacccccca gcaggtggtg gccatcgcca gcaataatgg tggcaagcag   1620

gcgctggaga cggtccagcg gctgttgccg gtgctgtgcc aggcccacgg cttgaccccc   1680

cagcaggtgg tggccatcgc cagcaatggc ggtggcaagc aggcgctgga gacggtccag   1740

cggctgttgc cggtgctgtg ccaggcccac ggcttgaccc cggagcaggt ggtggccatc   1800

gccagcaata ttggtggcaa gcaggcgctg gagacggtgc aggcgctgtt gccggtgctg   1860

tgccaggccc acggcttgac cccccagcag gtggtggcca tcgccagcaa tggcggtggc   1920

aagcaggcgc tggagacggt ccagcggctg ttgccggtgc tgtgccaggc ccacggcttg   1980

acccctcagc aggtggtggc catcgccagc aatggcggcg gcaggccggc gctggagagc   2040

attgttgccc agttatctcg ccctgatccg gcgttggccg cgttgaccaa cgaccacctc   2100

gtcgccttgg cctgcctcgg cgggcgtcct gcgctggatg cagtgaaaaa gggattgggg   2160
```

gatcctatca gccgttccca gctggtgaag tccgagctgg aggagaagaa atccgagttg 2220
aggcacaagc tgaagtacgt gccccacgag tacatcgagc tgatcgagat cgcccggaac 2280
agcacccagg accgtatcct ggagatgaag gtgatggagt tcttcatgaa ggtgtacggc 2340
tacaggggca agcacctggg cggctccagg aagcccgacg gcgccatcta caccgtgggc 2400
tcccccatcg actacggcgt gatcgtggac accaaggcct actccggcgg ctacaacctg 2460
cccatcggcc aggccgacga aatgcagagg tacgtggagg agaaccagac caggaacaag 2520
cacatcaacc ccaacgagtg gtggaaggtg taccccctcca gcgtgaccga gttcaagttc 2580
ctgttcgtgt ccggccactt caagggcaac tacaaggccc agctgaccag gctgaaccac 2640
atcaccaact gcaacggcgc cgtgctgtcc gtggaggagc tcctgatcgg cggcgagatg 2700
atcaaggccg gcaccctgac cctggaggag gtgaggagga agttcaacaa cggcgagatc 2760
aacttcgcgg ccgactgata a 2781

<210> SEQ ID NO 158
<211> LENGTH: 2781
<212> TYPE: DNA
<213> ORGANISM: artificial
<220> FEATURE:
<223> OTHER INFORMATION: L-TALEN TGFbRII pCLS32968

<400> SEQUENCE: 158
atgggcgatc ctaaaaagaa acgtaaggtc atcgatatcg ccgatctacg cacgctcggc 60
tacagccagc agcaacagga gaagatcaaa ccgaaggttc gttcgacagt ggcgcagcac 120
cacgaggcac tggtcggcca cgggtttaca cacgcgcaca tcgttgcgtt aagccaacac 180
ccggcagcgt tagggaccgt cgctgtcaag tatcaggaca tgatcgcagc gttgccagag 240
gcgacacacg aagcgatcgt tggcgtcggc aaacagtggt ccggcgcacg cgctctggag 300
gccttgctca cggtggcggg agagttgaga ggtccaccgt tacagttgga cacaggccaa 360
cttctcaaga ttgcaaaacg tggcggcgtg accgcagtgg aggcagtgca tgcatggcgc 420
aatgcactga cgggtgcccc gctcaacttg accccccagc aggtggtggc catcgccagc 480
aataatggtg gcaagcaggc gctggagacg gtccagcggc tgttgccggt gctgtgccag 540
gcccacggct tgaccccgga gcaggtggtg gccatcgcca gcaatattgg tggcaagcag 600
gcgctggaga cggtgcaggc gctgttgccg gtgctgtgcc aggcccacgg cttgaccccc 660
cagcaggtgg tggccatcgc cagcaataat ggtggcaagc aggcgctgga gacggtccag 720
cggctgttgc cggtgctgtg ccaggcccac ggcttgaccc cggagcaggt ggtggccatc 780
gccagcaata ttggtggcaa gcaggcgctg gagacggtgc aggcgctgtt gccggtgctg 840
tgccaggccc acggcttgac cccggagcag gtggtggcca tcgccagcaa tattggtggc 900
aagcaggcgc tggagacggt gcaggcgctg ttgccggtgc tgtgccaggc ccacggcttg 960
accccccagc aggtggtggc catcgccagc aataatggtg gcaagcaggc gctggagacg 1020
gtccagcggc tgttgccggt gctgtgccag gcccacggct tgaccccgga gcaggtggtg 1080
gccatcgcca gcaatattgg tggcaagcag gcgctggaga cggtgcaggc gctgttgccg 1140
gtgctgtgcc aggcccacgg cttgaccccc cagcaggtgg tggccatcgc cagcaatggc 1200
ggtggcaagc aggcgctgga gacggtccag cggctgttgc cggtgctgtg ccaggcccac 1260
ggcttgaccc cccagcaggt ggtggccatc gccagcaata atggtggcaa gcaggcgctg 1320
gagacggtcc agcggctgtt gccggtgctg tgccaggccc acggcttgac cccccagcag 1380
gtggtggcca tcgccagcaa tggcggtggc aagcaggcgc tggagacggt ccagcggctg 1440
ttgccggtgc tgtgccaggc ccacggcttg accccggagc aggtggtggc catcgccagc 1500
cacgatggcg gcaagcaggc gctggagacg gtccagcggc tgttgccggt gctgtgccag 1560
gcccacggct tgaccccgga gcaggtggtg gccatcgcca gccacgatgg cggcaagcag 1620
gcgctggaga cggtccagcg gctgttgccg gtgctgtgcc aggcccacgg cttgaccccc 1680
cagcaggtgg tggccatcgc cagcaatggc ggtggcaagc aggcgctgga gacggtccag 1740
cggctgttgc cggtgctgtg ccaggcccac ggcttgaccc cccagcaggt ggtggccatc 1800
gccagcaatg gcggtggcaa gcaggcgctg gagacggtcc agcggctgtt gccggtgctg 1860
tgccaggccc acggcttgac cccggagcag gtggtggcca tcgccagcca cgatggcggc 1920
aagcaggcgc tggagacggt ccagcggctg ttgccggtgc tgtgccaggc ccacggcttg 1980
acccctcagc aggtggtggc catcgccagc aatggcggcg gcaggccggc gctggagagc 2040
attgttgccc agttatctcg ccctgatccg gcgttggccg cgttgaccaa cgaccacctc 2100
gtcgccttgg cctgcctcgg cgggcgtcct gcgctggatg cagtgaaaaa gggattgggg 2160
gatcctatca gccgttccca gctggtgaag tccgagctgg aggagaagaa atccgagttg 2220
aggcacaagc tgaagtacgt gccccacgag tacatcgagc tgatcgagat cgcccggaac 2280
agcacccagg accgtatcct ggagatgaag gtgatggagt tcttcatgaa ggtgtacggc 2340
tacaggggca agcacctggg cggctccagg aagcccgacg gcgccatcta caccgtgggc 2400
tcccccatcg actacggcgt gatcgtggac accaaggcct actccggcgg ctacaacctg 2460
cccatcggcc aggccgacga aatgcagagg tacgtggagg agaaccagac caggaacaag 2520
cacatcaacc ccaacgagtg gtggaaggtg tacccctcca gcgtgaccga gttcaagttc 2580
ctgttcgtgt ccggccactt caagggcaac tacaaggccc agctgaccag gctgaaccac 2640
atcaccaact gcaacggcgc cgtgctgtcc gtggaggagc tcctgatcgg cggcgagatg 2700
atcaaggccg gcaccctgac cctggaggag gtgaggagga agttcaacaa cggcgagatc 2760
aacttcgcgg ccgactgata a 2781

<210> SEQ ID NO 159
<211> LENGTH: 49
<212> TYPE: DNA
<213> ORGANISM: artificial
<220> FEATURE:
<223> OTHER INFORMATION: TRAC TALEN target sequence

<400> SEQUENCE: 159
ttgtcccaca gatatccaga accctgaccc tgccgtgtac cagctgaga 49

<210> SEQ ID NO 160
<211> LENGTH: 49
<212> TYPE: DNA
<213> ORGANISM: artificial
<220> FEATURE:
<223> OTHER INFORMATION: CD52 TALEN target sequence

<400> SEQUENCE: 160
ttcctcctac tcaccatcag cctcctggtt atggtacagg taagagcaa 49

<210> SEQ ID NO 161
<211> LENGTH: 502
<212> TYPE: PRT
<213> ORGANISM: artificial
<220> FEATURE:
<223> OTHER INFORMATION: P4 CAR full sequence

<400> SEQUENCE: 161

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Thr Pro Ser Gln Thr Leu Ser Leu Thr Cys Ala Ile Ser Gly Asp
        35                  40                  45

Ser Val Ser Ser Asn Ser Ala Thr Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Met Ser Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Gly Met Met Thr Tyr Tyr
        115                 120                 125

Tyr Gly Met Asp Val Trp Gly Gln Gly Thr Thr Val Thr Val Ser Ser
    130                 135                 140

Gly Ile Leu Gly Gly Gly Gly Gly Ser Gly Gly Gly Gly Ser Gly Gly
145                 150                 155                 160

Gly Gly Ser Gln Pro Val Leu Thr Gln Ser Ser Ser Leu Ser Ala Ser
                165                 170                 175

Pro Gly Ala Ser Ala Ser Leu Thr Cys Thr Leu Arg Ser Gly Ile Asn
            180                 185                 190

Val Gly Pro Tyr Arg Ile Tyr Trp Tyr Gln Gln Lys Pro Gly Ser Pro
        195                 200                 205

Pro Gln Tyr Leu Leu Asn Tyr Lys Ser Asp Ser Asp Lys Gln Gln Gly
    210                 215                 220

Ser Gly Val Pro Ser Arg Phe Ser Gly Ser Lys Asp Ala Ser Ala Asn
225                 230                 235                 240

Ala Gly Val Leu Leu Ile Ser Gly Leu Arg Ser Glu Asp Glu Ala Asp
                245                 250                 255

Tyr Tyr Cys Met Ile Trp His Ser Ser Ala Ala Val Phe Gly Gly Gly
            260                 265                 270

Thr Gln Leu Thr Val Leu Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415
```

-continued

```
Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```